(12) United States Patent
Rice et al.

(10) Patent No.: US 9,663,789 B2
(45) Date of Patent: May 30, 2017

(54) PME-1 AS A BIOMARKER TO PREDICT AND DIAGNOSE ENDOMETRIAL AND BREAST CANCER AND GENE SILENCING OF PME-1 TO INHIBIT EPITHELIAL TO MESENCHYMAL TRANSITION

(71) Applicants: Lyndi M. Rice, Philadelphia, PA (US); Michelle Pusey, Bordentown, NJ (US)

(72) Inventors: Lyndi M. Rice, Philadelphia, PA (US); Michelle Pusey, Bordentown, NJ (US)

(73) Assignee: MEDICAL DIAGNOSTIC LABORATORIES, LLC, Hamilton, NJ (US)

( * ) Notice: Subject to any disclaimer, the term of this patent is extended or adjusted under 35 U.S.C. 154(b) by 0 days.

(21) Appl. No.: 14/514,859

(22) Filed: Oct. 15, 2014

(65) Prior Publication Data

US 2015/0284723 A1 Oct. 8, 2015

Related U.S. Application Data

(63) Continuation-in-part of application No. 14/263,085, filed on Apr. 28, 2014.

(60) Provisional application No. 61/905,947, filed on Nov. 19, 2013, provisional application No. 61/816,472, filed on Apr. 26, 2013.

(51) Int. Cl.
| | | |
|---|---|---|
| *A61K 31/70* | (2006.01) |
| *C07H 21/02* | (2006.01) |
| *C07H 21/04* | (2006.01) |
| *C12N 15/113* | (2010.01) |
| *A61K 31/713* | (2006.01) |
| *A61K 31/7105* | (2006.01) |
| *C12Q 1/68* | (2006.01) |
| *G01N 33/574* | (2006.01) |
| *C12N 5/00* | (2006.01) |

(52) U.S. Cl.
CPC ........ *C12N 15/1137* (2013.01); *A61K 31/713* (2013.01); *A61K 31/7105* (2013.01); *C12Q 1/6886* (2013.01); *G01N 33/57415* (2013.01); *C12N 2310/14* (2013.01); *C12N 2310/531* (2013.01); *C12Q 2600/158* (2013.01); *C12Y 301/01089* (2013.01); *G01N 2333/918* (2013.01)

(58) Field of Classification Search
None
See application file for complete search history.

(56) References Cited

U.S. PATENT DOCUMENTS

2014/0135377 A1* 5/2014 Westermarck ....... A61K 31/553
514/44 A

OTHER PUBLICATIONS

Hudis et al., The Oncologist vol. 16(suppl 1):1-11, 2011.*

* cited by examiner

*Primary Examiner* — Sean McGarry
(74) *Attorney, Agent, or Firm* — Siu K. Lo; Thomas R. Savitsky

(57) ABSTRACT

Disclosed are methods of attenuating activity of the PME-1 gene. siRNAs or shRNAs are used to target against PME-1, thereby reducing the PME-1 mRNA. It is disclosed that the siRNAs or shRNAs targeted against PME-1 attenuate the epithelial to mesenchymal transition, thereby inhibit endometrial cancer and triple negative breast cancer development. A kit containing siRNA or shRNA reagents for attenuating the PME-1 gene expression is also disclosed.

5 Claims, 37 Drawing Sheets
(16 of 37 Drawing Sheet(s) Filed in Color)

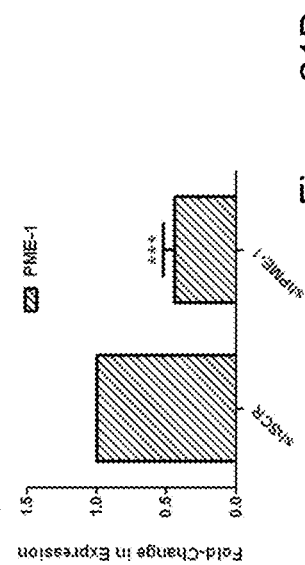
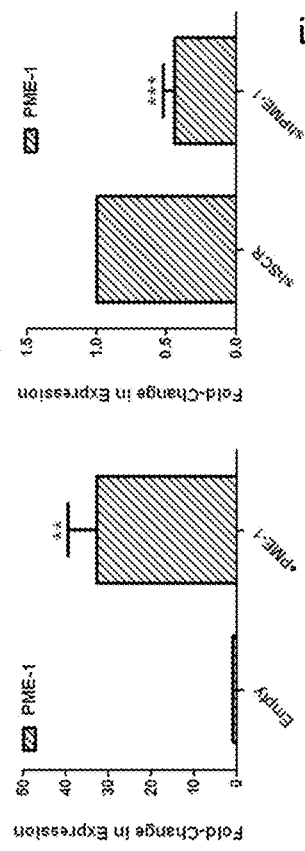
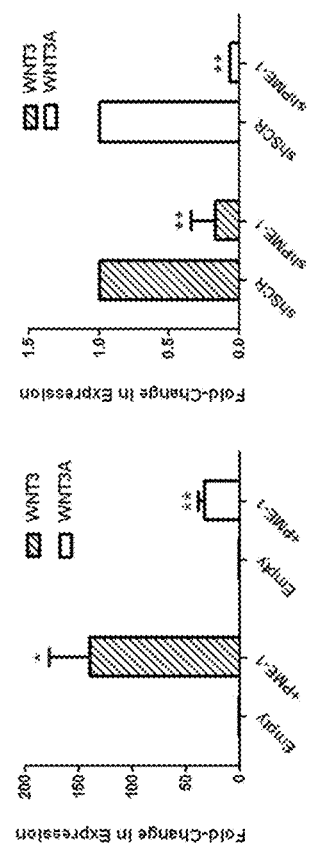
Figure 21

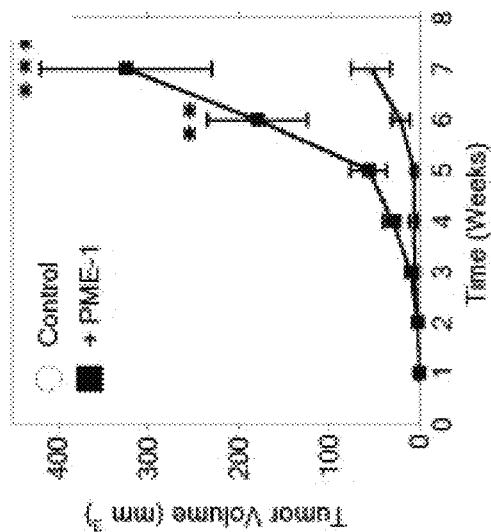
Figure 28A
Figure 28B
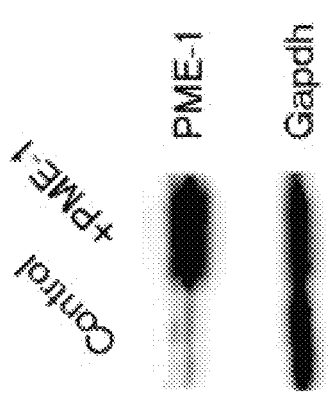
Figure 28C
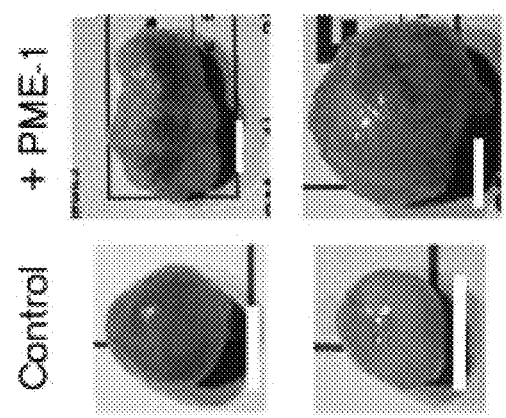
Figure 28D

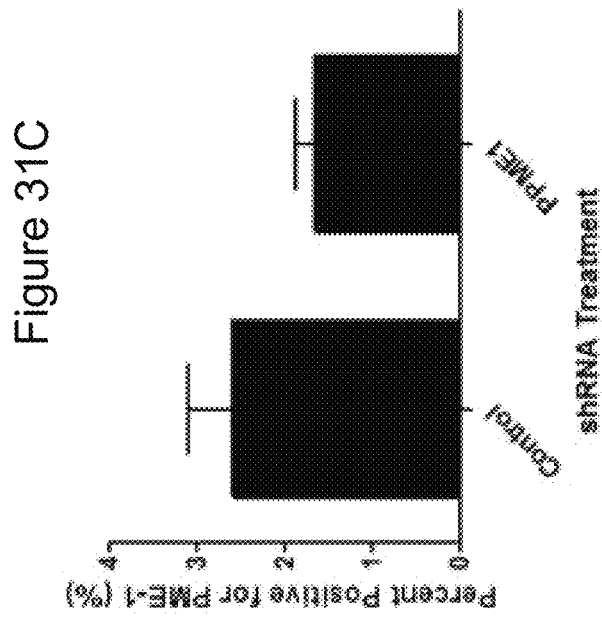
Figure 31C
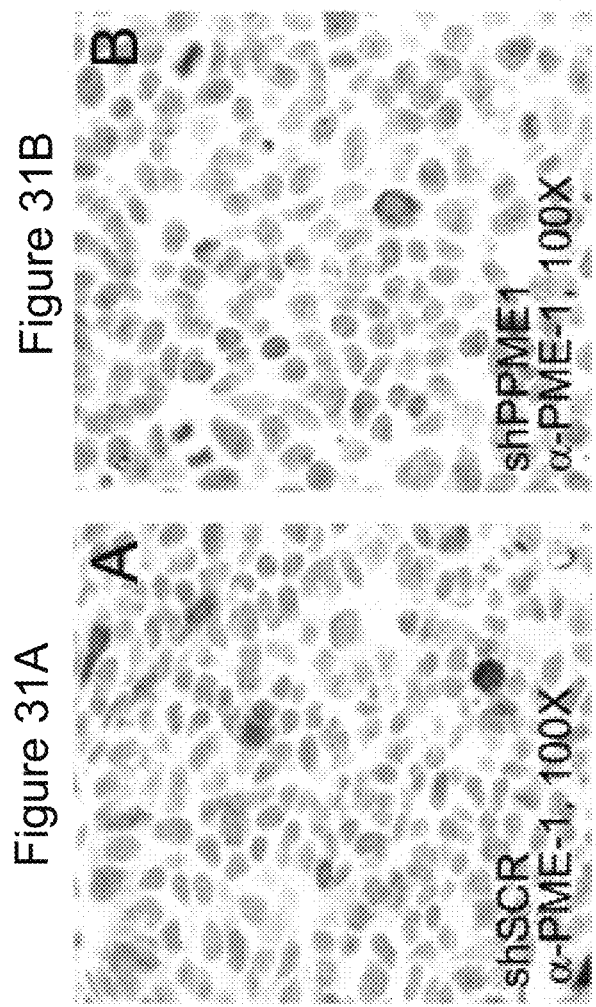
Figure 31B
Figure 31A

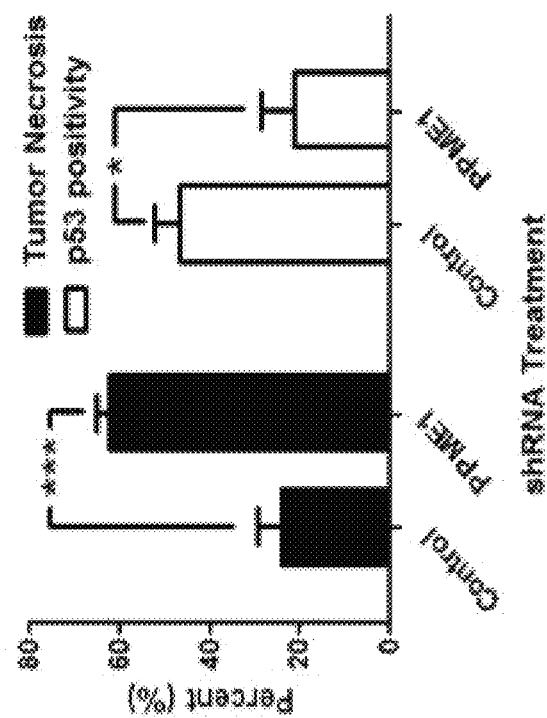
Figure 32A
Figure 32B
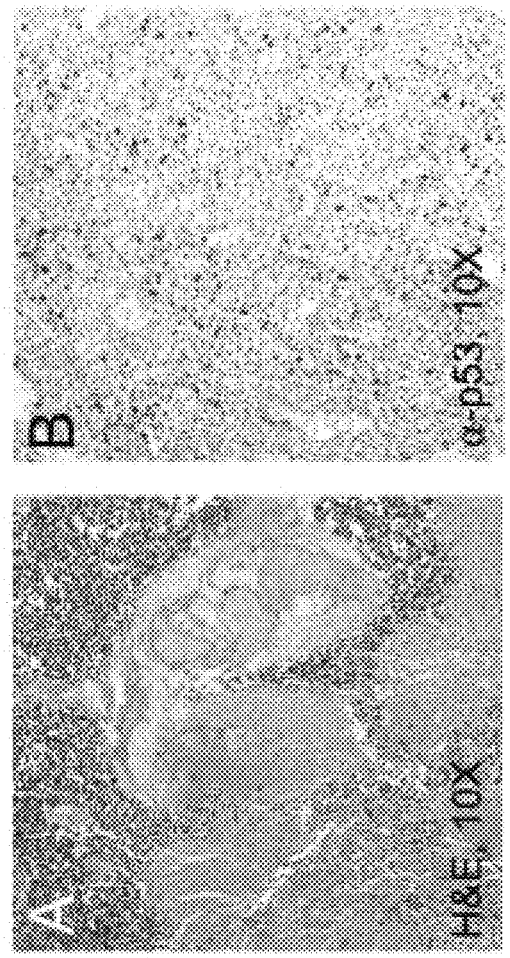
Figure 32C

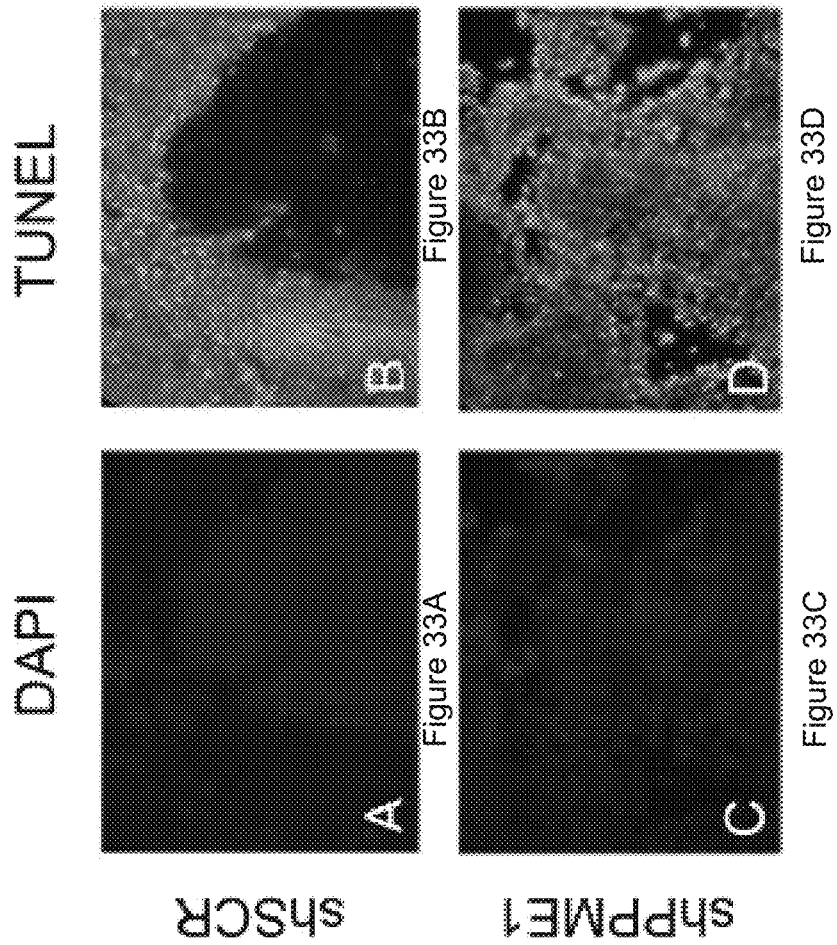

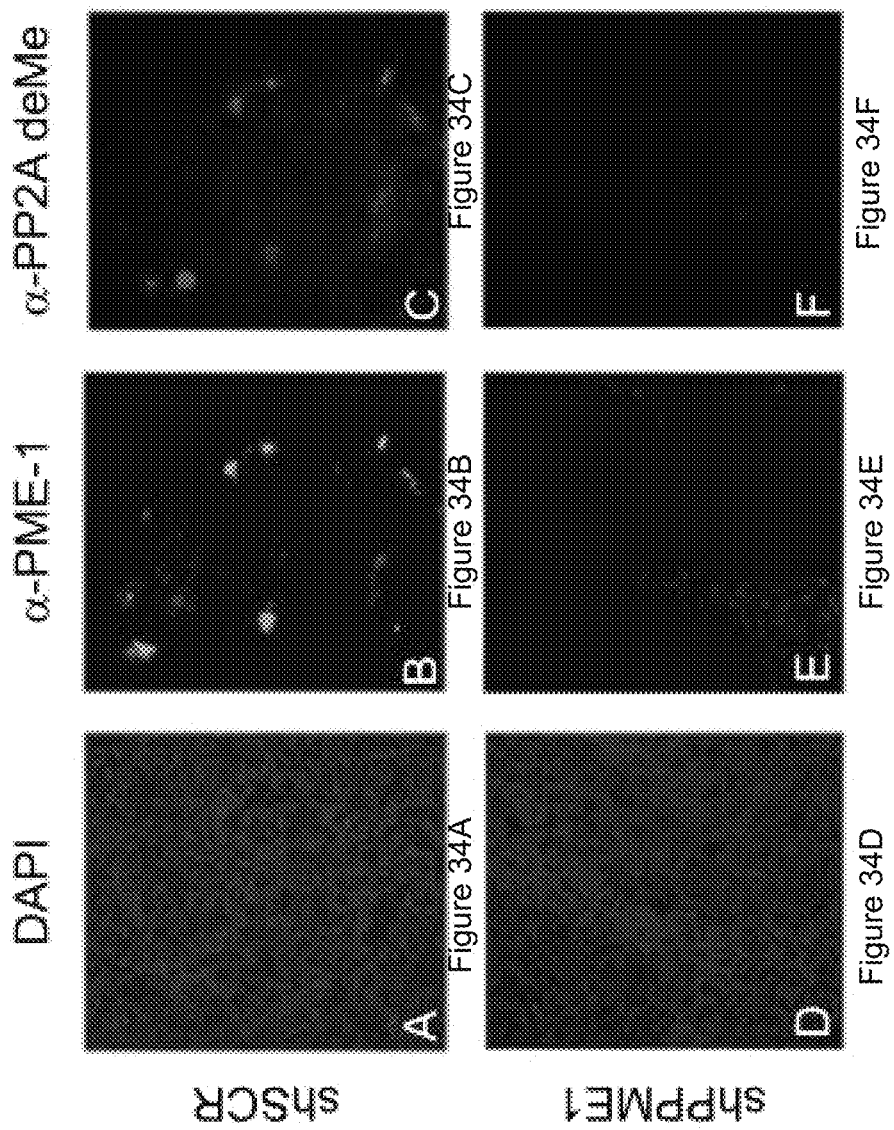

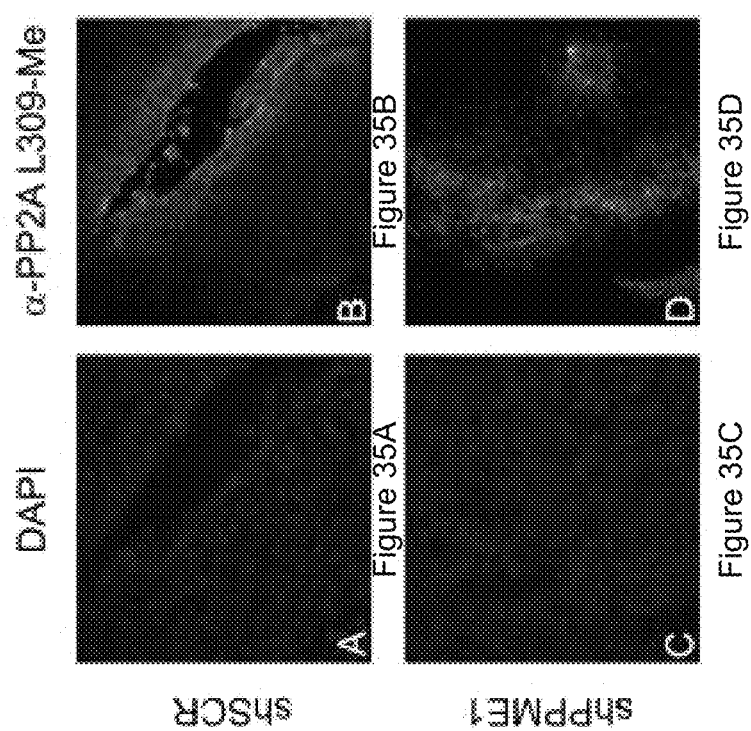

PME-1 AS A BIOMARKER TO PREDICT AND DIAGNOSE ENDOMETRIAL AND BREAST CANCER AND GENE SILENCING OF PME-1 TO INHIBIT EPITHELIAL TO MESENCHYMAL TRANSITION

CROSS-REFERENCE TO RELATED APPLICATION

This application is a Continuation-In-Part of U.S. patent application Ser. No. 14/263,085 filed on Apr. 28, 2014, which claims the benefit under 35 U.S.C. §119(e) to U.S. Provisional Application No. 61/816,472 filed Apr. 26, 2013 and Provisional Application No. 61/905,947 filed Nov. 19, 2013, the contents of which are incorporated by reference herein in their entirety.

FIELD OF THE INVENTION

The present invention generally relates to the discovery that PME-1 represents a novel cancer biomarker (PME-1 is a biomarker used to predict and diagnose an increased risk of endometrial cancer and breast cancer) and gene silencing of the PME-1 gene to inhibit the epithelial to mesenchymal transition which is the characteristics of endometrial cancer and breast cancer.

BACKGROUND OF THE INVENTION

Endometrial cancer refers to the malignancies of endometrium of the uterus. It is the most common gynecologic cancers in the United States, with over 35,000 women diagnosed each year. It represents the third most common cause of gynecologic cancer death, behind ovarian and cervical cancer (Siegel, Ca Cancer J Clin. 63:11-30 (2013)). Endometrioid adenocarcinoma often develops in the setting of endometrial hyperplasia, and presents with vaginal bleeding. The most common therapeutic approach of endometrial cancer is a total abdominal hysterectomy with bilateral salpingo-oophorectomy.

When discovered in its early stages, endometrial cancer is highly curable (Engelsen, APMIS 117: 693-707 (2009)). There are presently several methods of clinical evaluation for the presence of endometrial cancer, including Pap smear. Notably, Pap smear is ineffective in detecting endometrial cancer, while it is useful in screening for cervical cancer. Office endometrial biopsy still remains the traditional diagnostic method, in which both endometrial and endocervical materials are often sampled. In the event that endometrial biopsy does not yield sufficient diagnostic material, a dilation and curettage (D&C) is necessary for diagnosing the cancer. Hysteroscopy permits the direct visualization of the uterine cavity and can be used to detect the presence of lesions or tumors. However, such procedure is not practical because it requires strict sterile environments and physician's competent skill, as well as the high associated costs.

Transvaginal ultrasound is a non-invasive method that is used to evaluate the endometrial thickness in women with postmenopausal bleeding and is increasingly being used to evaluate for endometrial cancer. However, the method is often not sensitive to detect early endometrial cancer. Studies suggest measurement of serum p53 antibody may be used to identify high-risk endometrial cancer.

There are currently no other specific biomarkers that exist for endometrial cancer as diagnosis is usually dependent on histology. Several potential biomarkers have been correlated to endometrial cancer in studies, but often these results are inconsistent (Engelsen, APMIS 117: 693-707 (2009)), thus making it difficult to develop a therapy.

Brest cancer may also undergo the epithelial to mesenchymal transition as in endometrial cancer. In the USA, 180,000 women are diagnosed annually with new cases of breast cancer and it is the second leading cause of cancer-related death in women in the US (Polyak, et al., Biochim Biophys Acta. 2001 Nov. 30; 1552(1):1-13).

Breast cancers are generally treated by targeting the estrogen, progesterone or human epidermal growth factor receptor type 2 (HER2) receptors. Clinical trials on humans using anti-cancer drugs and anti-HER2 antibodies have been conducted and achieved improved clinical response and overall survival (Molin, M A, et al., Cancer Res 61: 4744-4749 (2001)). But in the case of triple negative breast cancer (TNBC), such targeted treatment is ineffective because TNBC lacks estrogen receptors, progesterone receptors, and human epidermal growth factor receptor type 2 (HER2/neu). While TNBC does respond to chemotherapeutics, TNBC becomes aggressive. Treatment with chemotherapy unfortunately has high recurrence and poor clinical outcome.

Accordingly, there is a continuing need in identifying potential biomarker for endometrial cancer and breast cancer in humans and novel compounds that inhibit epithelial to mesenchymal transition and thus inhibit endometrial and breast cancer development and growth.

SUMMARY OF THE INVENTION

The present invention provides the use of protein methyl esterase 1 (PME-1) as a biomarker for endometrial cancer, as evidenced by the correlation between PME-1 expression levels and endometrial cancer. The present invention further provides methods, such as real-time PCR, for quantifying the expression level of PME-1. The application of the correlation between increased levels of PME-1 expression and endometrial cancer is useful in the diagnosis of endometrial cancer. An increased risk of endometrial cancer is evidenced when there is an increased expression of PME-1 (either protein or mRNA) in a woman with endometrial cancer relative to that of a healthy woman (free from endometrial cancer).

In one aspect, the present invention provides characterization the PME-1 gene and identification of PME-1 protein that is associated with development of endometrial cancer. It is discovered that the PME-1 expression level in endometrial tissues correlates with the higher stages (i.e., stages II and III) of endometrial cancer in humans.

In one aspect, the present invention provides characterization the PME-1 gene and identification of PME-1 protein that is associated with development of endometrial cancer. It is discovered that the PME-1 expression level in endometrial tissues correlates with the higher grades (i.e., stages II and III) of endometrial cancer in humans.

In one aspect, the present invention provides using PME-1 as a biomarker in endometrial cancer and further provides a novel approach to use RNA interference (RNAi) (includes siRNA or shRNA) to influence the PME-1 expression and thus altering the cancer pathogenesis in human.

In one aspect, the present invention provides using PME-1 protein expression level (compared with normal subjects) (i.e., women with no history of endometrial cancer) to predict or diagnose endometrial cancer in an individual. An increased risk of endometrial cancer is when there is an increased PME-1 expression level when comparing a woman at risk relative to a normal individual.

In one aspect, the present invention provides a method of using RNAi (e.g., siRNA or shRNA) approaches targeting against the PME-1 expression in a human subject so as to attenuate the epithelial mesenchymal transition and thus attenuating endometrial cancer pathogenesis.

In one aspect, the present invention provides a method of using RNAi (e.g., siRNA or shRNA) approaches targeting against the PME-1 expression in a human subject so as to attenuate the epithelial mesenchymal transition and thus attenuating breast cancer pathogenesis. Preferably, the breast cancer is triple negative breast cancer.

In one aspect, the present invention provides RNAi as well as compositions containing RNAi for inhibiting the expression of the PME-1 gene in a mammal. The present invention further provides compositions and methods for treating pathological conditions and diseases mediated by the expression of the PME-1 gene, such as endometrial cancer and breast cancer. The RNAi of the present invention comprises an RNA strand (the anti-sense strand) having a region sufficient to hybridize to mRNA of PME-1 (preferably, the 3-UTR of the mRNA) and causes PME-1 mRNA to be degraded. Preferably, the RNAi (i.e., siRNA or shRNA) is more than about 15 nucleotides and less than about 30 nucleotides in length, generally about 20-25 nucleotides in length, and is substantially complementary to at least part of an mRNA transcript of the PME-1 gene. Preferably, the RNAi is about 19-21 nucleotides in length.

In one aspect, the present invention provides a method of inhibiting the gene expression of PME-1 in a endometrial cell, comprising the steps of: a) providing a RNAi (siRNA or shRNA) targeted against PME-1 mRNA; b) exposing the RNAi to a cell suspected of developing into endometrial tumor, wherein said RNAi inhibits the gene expression of PME-1 in said endometrial cell.

In one aspect, the present invention provides a method of inhibiting the gene expression of PME-1 in a breast cancer cell, comprising the steps of: a) providing an RNAi (siRNA or shRNA) targeted against PME-1 mRNA; b) exposing the RNAi to a breast cancer cell, wherein said RNAi inhibits the gene expression of PME-1 in said breast cancer cell. Preferably, the breast cancer cell is a triple negative breast cancer cell.

In one aspect, the present invention provides a method of inhibiting the epithelial to mesenchymal transition (EMT) in a endometrial cell suspected of developing into a cancerous endometrial cell, comprising the steps of: a) providing a RNAi (siRNA or shRNA) targeted against PME-1 mRNA; b) exposing the RNAi to a cell suspected of developing into a cancerous endometrial cell, wherein said RNAi inhibits the EMT, as evidenced by an increase in expression level of E-cadherin and decrease in expression level of vimentin in said endometrial cell.

In one aspect, the present invention provides a method for inhibiting endometrial cancer progression in a human, comprising the steps of administering to a human suspected of suffering from an endometrial cancer an effective amount of an RNAi (siRNA or shRNA) targeted against PME-1 mRNA, wherein the RNAi inhibits endometrial cancer progression.

In one aspect, the present invention provides a method for inhibiting triple negative breast cancer progression in a human, comprising the steps of administering to a human suspected of suffering from a triple negative breast cancer an effective amount of an RNAi (siRNA or shRNA) targeted against PME-1 mRNA, wherein the RNAi inhibits triple negative breast cancer progression.

In one aspect, the present invention provides a method of detecting an increased expression level of PME-1 in an endometrial tissue obtained from a woman suspected of suffering from endometrial cancer, comprising the steps of: (a) obtaining an endometrial tissue from a woman suspected of suffering from endometrial cancer; (b) preparing a lysate from said endometrial tissue; and (c) quantifying an expression level of PME-1 protein in said prepared lysate. The increased expression level of PME-1 protein relative to that of a normal endometrial tissue is indicative of an increased risk in endometrial cancer in said woman. Preferably, the expression level of protein can be quantified using Western blot analysis or ELISA. Expression mRNA level can be measured using qRT-PCR. Preferably, the total RNA is isolated using guanidinium thiocyanate or phenol-chloroform. The increased PME-1 expression level is associated with higher grades of endometrial cancer (i.e., grade II or grade III).

In one aspect, the present invention provides a kit for detecting endometrial cancer in a human, comprising: a) a reagent for quantifying PME-1 expression level; and b) an instruction for use of said reagent in quantifying PME-1 protein expression level. An increased PME-1 protein expression level is indicative of an increased risk in endometrial cancer.

In one aspect, the present invention provides a method of inhibiting epithelial to mesenchymal transition of an endometrial cell, comprising the steps of i) providing RNAi targeted against PME-1 gene, said RNAi hybridizes to a target sequence of PME-1 mRNA; and (ii) exposing said RNAi to an endometrial cell. The RNAi inhibits said epithelial to mesenchymal transition as evidenced by at least one of the feature selected from the group consisting of increased E-cadherin expression, reduced vimentin expression and reduced foci formation. Preferably, the RNAi is siRNA or shRNA. Preferably, the siRNA is SEQ ID NO: 16 and 17.

In one aspect, the present invention provides a method for inhibiting epithelial to mesenchymal transition in endometrial cells of a woman suspected of suffering from endometrial cancer, comprising the step of administering to said woman an effective amount of a RNAi targeted against PME-1 gene, whereby said RNAi inhibits PME-1 gene expression so as to inhibit epithelial to mesenchymal transition in endometrial cells.

In one aspect, the present invention provides a method for inhibiting epithelial to mesenchymal transition in a triple negative breast cell in a woman suffering from triple negative breast cancer, comprising the step of administering to said woman an effective amount of a RNAi targeted against PME-1 gene, whereby said RNAi inhibits PME-1 gene expression so as to inhibit epithelial to mesenchymal transition in triple negative breast cancer cell to inhibit the cancer growth.

In one aspect, the present invention provides a method of treating a human subject suffering from triple negative breast cancer and is in need of treatment, comprising the steps of: a) identifying a human subject having a triple negative breast cancer and in need of treatment thereof; and administering to said human subject an effective amount of a RNAi target against PME-1 selected from the group consisting of siRNA and shRNA, wherein said RNAi reduces the gene expression of PME-1 in said triple negative breast cancer and thereby inhibits tumor growth of said triple negative breast cancer.

Preferably, the siRNA is selected from the group consisting of SEQ ID NO: 16 and SEQ ID NO: 17.

Preferably, the shRNA is having a target sequence selected from the group consisting of SEQ ID NO: 2 and SEQ ID NO: 3.

In one aspect, the present invention provides a method of inhibiting tumor growth of a triple negative breast cancer cell, comprising the step of exposing a triple negative breast cancer cell with a RNAi selected from the group consisting of siRNA and shRNA targeted against PME-1, wherein said RNAi reduces PME-1 gene expression and thereby inhibits tumor growth of said triple negative breast cancer cell.

Preferably, the siRNA is selected from the group consisting of SEQ ID NO: 16 and SEQ ID NO: 17. Preferably, the shRNA is having a target sequence selected from the group consisting of SEQ ID NO: 2 and SEQ ID NO: 3.

Preferably, the shRNA is contained in an adenoviral expression vector (adenoviral-Type 5 (dE1/E3)) operably linked to shRNA via a U6 promoter.

In one aspect, the present invention provides a composition comprising a shRNA contained in an adenoviral expression vector operably linked to said shRNA and a pharmaceutical acceptable excipient, wherein said shRNA consists target sequence of SEQ ID NO: 2 or SEQ ID NO: 3.

In one aspect, the present invention provides a composition comprising a siRNA target against PME-1 gene and a pharmaceutically acceptable excipient, wherein said siRNA is selected from the group consisting of SEQ ID NOs: 16 and 17.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 14:
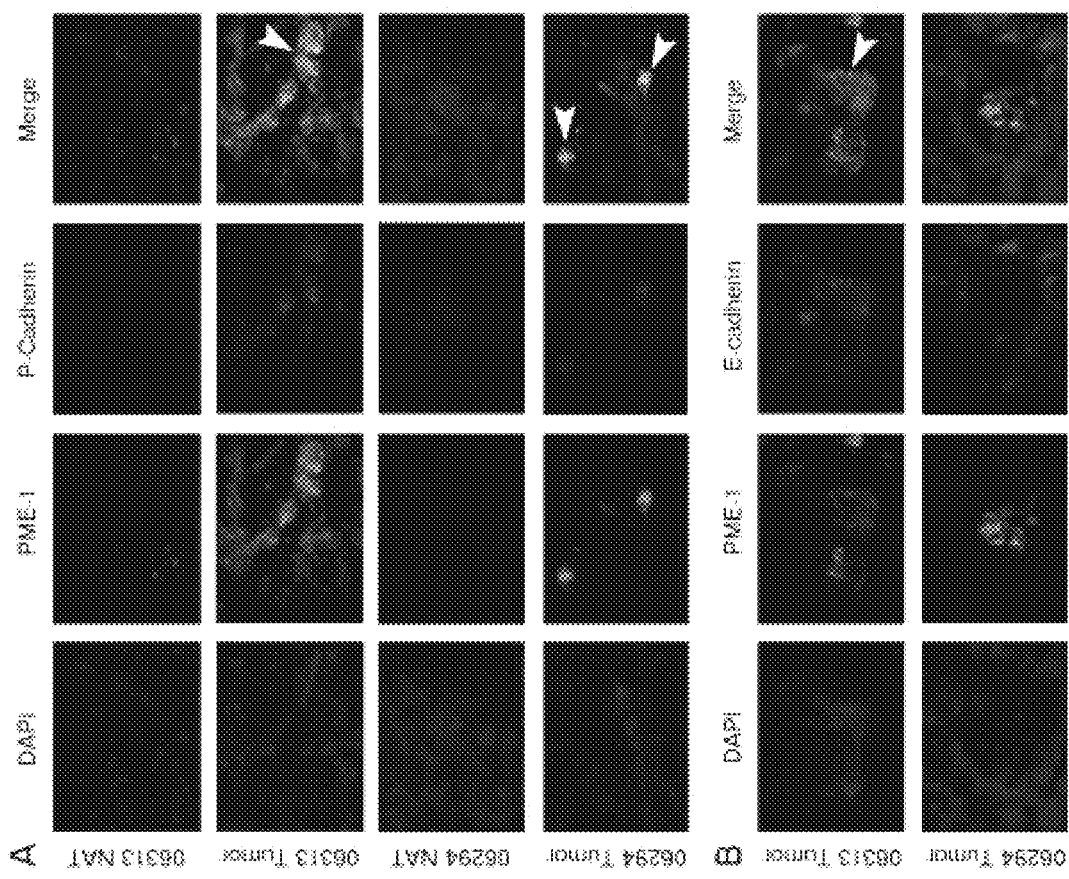
FIG. 14A depicts human endometrial tissue sections immunostained with an anti-PME-1 antibody (green), anti-P-cadherin antibody (red) and DAPI nuclear stain (blue). Merged images of red and green staining depict cells that express both markers, indicated by yellow color and arrows.
FIG. 14B depicts human endometrial tissue sections immunostained with an anti-PME-1 antibody (green), anti-E-cadherin antibody (red) and DAPI nuclear stain (blue). Merged images of red and green staining depict cells that express both markers, indicated by yellow color and arrows.

Representative images are shown in FIG. 14 from patients diagnosed with grade 1 endometrioid adenocarcinoma (06313) or grade 3 endometrioid adenocarcinoma (06294). P-cadherin is a marker for aggressive endometrial cancer (FIG. 14A) and E-cadherin is a marker for cells retaining epithelial characteristics (FIG. 14B).

Figure 15:
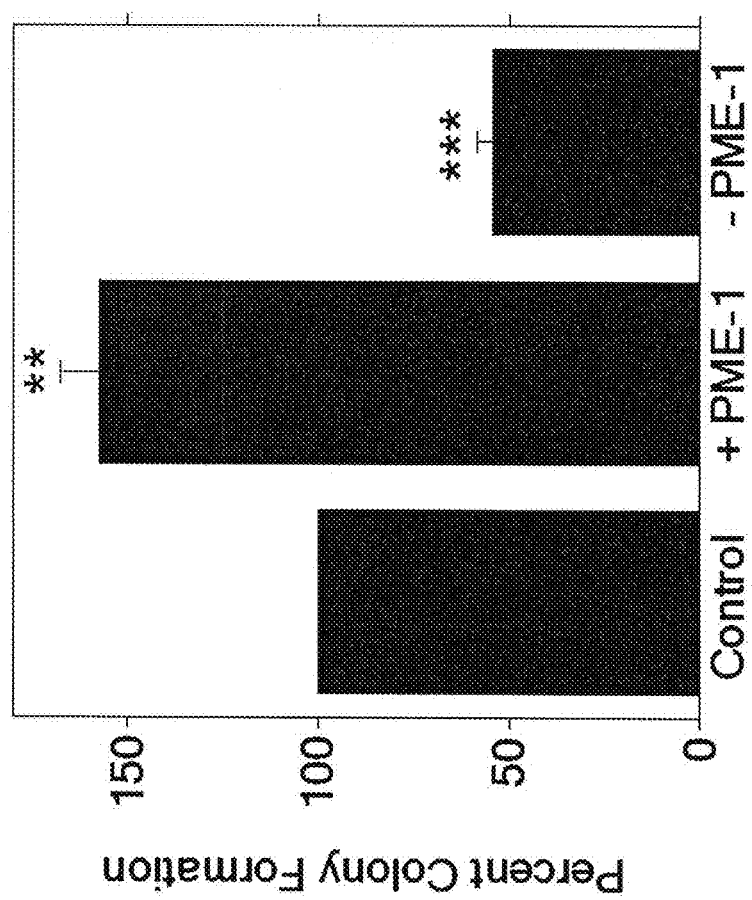

FIG. 15 depicts RL95-2 cells expressing empty vector (control), over-expressing PME-1 (+PME-1), or expressing shRNA against PME-1 (−PME-1) that were grown on Matrigel to determine the effects of PME-1 on invasive growth cancer phenotypes. The colonies of cells were counted, the means are shown, with error bars representing SEM and the significance was calculated by the standard student's t test; where *p<0.05, p<0.01, *p<0.001.

Figure 16:
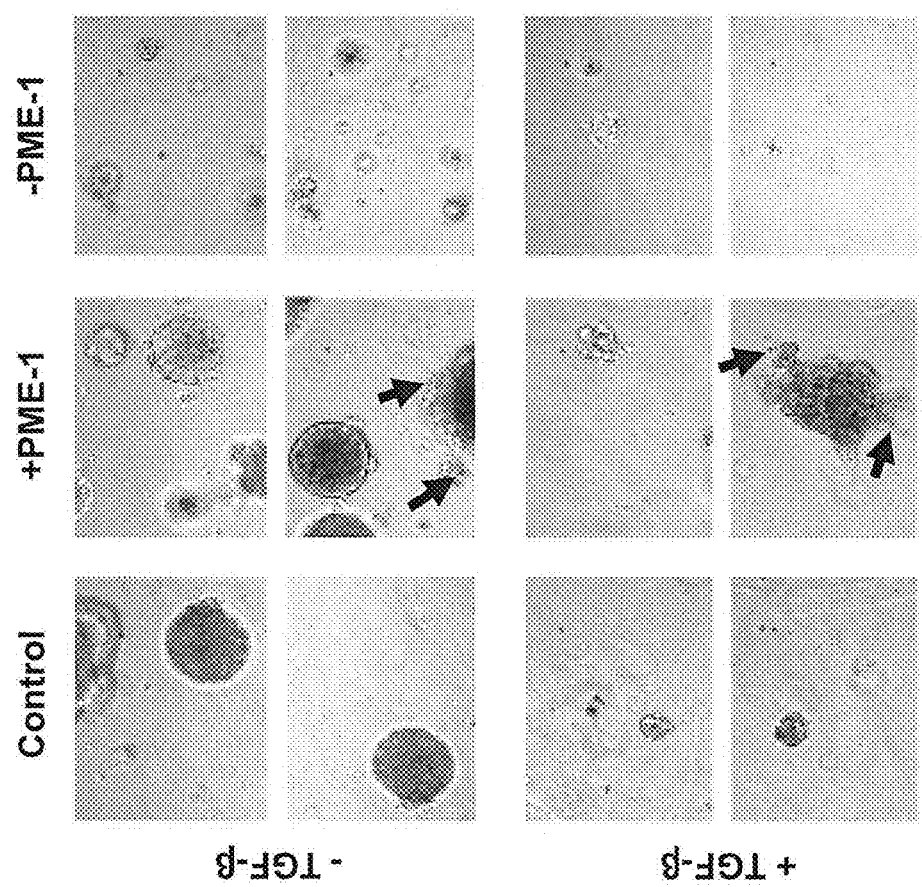

FIG. 16 depicts the growth of RL95-2 cells in Matrigel for 10 days in the presence and absence of TGF-β (which stimulates EMT). The same amount of RL95-2 cells were also plated and the expression of the empty vector (control), the over-expression of PME-1 (+PME-1), and the expression of shRNA against PME-1 (−PME-1) are shown.

Figure 13:
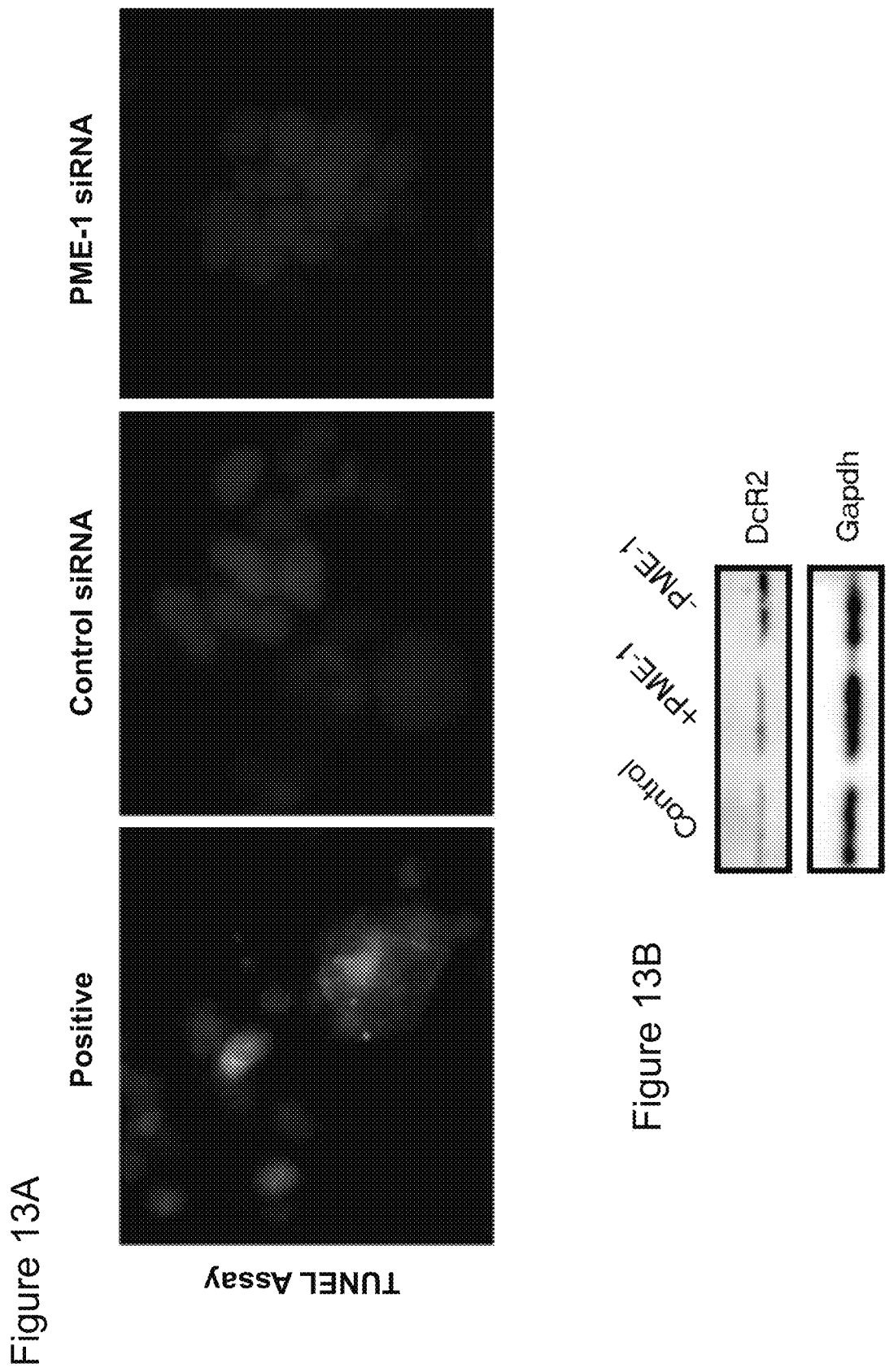
FIG. 13A depicts RL95-2 cells treated with control siRNA or siRNA targeted against PME-1 sequence (SEQ ID NO: 4). These cells were subjected to a TUNEL assay to detect apoptosis or fragmented DNA. A positive control was included, in which cells were treated with DNase I.
FIG. 13B depicts RL95-2 cells expressing empty vector (control), over-expression of PME-1 (+PME-1) and the expression of shRNA targeted against PME-1 (−PME-1). A Western blot analysis was performed probing for DcR2, a marker of senescent cells, compared to the loading control GAPDH.
Figure 17:
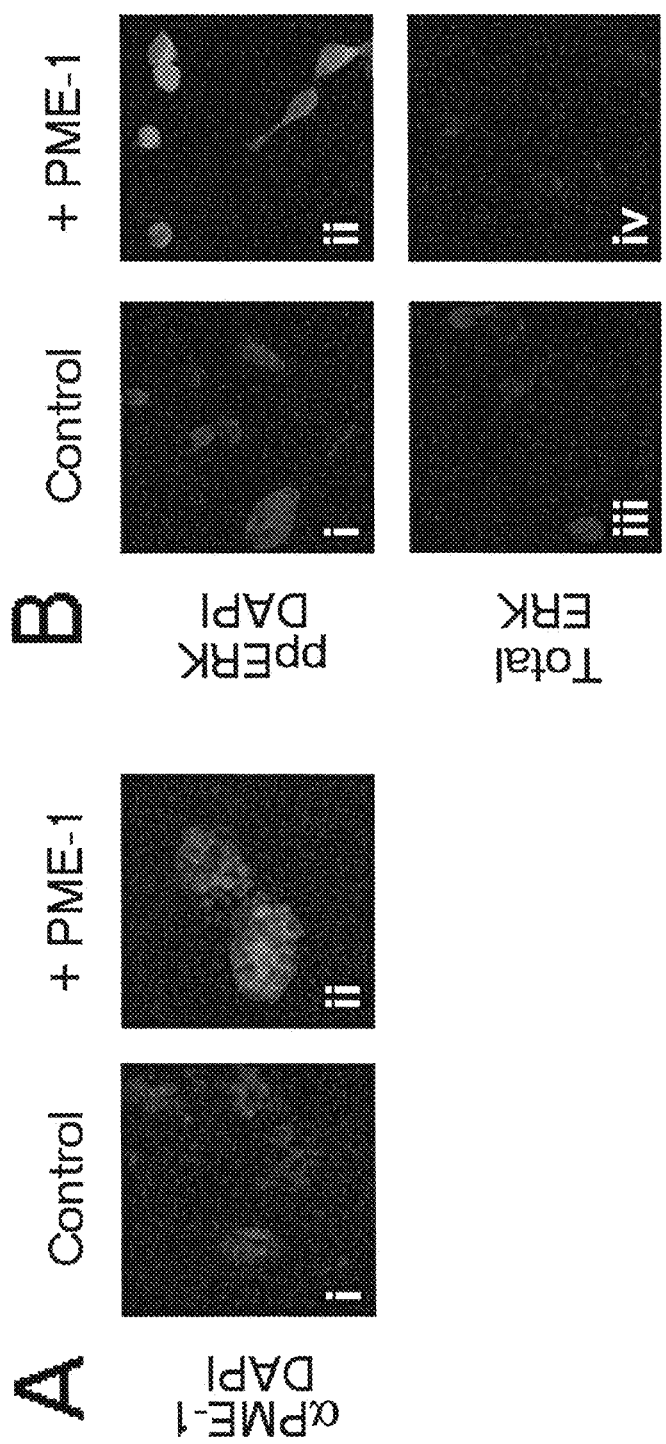

FIG. 17 depicts the immunofluorescence of RL95-2 cells expressing empty vector (control) and over-expressing PME-1 (+PME-1). FIG. 13A depicts cells stained with DAPI (blue, nuclear marker) and treated with α-PME-1 antibodies to confirm over-expression of PME-1 (compare $A_{ii}$ to $A_i$). FIG. 13B depicts RL95-2 cells treated with α-phospho-ERK ($B_{i, ii}$) and α-ERK ($B_{iii-iv}$) to determine if PME-1 over-expression correlates with increased ERK phosphorylation (compare $B_{ii}$ to $B_i$).

Figure 18A:
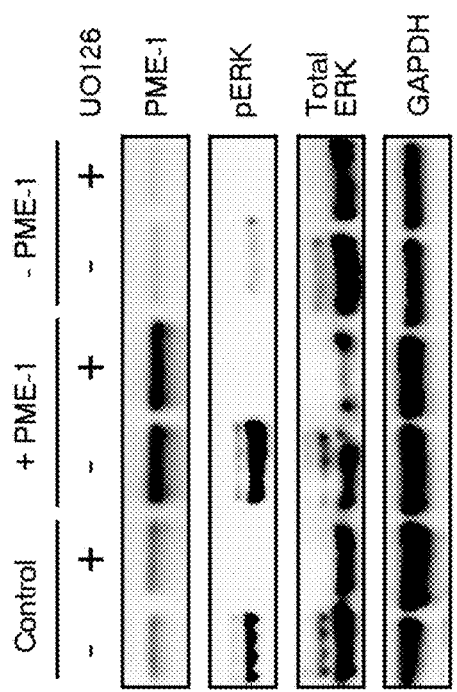

FIG. 18A depicts a Western blot of RL95-2 cells expressing empty vector (control), over-expressing PME-1 (+PME-1) and expressing shRNA to PME-1 (−PME-1). FIG. 14A depicts RL95-2 cells treated with an up-stream inhibitor of ERK phosphorylation (U0126, +) and a vehicle (−). Lysates were probed for PME-1, phospho-ERK, and total ERK levels (GAPDH served as a loading control).

Figure 18B:
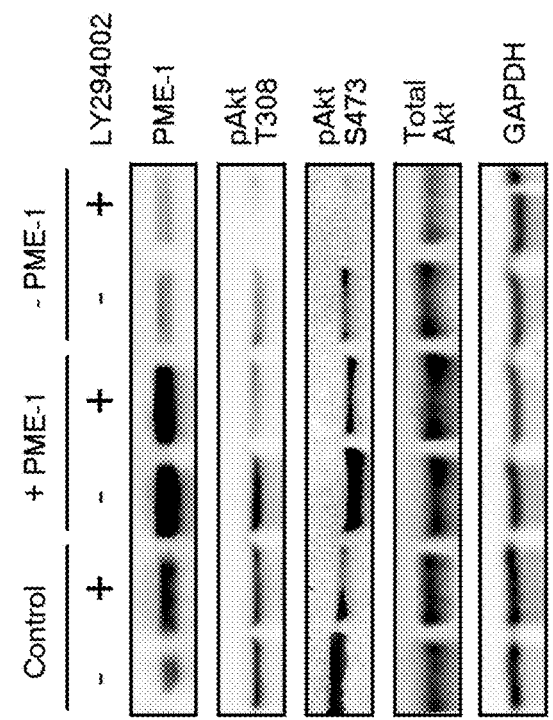

FIG. 18B depicts RL95-2 cells treated with an upstream inhibitor of AKT phosphorylation (LY294002, +) and vehicle (−). Lysates were probed for PME-1 and phosphorylation −AKT at threonine 308 and serine 473 (GAPDH served as a loading control).

Figure 19B:
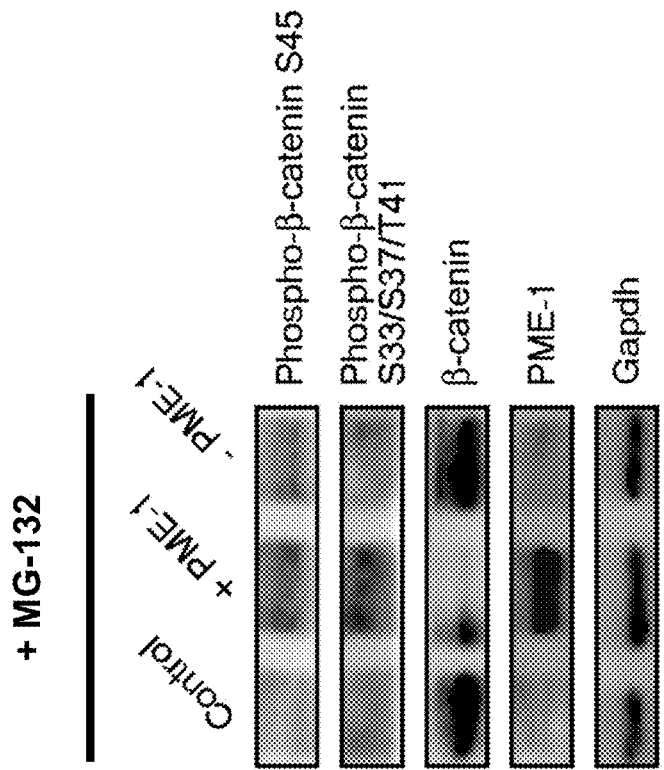
Figure 19A:
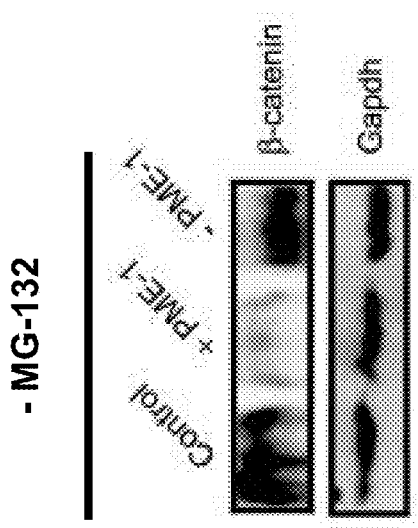

FIG. 19A depicts RL95-2 lysates that were analyzed for total β-catenin levels when PME-1 was over-expressed (+PME-1) and when PME-1 was depleted (−PME-1) in the absence of the proteasome inhibitor, MG-132.

FIG. 19B depicts RL95-2 lysates that were analyzed for β-Catenin at serine 45, 33, 37, and threonine 41 when PME-1 was over-expressed (+PME-1) and when PME-1 was depleted (−PME-1) in the presence of the proteasome inhibitor, MG-132.

Figure 20:
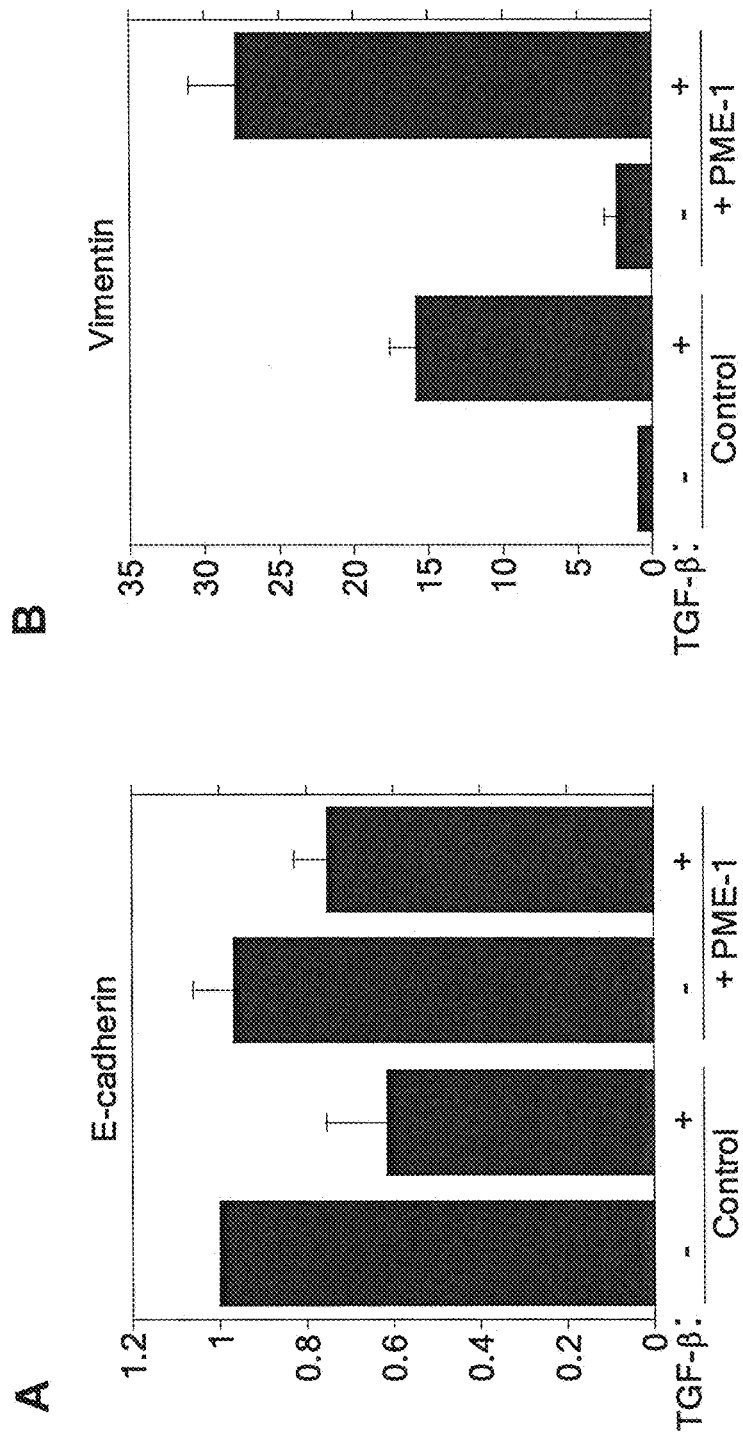
Figure 20:
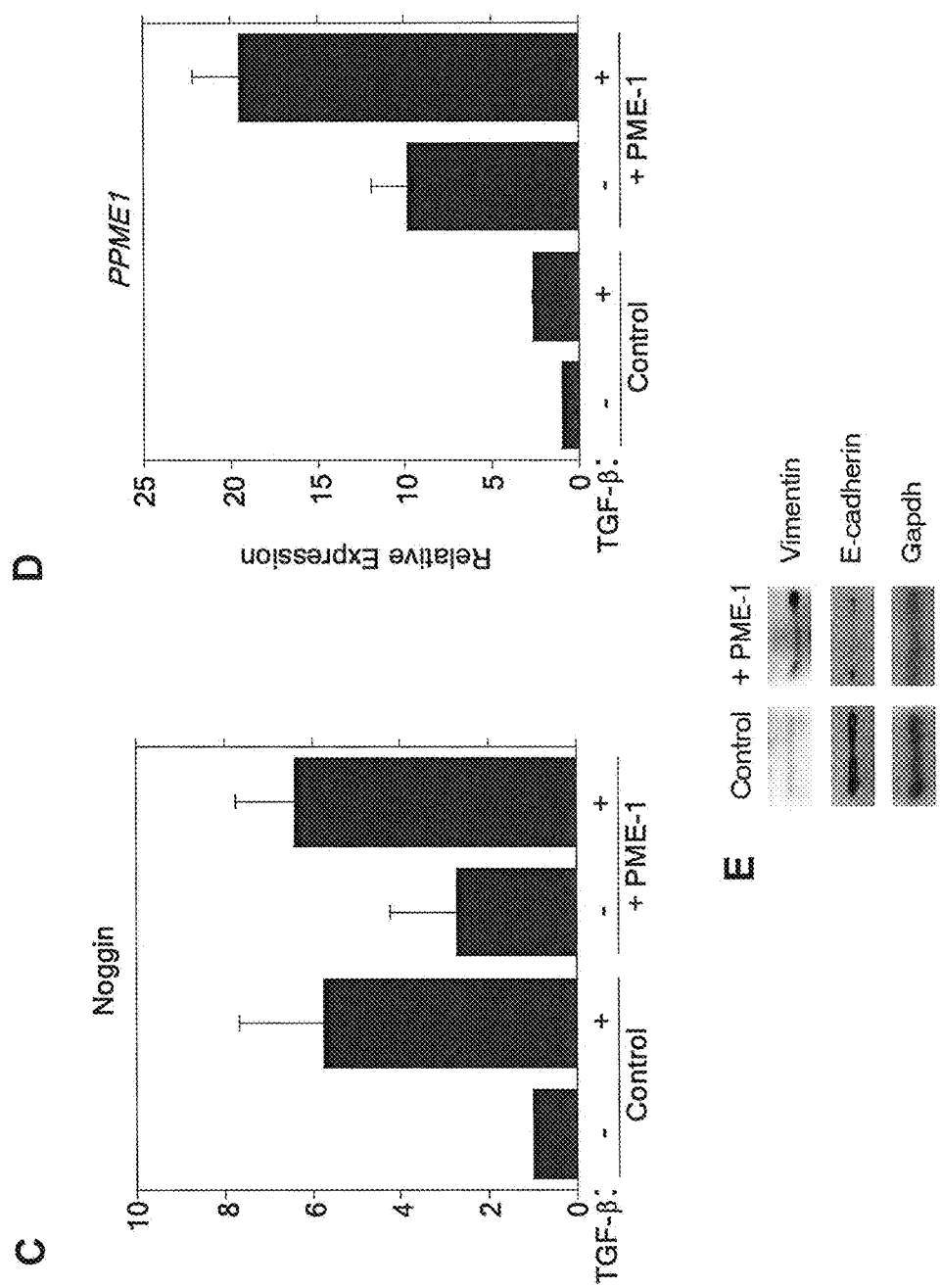

FIG. 20 depicts RL95-2 cells expressing empty vector (Control) and over-expressing PME-1 (+PME-1). The RL95-2 cells were treated with vehicle or TGF-β for 24 hours and were then analyzed by quantitative PCR. Expression of the epithelial marker, E-cadherin (FIG. 20A), the mesenchymal markers, vimentin (FIG. 20B) and Noggin (FIG. 20C); and PPME1 (FIG. 20D) were analyzed. All data was normalized to GAPDH expression (FIG. 20E).

FIGS. 21A-F depict RL95-2 cells stably expressing control vectors (Empty or shSCR), over-expressing PME-1 (+PME-1), or expressing shRNA against PME-1 (shPPME1) (SEQ ID NO: 2). qRT-PCR analysis was completed normalizing the expression of target genes to that of the 18S house-keeping gene.

FIG. 21A shows that PME-1 was over-expressed ~30-fold in +PME-1 cells compared to empty vector.

FIG. 21B shows that PME-1 was knocked down >50% in cells expressing shPPME1 (SEQ ID NO: 2).

FIG. 21C demonstrates that over-expression leads to a significant decrease in expression of the SFRP1 gene.

FIG. 21D shows that depletion of PME-1 with shRNA (SEQ ID NO: 2) leads to a significant increase in SFRP1 expression. SFRP1 is an inhibitor of Wnt signaling.

FIG. 21E demonstrates that over-expression of PME-1 leads to significant increases in expression of WNT3 and WNT3A genes.

FIG. 21F shows that depletion of PME-1 leads to significantly decreased WNT3 and WNT3A expression. WNT3 and WNT3A are activators of Wnt signaling.

FIG. 22 depicts ECC-1 cells that were stably transfected with an empty vector (FLAG), FLAG-tagged PME-1 (over-expression of wild-type PME-1), or FLAG-tagged PME-1 S156A (over-expression of mutated serine (S) 156 to alanine (A), such PME-1 mutant is catalytically inactive). Cells (post-transfection) were collected and cellular protein was extracted. Input depicts the relative expression of each protein in total cell lysate, whereas the elution depicts proteins that were immunoprecipitated with FLAG resin.

Figure 22A:
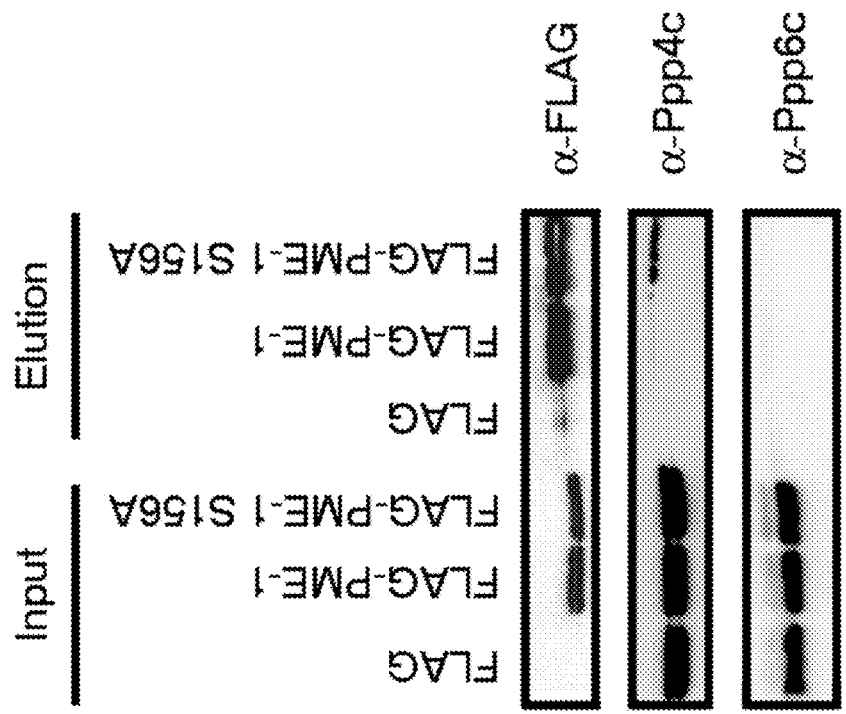

FIG. 22A shows that FLAG-PME-1 and FLAG-PME-1 S156A were immunoprecipitated from the protein lysate. Endogenous Ppp2ca, the alpha isoform of the catalytic subunit of PP2A, binds FLAG-PME-1 (weakly) and the S156A mutant (strongly).

Figure 22B:
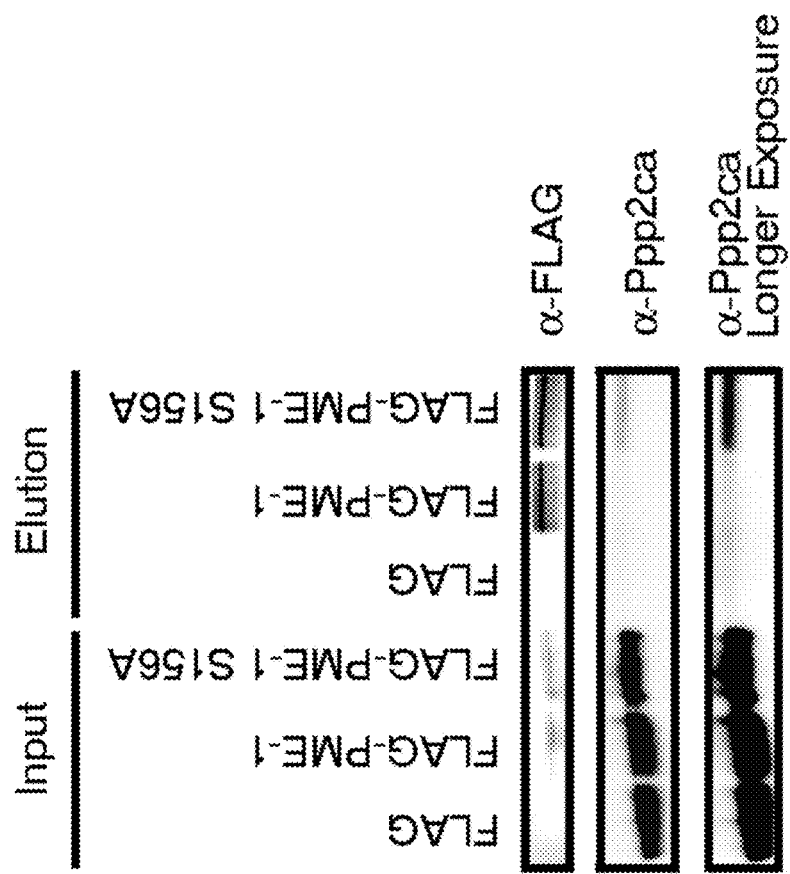

FIG. 22B shows that FLAG-PME-1 and FLAG-PME-1 S156A were immunoprecipitated from the ECC-1 protein lysate. Endogenous Ppp4c, the catalytic subunit of PP4, binds PME-1 (weakly) and PME-1 S156A (strongly). Endogenous Ppp6c, the catalytic subunit of PP6, does not bind to PME-1 or PME-1 S156A.

Figure 23A:
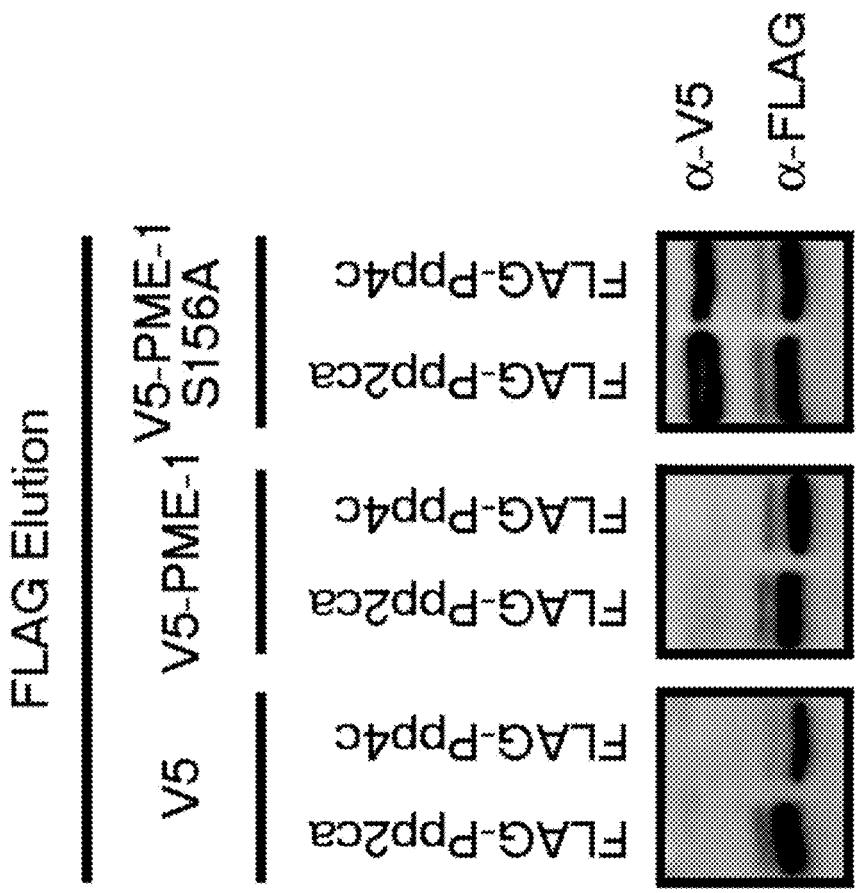
Figure 23B:
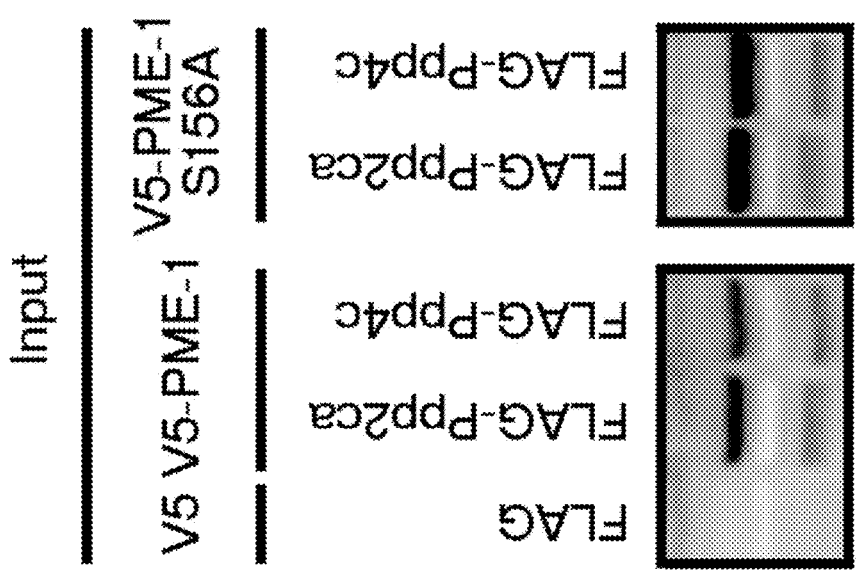

FIGS. 23A-B depict HEK293T cells that were co-transfected with V5 empty vector, V5-PME-1, or V5-PME-1 S156A in combination with FLAG empty vector, FLAG-Ppp2ca, or FLAG-Ppp4c.

FIG. 23A depicts the input demonstrating that wild type V5-PME-1 and V5-PME-1 S156A were equally expressed and that FLAG-Ppp2ca and FLAG-Ppp4c were expressed at a similar level.

FIG. 23B depicts the FLAG elution where Ppp2ca and Ppp4c were immunoprecipitated and similar levels of protein were collected. Western analysis with the α-V5 antibody shows that PME-1 S156A binds more strongly to Ppp2ca over Ppp4c, suggesting that PME-1 has a higher affinity for PP2A than PP4.

Figure 24:
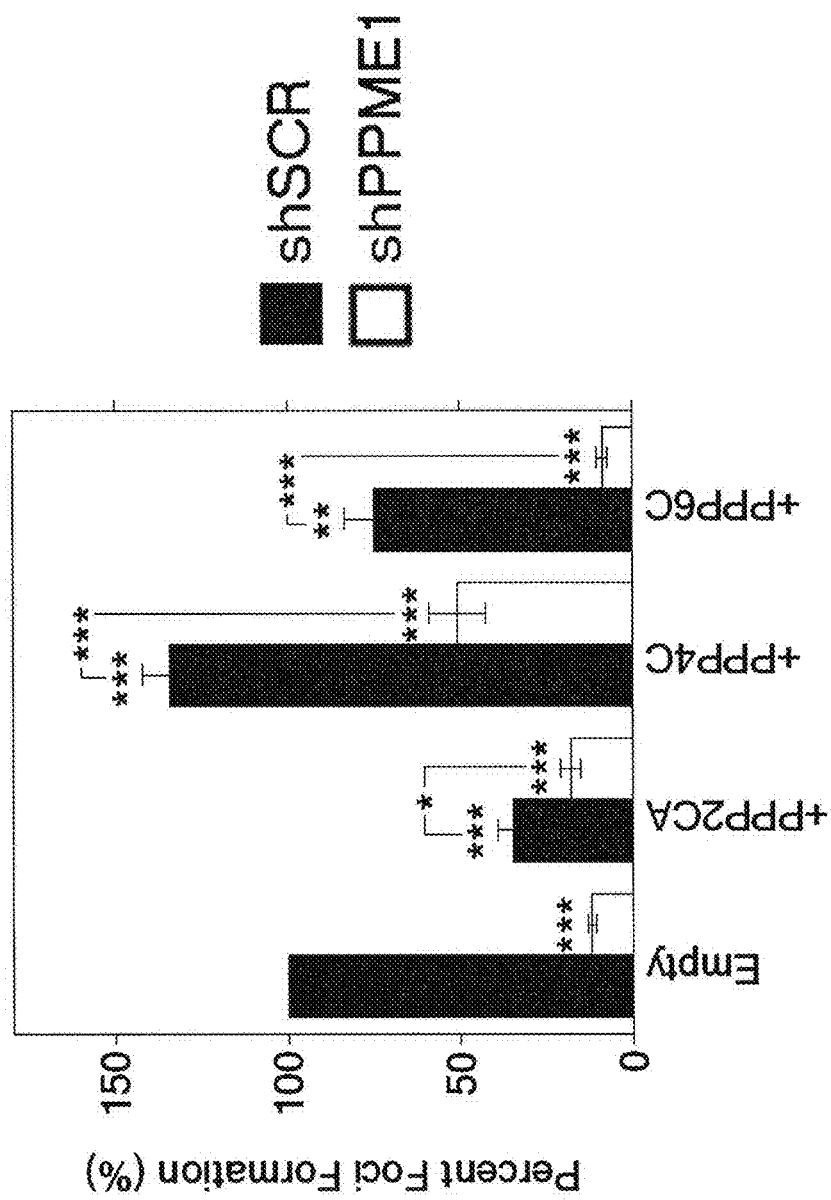

FIG. 24 depicts results from a study in which stable clones of ECC-1 cells expressing non-targeting scrambled shRNA (shSCR, black bars) or shPPME-1 (white bars) (SEQ ID NO: 2) and were then transfected with FLAG empty vector, FLAG-PPP2CA, FLAG-PPP4C, or FLAG-PPP6C. Cells (3,000) were plated and were allowed to grow for 10 days. Colonies were then stained with crystal violet and counted. The control cells expressing shSCR and transfected with empty FLAG vector were normalized to 100% foci formation. PME-1 inhibition via shRNA led to a significant decrease in foci formed regardless of whether PP2A, PP4, or PP6 activity was increased. Averages of 6 experiments are plotted and statistical significance was calculated with the Student's T test, where $*p<0.05$, $p<0.01$, $*p<0.001$.

Figure 25:
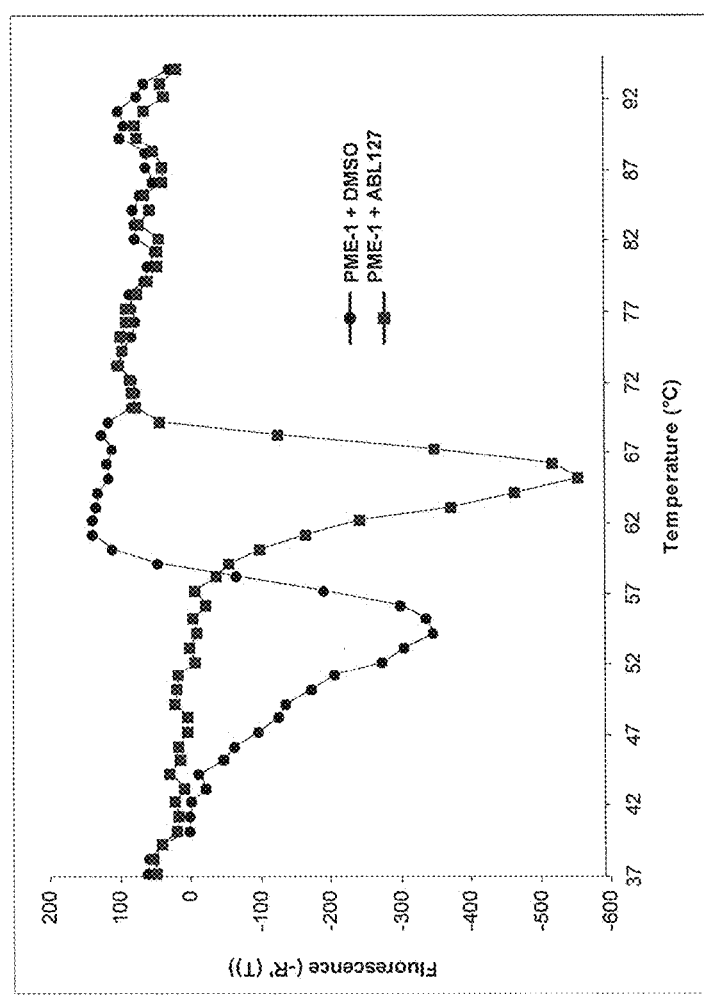

FIG. 25 depicts results from a thermal shift assay in which recombinant PME-1 was incubated with either vehicle (circles) or a covalent inhibitor of PME-1, ABL-127 (squares ((3R)-Dimethyl 3-cyclopentyl-4-oxo-3-phenyl-1,2-diazetidine-1,2,-dicarboxylate, $C_{17}H_{20}N_2O_5$, Sigma cat# SML-0294, Bachovchin, PNAS 108: 6811-6816 (2011)). Dissociation curves demonstrate that the binding of ABL-127 to PME-1 increases the melting temperature (Tm) and the thermal stability of PME-1.

Figure 26:
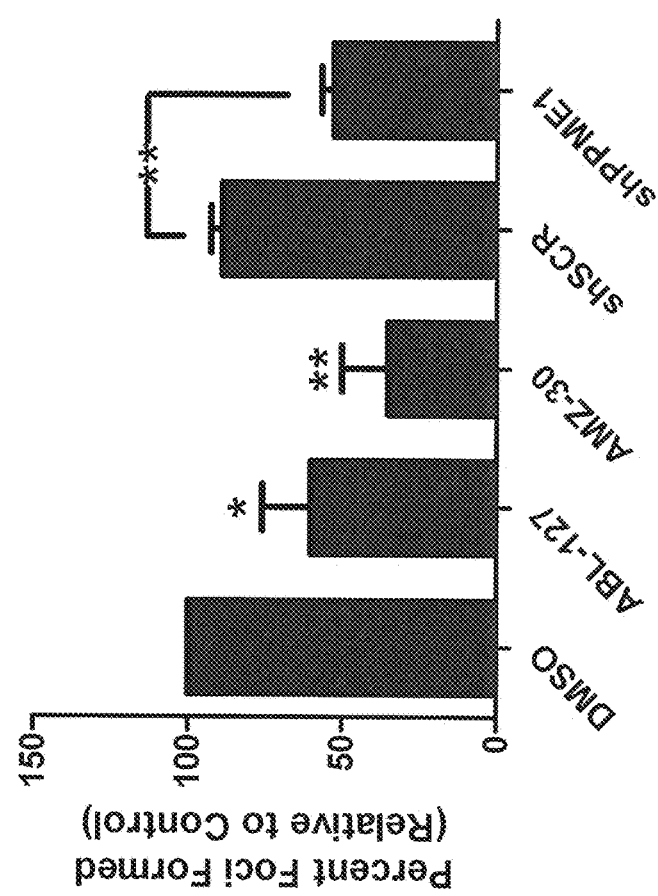

FIG. 26 depicts results from a foci formation assay using DMSO as vehicle and treating Ishikawa cells with the covalent inhibitors ABL-127 (50 nM) or AMZ-30 (25 μM) ((E)-2-(4-Fluorophenylsulfonyl)-3-(1-(3-nitrophenylsulfonyl)-1H-pyrrol-2-yl)-acrylonitrile), $C_{19}H_{13}FN_3O_6S_2$, EMD Millipore cat#539695 and Bachovchin, J. Med. Chem. (2011)) every 2-3 days for a total of 10 days. shSCR and shPPME1 treated cells are used for comparison and were normalized to untreated treated cells (not shown) set to 100%.

Figure 27:
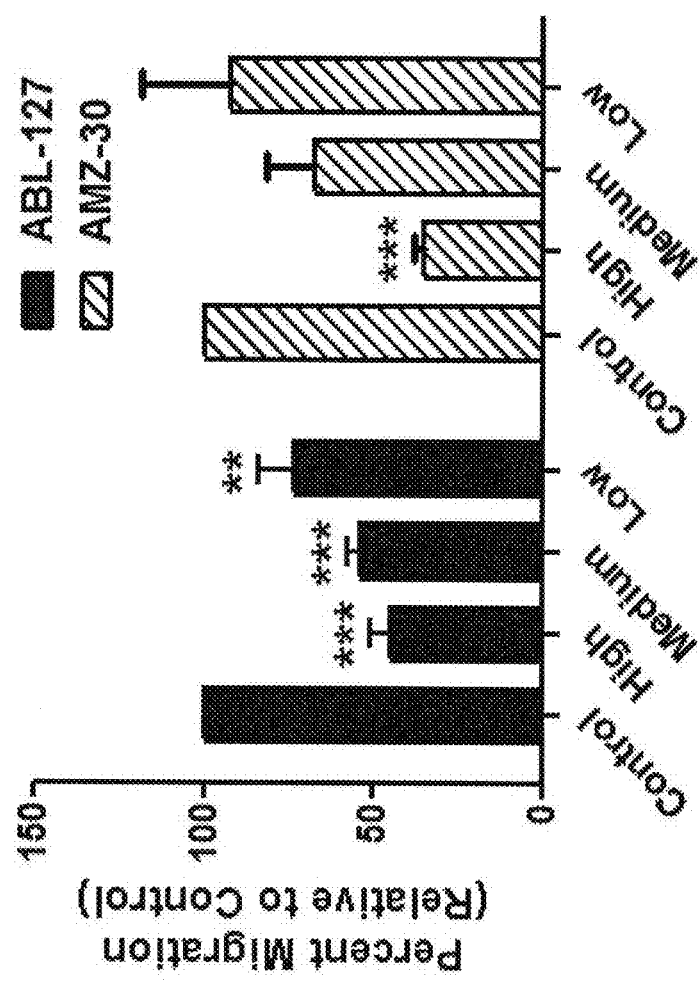

FIG. 27 depicts results from a trans-well migration assay using DMSO as vehicle and treating Ishikawa cells with 50 nM ABL-127 or 20 μM AMZ-30 for 24 hr after synchronizing cells in 0% FBS for 24 hr. Cells migrated through collagen towards the bottom well containing 30% FBS.

FIGS. 28A-D depicts results from a mice xenograft study. $1×10^6$ ECC-1 cells expressing empty vector (control) or over-expressing PME-1 (+PME-1) were injected subcutaneously into the flank of immune-compromised mice (n=7 per group).

FIG. 28A depicts a Western blot of ECC-1 cells prior to injection, confirming levels of PME-1 over-expression when compared to GAPDH.

FIG. 28B depicts the tumor volume developed in the immune-compromised mice over 7 weeks. The tumors were measured (length, y, and width, x) weekly for 7 weeks and the volume of each tumor was calculated using the equation $V=1/2(yx^2)$. The means were plotted with error bars representing SEM and significance was calculated using two-way ANOVA where $p<0.01$, $*p<0.001$.

FIG. 28C depicts representative tumors resected at week 8 (the white bars represent 0.5 cm).

FIG. 28D depicts a graphical representation of the tumors' weights; the line represents the mean tumor weight per group at week 8. Note that two mice from the control group did not form tumors.

Figure 29:
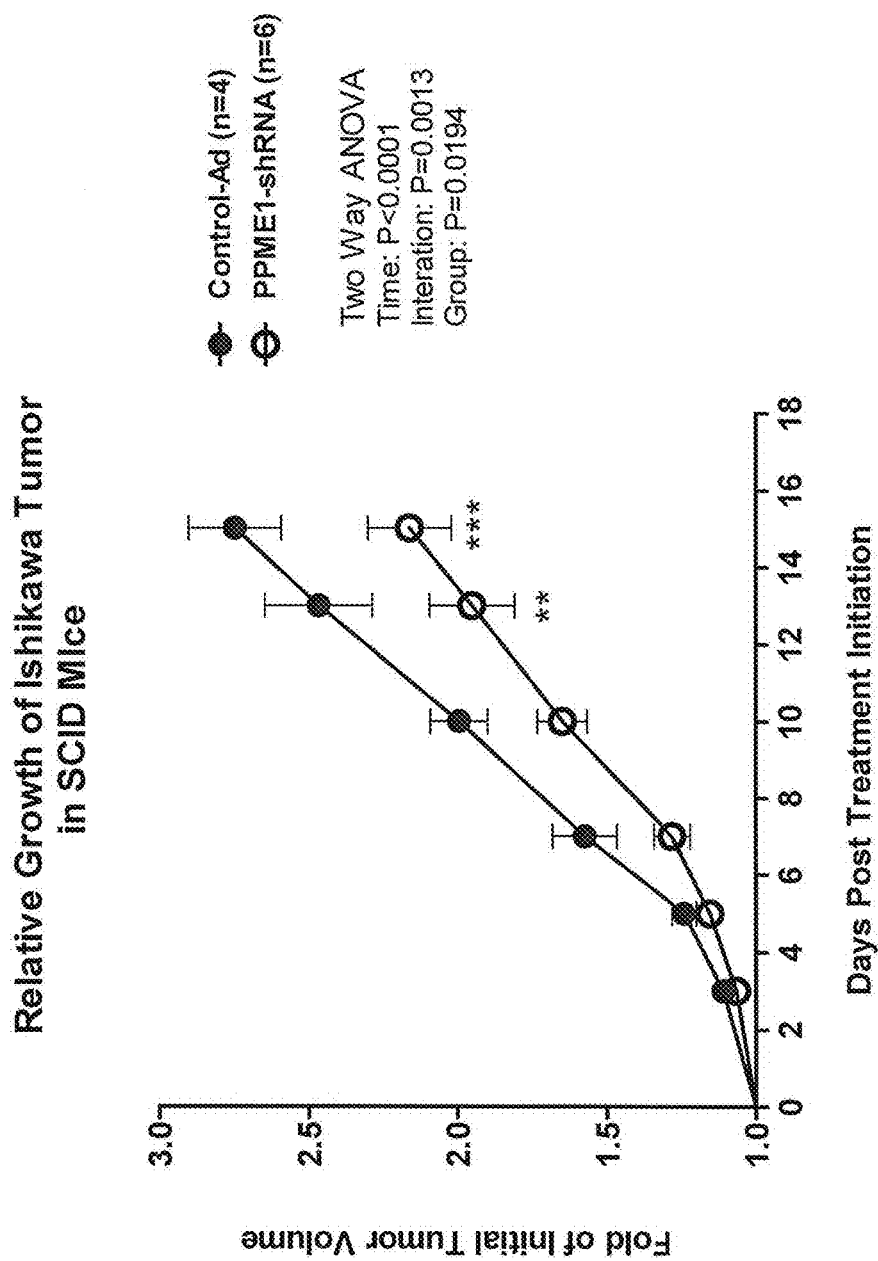

FIG. 29 depicts the results from a mice xenograft study of the tumor volume after treatment with PPME1-shRNA (SEQ ID NO: 3) over the course of 15 days. $5×10^6$ of Ishikawa cells with Matrigel were injected into the flank of female SCID mice and the tumors were allowed to grow to ~400 $mm^3$. Tumors were then injected intratumorally every 3-4 days with $5×10^7$ pfu of adenovirus, delivering either scrambled shRNA (closed circles), or PME-1 shRNA (SEQ ID NO: 3) (open circles). By day 13, depletion of PME-1 significantly decreased tumor volume. Data is shown as fold-change in tumor volume from the start of treatment. The means were plotted with error bars representing SEM. Significance was calculated using two-way ANOVA where $p<0.01$, $*p<0.001$.

Figure 30:
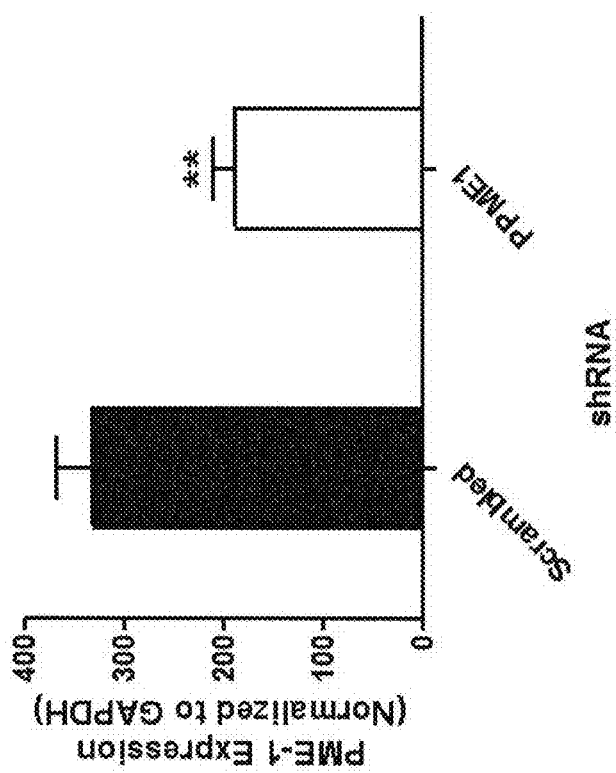

FIG. 30 depicts the graphical representation of the quantification of PME-1 expression obtained from Western Blot analyses of the resulting tumors generated in the xenograft study (FIG. 29). After the xenograph study, the tumors were resected and cut in half. Half the tumors were flash frozen in liquid nitrogen and were used to extract protein to be used in the Western Blot analysis. Densitometry was completed to quantify protein expression when tumors were treated with shRNA against PME-1 (white bar, SEQ ID NO: 3) compared to the control, non-targeting shRNA (black bar). The means were plotted with error bars representing SEM. PME-1 protein levels were normalized to GAPDH and the data was analyzed by the student's t test for significance; where $**p<0.01$.

FIGS. 31A-C depict the immunohistochemistry (IHC) analysis of the resulting tumors from the xenograft study (FIG. 29). At the end of the study, half of the tumors were preserved in formalin and were sectioned for analysis.

FIG. 31A depicts a representative tumor section that was stained with hematoxylin and eosin (H&E staining) and with an anti-PME-1 antibody. It shows a tumor treated with shSCR and stained with α-PME-1.

FIG. 31B depicts a representative tumor section that was stained with hematoxylin and eosin (H&E staining) and with an anti-PME-1 antibody. It shows a tumor treated with shPPME1, or shRNA targeting PME-1 (SEQ ID NO: 3), and then stained with α-PME-1.

FIG. 31C depicts the quantification of the pathologists' score of FIGS. 31A and 31B for PME-1 positivity. The means were plotted with error bars representing SEM.

FIG. 32A depicts IHC analysis to determine the amount of tumor necrosis. Tumor necrosis correlates with tumor cell death and in endometrial cancer. After staining, a pathologist scored the percentage of necrosis for each tumor sample.

FIG. 32B depicts IHC analysis to determine the amount of p53 positivity. High levels of p53 positivity correlate with increased cell proliferation. After staining, a pathologist scored the percentage of p53 positivity for each tumor sample.

FIG. 32C depicts the quantification of the pathology score for tumor necrosis (black bars) and p53 positivity (white bars). The means were plotted with error bars representing SEM. Data was analyzed with the student's t test to determine significance, where $*p<0.05$, $***p<0.001$.

FIG. 33A depicts immunofluorescence (IF) microscopy analysis of the tumor sections from the xenograft study (FIG. 29). These tumor sections were stained with DAPI, a nuclear stain.

FIG. 33B depicts immunofluorescence (IF) microscopy analysis of the tumor sections from the xenograft study (FIG. 29). These tumor sections were stained with terminal deoxynucleotidyl transferase-mediated dUTP nick end-labeling (TUNEL) stain, which stains apoptotic cells.

FIG. 33C depicts immunofluorescence (IF) microscopy analysis of the tumor sections from the xenograft study (FIG. 29). These tumor sections were stained with DAPI, a nuclear stain.

FIG. 33D depicts immunofluorescence (IF) microscopy analysis of the tumor sections from the xenograft study (FIG. 29). These tumor sections were stained with terminal deoxynucleotidyl transferase-mediated dUTP nick end-labeling (TUNEL) stain, which stains apoptotic cells.

FIG. 34A depicts IF microscopic analysis of tumor sections from the xenograft study (FIG. 29) in which slides were stained with the nuclear stain, DAPI.

FIG. 34B depicts IF microscopic analysis of tumor sections from the xenograft study (FIG. 29) in which slides were stained with an anti-PME-1 antibody.

FIG. 34C depicts IF microscopic analysis of tumor sections from the xenograft study (FIG. 29) in which slides were stained with an anti-demethylated PP2A antibody (α-PP2A deMe).

FIG. 34D depicts IF microscopic analysis of tumor sections from the xenograft study (FIG. 29) in which slides were stained with the nuclear stain, DAPI.

FIG. 34E depicts IF microscopic analysis of tumor sections from the xenograft study (FIG. 29) in which slides were stained with an anti-PME-1 antibody.

FIG. 34F depicts IF microscopic analysis of tumor sections from the xenograft study (FIG. 29) in which slides were stained with an anti-demethylated PP2A antibody (α-PP2A deMe). PME-1 demethylates PP2A on leucine 309 and decrease in PME-1 occurred concomitantly with a decrease in demethylated PP2A.

FIG. 35A depicts IF analysis of tumor sections from the xenograft study (FIG. 29). These tumor sections were stained with the nuclear stain, DAPI.

FIG. 35B depicts IF analysis of tumor sections from the xenograft study (FIG. 29). These tumor sections were stained with anti-PP2A L309-Me antibody, which specifically recognizes the active, methylated forms of PP2A.

FIG. 35C depicts IF analysis of tumor sections from the xenograft study (FIG. 29). These tumor sections were stained with the nuclear stain, DAPI.

FIG. 35D depicts IF analysis of tumor sections from the xenograft study (FIG. 29). These tumor sections were stained with anti-PP2A L309-Me antibody, which specifically recognizes the active, methylated forms of PP2A (FIG. 35B, D).

Figure 36:
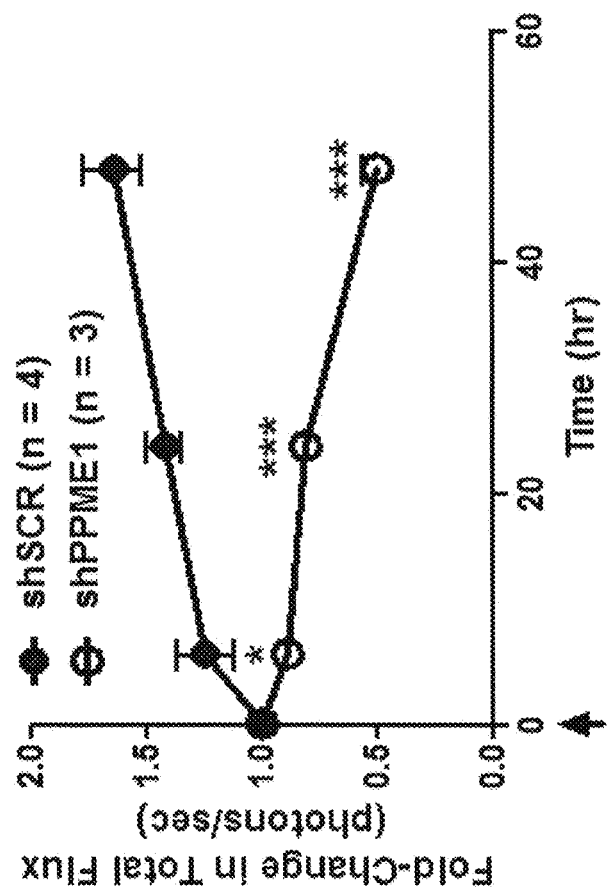

FIG. 36 depicts the graphical results from the another mice xenograft study $2 \times 10^6$ of MDA-MB-23-Luc2 cells with Matrigel were injected into the flank of female SCID mice (severe combined immunodeficiency mice) and the tumors were allowed to grow to ~150 mm³. Tumors were then injected intratumorally $5 \times 10^7$ pfu of adenovirus, delivering either scrambled shRNA (control) (closed circles), or PME-1 shRNA (SEQ ID NO: 3) (open circles). Data is shown as fold-change in total flux (i.e. luciferase signal) from the treatment over 52 hours. The intensity of luciferase signal represents the amount of living cells. The means were plotted with error bars representing SEM and significance was calculated using two-way ANOVA where *$p<0.05$, ***$p<0.001$.

DETAILED DESCRIPTION OF THE INVENTION

The present invention can be better understood from the following description of preferred embodiments, taken in conjunction with the accompanying drawings. It should be apparent to those skilled in the art that the described embodiments of the present invention provided herein are merely exemplary and illustrative and not limiting.

DEFINITIONS

Various terms used throughout this specification shall have the definitions set out herein.

As used herein, the term "A," "T," "C", "G" and "U" refer to adenine, thymine, cytosine, guanine, uracil as a nucleotide base, respectively.

As used herein the term "RNAi" refers to RNA interference. For purposes of this application, RNAi encompasses siRNA and shRNA.

As used herein, the term "siRNA" refers to a small interfering RNA. RNA interference refers to the process of sequence-specific post-transcriptional gene silencing in a cell, an animal or a human mediated by short interfering RNA.

As used herein, the term "shRNA" refers to small hairpin RNA comprised of complimentary sequences that produce a hairpin shape. shRNA is processed within the cell to produce a target sequence that specifically promotes degradation of a specific mRNA (e.g., PPME1 mRNA) via sequence-specific complementary base pairings.

As used herein, the term "shSCR" refers to small hairpin RNA comprised of "scrambled" or "non-targeting" sequences that are designed in such a way that their presence does not affect the mRNA stability of any human gene and therefore no gene expression is affected. shSCR is used as a control.

As used herein, the term "siRNA or shRNA targeted against PME-1" refers to siRNA or shRNA specifically promote degradation of PPME1 mRNA via sequence-specific complementary base pairings.

As used herein, the term "target sequence" refers to a contiguous portion of the nucleotide sequence of an mRNA molecule (e.g., 3-UTR of an mRNA molecule) or the corresponding DNA sequence of a particular gene (i.e., PPME1 gene). The target sequence of a siRNA of the present invention refers to an mRNA sequence of that gene that is targeted by the siRNA by virtue of its complementarity of the anti-sense strand of the siRNA to such sequence and to which the anti-sense strand hybridizes when brought into contact with the mRNA. The mRNA sequence may include the number of nucleotides in the anti-sense strand as well as the number of nucleotides in a single-stranded overhang of the sense strand, if any.

As used herein, the term "complementary" refers to the ability of a first polynucleotide to hybridize with a second polynucleotide.

As used herein, the term "introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

As used herein, the terms "silencing" and "inhibiting the expression of", in as far as they refer to the PPME1 gene refers to at least partial suppression of the expression of the PPME1 gene, as manifested by a reduction of the amount of mRNA transcribed from the PPME1 gene. Alternatively, the degree of inhibition may be given in terms of a reduction of a parameter that is functionally linked to PPME1 gene transcription, e.g. the amount of protein encoded by the PPME1 gene which is secreted by a cell or found in solution after lysis of such cells.

As used herein, the term "PPME1" refers to the PME-1 gene (i.e., the protein phosphatase methylesterase 1 gene), the nucleotide sequence of which is listed under GenBank accession number NM_016147.1, the disclosure of which is incorporated herein by reference.

As used herein, the term "PME-1" refers to the protein that is translated from the PPME1 gene and is a demethylase (also known as a methylesterase) that removes a methyl group post-translational modification from another protein.

As used herein, the term "demethylase" or "methylesterase" refers to a protein capable of removing a methyl group (or demethylating) another protein.

As used herein, the term "protein phosphatase 2A (PP2A)" refers to a protein complex that is capable of removing a phosphate group from another protein. PP2A is comprised of two to three different proteins. The core complex is comprised of a catalytic subunit and a scaffolding subunit. The addition of a regulatory subunit targets the complex to a specific substrate.

As used herein, the term "metastasis" refers to cancer cells migrating away from a solid tumor and the establishment of a new tumor in a secondary site.

As used herein, the term "RL95-2" and "ECC-1" and "Ishikawa" refer to human endometrial cancer cell lines that are highly aggressive and capable of metastasis.

As used herein, the term "KLE" refers to a human endometrial cancer cell line that is not highly aggressive.

As used herein, the term "End1" refers to a human immortalized endocervical cell line.

As used herein, the term "MDA-MB-231Luc2" refers to a human triple negative breast cancer cell line. This cell line stably expresses luciferase so that cell growth can be measured by monitoring changes in fluorescence.

As used herein, the term "WNT3" and "WNT3A" refer to related members of the Wingless Type MMTV Integration site family (WNT) members of proteins that bind to and activate frizzled receptors that promotes increased gene expression of genes related to cell proliferation and epithelial to mesenchymal transition and metastasis. Wnt proteins activate this pathway and are commonly expressed to higher levels in cancers.

As used herein, the term "SFRP1" refers to secreted frizzled-like protein 1, which is binds to Wnt and Frizzled proteins and inhibits the Wnt signaling pathway.

As used herein, the term "foci" and "foci formation" refer to an assay in which a known number of cells are plated in a tissue culture dish and are allowed to grow for a defined number of days and form collections of cells—or foci—that can be stained and counted to quantify cell growth.

As used herein, the term "BrdU assay" refers to an assay in which cells are incubated with bromodeoxyuridine (BrdU), which is incorporated into newly synthesized DNA. BrdU can be detected with an antibody to directly measure the rate of cellular proliferation.

As used herein, the term "endometrial cancer" refers to the cancer that starts at the endometrium, the tissue lining of the uterus. Endometrial cancer is also referred to as uterine cancer.

As used herein, the term "stage I" refers to endometrial cancer that is confined to the uterus.

As used herein, the term "stage II" refers to endometrial cancer that has spread from the uterus to the cervix (the lower part of the uterus) but has not spread outside the uterus.

As used herein, the term "stage III" refers to endometrial cancer that has spread to one or more of the following: the outermost layer of the uterus (uterine serosa), the tissue just beyond the uterus (i.e. adnexa—tissues on either side of the uterus) or the ovary.

As used herein, the term "FIGO grading" refers to the grading system for carcinoma of the endometrium developed by the International Federation of Gynecology and Obstetrics. The FIGO system is most commonly used and is the required grading system for carcinoma of the endometrium under the College of American Pathologists' protocol. FIGO grading excludes serous or clear cells, which are considered high grade (grade 3). Alternative grading divides endometrioid tumors into low grade or high grade based on solid growth (50% or less vs. 50% or more), pattern of invasion (infiltrative vs. expansive) and presence of tumor cell necrosis (yes vs. no). A patient will be diagnosed with high grade if the tumors cells have 2 of these features.

As used herein, the term "grade 1" or "FIGO Grade 1" refers to endometrial cells that resemble microglandular hyperplasia and are composed primarily of well formed glands, having <5% nonsquamous solid component.

As used herein, the term "grade 2" or "FIGO Grade 2" refers to endometrial cells that are composed of between 6% and 50% nonsquamous solid components.

As used herein, the term "grade 3" or "FIGO Grade 3" refers to endometrial cells that have more than 50% nonsquamous solid component, lack well formed glands, which differentiates it from serous endometrial carcinoma. As used herein, the term "cell proliferation" or "cell growth" refers to the rate at which cells divide and complete the cell cycle.

As used herein, the term "triple negative breast cancer" or "TNBC" refers to cancer that starts in the breast tissue and does not express estrogen receptor, progesterone receptor, or human epidermal growth factor receptor type 2 (HER2/neu).

As used herein, the term "epithelial to mesenchymal transition" or "EMT" refers to cells that are capable of migration due to loss of cell-to-cell contact, changes in cell morphology, loss of epithelial markers, such as E-cadherin, and acquisition of mesenchymal markers, such as vimentin.

As used herein, the term "E-cadherin" refers to a protein that is a member of the cadherin superfamily. E-cadherin is a calcium-dependent adhesion glycoprotein and plays a major role in maintaining cell-to-cell contacts. Loss of E-cadherin is a hallmark of EMT.

As used herein, the term "P-cadherin" refers to a protein that is a member of the cadherin superfamily and is a transmembrane glycoprotein. Increases in P-cadherin expression has been correlated with increased aggressivity of endometrial cancers.

As used herein, the term "vimentin" refers to a protein that is a member of the intermediate filament family and is part of the cytoskeleton. Vimentin plays a role in maintenance of cell shape and organizes other proteins involved in cell attachment, migration, and cell signaling. Increased vimentin is a hallmark of EMT.

As used herein, the term "Noggin" is a secreted protein that binds and inactivates members of the TGF-β family of signaling proteins. Increased noggin is a marker for EMT.

As used herein, the term "TGF-β" or "transforming growth factor β" protein is a cytokine that regulates cell proliferation, differentiation, adhesion, and migration and is commonly increased in cancer cells. Addition of TGF-β to cells in culture can promote EMT.

As used herein, the term "β-catenin" refers to a protein that is part of a complex of proteins that are important for maintaining cell-to-cell contacts and may transmit contact inhibition signals to stop cell growth.

As used herein, the term "epithelial" refers to ordered and differentiated cells that line the inner and outer surfaces of the body.

As used herein, the term "inesenchymal" refers to cells that are less differentiated and have the ability to differentiate into different types of cells or migrate.

As used herein, the term "extracellular signal-regulated kinase" or "ERK" refers to a protein that is a mitogen-activated protein kinase and signals through the phosphorylation and activation of other proteins, such as transcription factors, to promote cell proliferation. ERK activity is often increased in cancer.

As used herein, the term "Akt" is a protein kinase that is part of a cellular signaling cascade that promotes cell proliferation. Phosphorylated Akt is active and promotes cell proliferation. Akt activity is often increased in cancer.

As used herein, the term "apoptosis" is a natural process of cellular suicide that is marked by the fragmentation of DNA and can occur due to accumulation of DNA damage.

As used herein, the term "senescence" refers to the process by which cells exit the cell cycle and cease to proliferate. The term "cell cycle" refers to the process by which a cell divides to produce two identical cells. Cells undergo DNA replication, two periods of growth, and enter mitosis.

As used herein, the term "mitosis" refers to the cellular process in which a cell divides to produce two, nearly identical cells.

As used herein, the terms "attenuate", "treat" and "treatment" refer to relief from or alleviation of pathological processes mediated by PME-1 expression. In other words, relief from or alleviate at least one symptom associated with such condition, or to slow or reverse the progression of such condition.

The term "inhibit gene expression" refers to the use of siRNA or shRNA molecule to down regulate the expression of target gene PME-1 mRNA, which thereby leads to reduced expression of the PME-1 gene.

As used herein, the term "quantitative PCR" refers to the quantitative polymerase chain reaction. Quantitative PCR is a means for quantifying the amount of template DNA present in the original mixture, usually achieved by the addition of a known amount of a target sequence that is amplified by the same primer set but can be differentiated, usually by size, at the end of the reaction.

As used herein, the term "real-time PCR" refers to the real-time polymerase chain reaction. Real-time PCR is a method for the detection and quantification of an amplified PCR product based on a fluorescent reporter dye; the fluorescent signal increases in direct proportion to the amount of PCR product produced and is monitored at each cycle, 'in real time', such that the time point at which the first significant increase in the amount of PCR product correlates with the initial amount of target template.

As used herein, the term "quantitative reverse transcription PCR" (i.e., "qRT-PCR") refers to a quantitative polymerase chain reaction (qPCR) used to detect mRNA expression levels. The qRT-PCR contains a first step wherein the mRNA molecules are converted to complementary DNA molecules (cDNAs) by reverse transcription enzyme in a "reverse transcription" reaction (RT). The qRT-PCR contains a second step wherein the expression levels of mRNA are quantified.

As used herein, the term "Ct score" or "Cycle threshold" refers to the amount of PCR cycles required for the accumulation of a fluorescent signal to reach the threshold level or the amount of PCR cycles required to surpass background levels As used herein, the term "delta Ct" refers to the difference in Ct values when the Ct value for the normalizer gene (one that should not change across experimental conditions, i.e. 18S) is subtracted from Ct value for the gene of interest.

As used herein, the term "pharmaceutical composition" comprises a pharmacologically effective amount of a RNAi and a pharmaceutically acceptable carrier.

As used herein, the term "pharmaceutically acceptable carrier" refers to a carrier for administration of a therapeutic agent.

As used herein, the term "effective amount" refers to an amount that provides a therapeutic benefit in the treatment, prevention, or management of pathological processes.

As used herein, the term "DAPI" or "4',6-diamidino-2-phenylindole" refers to a fluorescent DNA binding stain used in fluorescence microscopy that binds strongly to A-T rich regions in DNA. DAPI can pass through an intact cell membrane to stain both live and fixed cells.

The present invention provides a novel biomarker for detection of endometrial cancer. Specifically, the present inventors discovered the expression level of PME-1 correlates with the endometrial cancer development. More specifically, the increased expression level of PME-1 is associated with higher grades of endometrial cancer (i.e., grade II and grade III). The present application discloses the use of PME-1 as a biomarker to detect or diagnose endometrial cancer in women.

Using cell cultures of endometrial cells, the present inventors found that the expression levels of PME-1 (including both protein and mRNA) are elevated in these cells when compared to their counterparts. The present inventors extended the in vitro finding to clinical application. Using clinical samples obtained from women who suffered from various stages/grades of endometrial cancer, the present inventors demonstrated that PME-1 expression levels (protein or mRNA) increase in endometrial tissues derived from patients who suffer from endometrial cancer as compared to endometrial tissues derived from control patients who do not have endometrial cancer. The expression levels of PME-1 (either protein or mRNA) significantly increase throughout higher cancer stages (i.e., stage II, and stage III of endometrial cancer).

The present invention provides a diagnostic assay having a high sensitivity and specificity for detecting endometrial cancer occurrence in a woman suspected of having endometrial cancer. ROC analysis demonstrates that the sensitivity of the present assay is 80.77% and the specificity is 96.15%. PPME1 mRNA expression with a cut-off of 8.14 (determined using Prism software) demonstrates a 95.5% positive predictive value (PPV) and an 83.3% negative predictive value (NPV).

There has been a long-felt need for identifying a novel biomarker that would permit early detection and diagnosis of endometrial cancer diseases. Little is known about biomarkers that may serve for the detection of endometrial cancer.

The present inventors cured the prior art deficiency and fulfilled the long-felt need in this medical area. The present inventors surprisingly discovered PME-1 as a biomarker for detection of endometrial diseases in humans. Protein methylesterase-1 (PME-1) is a specific methylesterase and removes the methyl group from the C-terminal leucine residue on the C subunit of the PP2A that has tumor suppressor activity. The methyl post-translational modification is believed to increase the tumor suppressor activity of PP2A, a molecule that is involved in numerous cellular processes, including signal transduction pathways that regulate mitogenic and survival signals. In yeast, disruption of methyltransferase for methylating PP2A leads to severe growth defects. In mice, PME-1 targeted gene disruption causes perinatal lethality and a near complete loss of demethylated PP2A in most tissues, suggesting PME-1 may play a role in cellular signaling. Because certain forms of PP2A are known to stabilize p53 activity or decrease the activity of pro-cell growth signaling pathways, it is possible that PME-1 may contribute to endometrial cancer initiation and progression. The exact role PME-1 in cancer progression remains unclear, let alone PME-1's role in endometrial cancer and TNBC.

To the best of the present inventors' knowledge, PME-1 expression has been reported to significantly correlate with disease progression in human astrocytic gliomas. The present invention represents the first report linking PME-1 expression with endometrial cancer and triple negative breast cancer. The present invention provides a novel finding that PME-1 is a good molecular biomarker for detection of endometrial cancer. The present finding is unexpected because the present assay employing PME-1 expression provides a high sensitivity and specificity.

The present invention also provides a novel finding that the silencing of PME-1 expression provides treatment for both endometrial cancer and TNBC.

Collection and Preparation Biological Samples

Biological samples of the endometrium in humans (including cells or tissues) can be conveniently collected by methods known in the art. Usually, endometrial tissues (or cells thereof) can be harvested by trained medical staffs or physicians, under sterile environment. Endometrial tissues or cells may be taken, for example, by scrapes, smears, or swabs. Swabs may include but are not limited to, spatulas, brushes, or brooms. Other means include punch biopsy, endocervical curettage, conization, resection of tumor samples, tissue samples prepared by endoscopic means, needle-biopsies of organs, and the like. After harvested from patients, biological samples may be immediately frozen (under liquid nitrogen) or put into a storage, or transportation solution to preserve sample integrity. Such solutions are known in the art and commercially available, for example, UTM-RT transport medium (Copan Diagnostic, Inc, Corona, Calif.), Multitrans Culture Collection and Transport System (Starplex Scientific, Ontario, Conn.), ThinPrep® Paptest Preservcyt® Solution (Cytyc Corp., Boxborough, Mass.) and the like.

Sample Preparation: Protein Extraction

After collection, tissue samples are prepared prior to detection of biomarkers. Sample preparation includes isolation of protein or nucleic acids (e.g., mRNA). These isolation procedures involve separation of cellular protein or nucleic acids from insoluble components (e.g., cytoskeleton) and cellular membranes.

In one embodiment, endometrial tissues or cells are treated with a lysis buffer solution prior to isolation of protein or nucleic acids. A lysis buffer solution is designed to lyse tissues, cells, lipids and other biomolecules potentially present in the raw tissue samples. Generally, a lysis buffer of the present invention may contain a chemical agent that includes one or more of the following ingredients: (i) chaotropic agents (e.g., urea, guanidine thiocyanide, or formamide); (ii) anionic detergents (e.g., SDS, N-lauryl sarcosine, sodium deoxycholate, olefine sulphates and sulphonates, alkyl isethionates, or sucrose esters); (iii) cationic detergents (e.g., cetyl trimethylammonium chloride); (iv) non-ionic detergents (e.g., Tween®-20, polyethylene glycol sorbitan monolaurate, nonidet P-40, Triton® X-100, NP-40, N-octyl-glucoside); (v) amphoteric detergents (e.g., CHAPS, 3-dodecyl-dimethylammonio-propane-1-sulfonate, lauryldimethylamine oxide); or (vi) alkali hydroxides (e.g., sodium hydroxide or potassium hydroxide). Suitable liquids that can solubilize the cellular components of biological samples are regarded as a lysis buffer for purposes of this application.

In another embodiment, a lysis buffer may contain additional substances to enhance the properties of the solvent in a lysis buffer (e.g., prevent degradation of protein or nucleic acid components within the raw biological samples). Such components may include proteinase inhibitors, RNAse inhibitors, DNAse inhibitors, and the like. Proteinase inhibitors include but not limited to inhibitors against serine proteinases, cysteine proteinases, aspartic proteinases, metallic proteinases, acidic proteinases, alkaline proteinases or neutral proteinases. RNAse inhibitors include common commercially available inhibitors such as SUPERase.In™ (Ambion, Inc. Austin, Tx), RNAse Zap® (Ambion, Inc. Austin, Tx), Qiagen RNase inhibitor (Valencia, Calif.), and the like.

Sample Preparation: Nucleic Acid Extraction

Nucleic acids, such as mRNA, can be conveniently extracted from biological samples obtained from endometrium (i.e., endometrial tissues) using standard extraction methods that are known in the art. Standard extraction methods include the use of a chemical agent such as guanidinium thiocyanate, phenol-chloroform extraction, guanidine-based extraction, and the like. Commercial nucleic acid extraction kits may be employed. For example, RNeasy Fibrous Tissue Mini Kit from Qiagen (Valencia, Calif.) and RNAimage Kit from GenHunter Corporation (USA).

Detection of Protein Expression Level

After protein extraction, expression level of PME-1 protein in the biological samples can be determined using standard assays that are known in the art. These assays include but not limited to Western blot analysis, ELISA, radioimmunoassay, fluoroimmunoassay, immunohistochemistry assay, dot-blot assay, and the like. In a preferred embodiment, expression level of biomarkers may be detected by Western blot analysis. In another preferred embodiment, PME-1 protein expression may be determined by Western blot analysis.

Western Blot

After cellular proteins are extracted or isolated from the biological samples (e.g., endometrial tissues), the cellular proteins are separated using SDS-PAGE gel electrophoresis. The conditions for SDS-PAGE gel electrophoresis can be conveniently optimized by one skilled in the art.

Protein biomarkers in the gels can then be transferred onto a surface such as nitrocellulose paper, nylon membrane, PVDF membrane and the like. The conditions for protein transfer after SDS-PAGE gel electrophoresis may be optimized by one skilled in the art. Preferably, a PVDF membrane is used.

To detect the biomarker proteins, a first antibody specific for the PME-1 protein is employed. Bound cellular proteins (e.g., 15-100 μg) on the membrane are incubated with a first antibody in a solution. An optimized first antibody concentration (e.g., 0.2-2 μg/mL) may be used. Incubation conditions may be optimized to maximize binding of the first antibody with the bound biomarker proteins. For example, 1 μg/mL of the first antibody is used and incubation time is 1-6 hours. Preferably, the incubation time is 2 hours. The first antibody may either be a monoclonal antibody or polyclonal antibody. Antibodies against the various protein biomarkers can be prepared using standard protocols or obtained from commercial sources. Techniques for preparing mouse monoclonal antibodies or goat or rabbit polyclonal antibodies (or fragments thereof) are well known in the art. Optionally, the membrane is incubated with a blocking solution before the incubation with the first antibody. The blocking solution may include agents that reduce non-specific binding of antibody. An exemplary blocking solution may include 5% skim milk in PBST (Phosphate Buffer Solution containing 0.1% Tween-20).

After the incubation with the first antibody, the unbound antibody is removed by washing. An exemplary washing solution includes PBST. Protein biomarker-first antibody complex can be detected by incubation with a second antibody that is specific for the first antibody. The second antibody may be a monoclonal antibody or a polyclonal antibody (e.g., mouse, rabbit, or goat). The second antibody may carry a label which may be a directly detectable label or may be a component of a signal-generating system. Preferably, the second antibody is a goat anti-rabbit antibody or goat anti-mouse antibody that is labeled with a peroxidase. Such labeled antibodies and systems are well known in the art.

Direct detectable label or signal-generating systems are well known in the field of immunoassay. Labeling of a second antibody with a detectable label or a component of a signal-generating system may be carried out by techniques well known in the art. Examples of direct labels include radioactive labels, enzymes, fluorescent and chemiluminescent substances. Radioactive labels include $^{124}$I, $^{125}$I, $^{128}$I, $^{131}$I, and the like. A fluorescent label includes fluorescein, rhodamine, rhodamine derivatives, and the like. Chemiluminescent substances include ECL chemiluminescent.

ELISA

In another embodiment, detection and quantification of PME-1 protein biomarker is determined by ELISA.

In a typical ELISA, a first antibody is immobilized onto a solid surface. Immobilization of the first antibody may be performed on any inert support useful in immunological assays. Examples of inert support include sephadex beads, polyethylene plates, polypropylene plates, polystyrene plates, and the like. In one embodiment, the first antibody is immobilized by coating the antibody on a microtiter plate. In another embodiment, the microtiter plate is a microtest 96-well ELISA plate, such as those sold under the name Nunc Maxisorb or Immulon.

The first antibody is an antibody specific (to bind or to recognize) the protein biomarkers of interest. The first antibody may either be a monoclonal antibody, polyclonal antibody, or a fragment thereof. The first antibody may be acquired via commercial sources, or prepared by standard protocols well known in the art. A solid surface includes a 96-well plate.

Protein biomarkers present in a biological sample are captured by the immobilized first antibody. To do so, a protein extract from biological samples is incubated with the immobilized first antibody. Conditions for incubation can be optimized to maximize the formation of protein biomarker-first antibody complex. Preferably, an incubation time of 2-8 hours and a temperature of 25° C. may be used. Unbound first antibody is removed by washing.

To detect the formation of protein biomarker-first antibody complex, a second antibody is used. The second antibody may either be a monoclonal antibody or polyclonal antibody. Preferably, the second antibody is a polyclonal antibody, derived from goat or rabbit. Preparation of the second antibody is in accordance with established protocol or commercially available. Incubation of the second antibody can conveniently be optimized to maximize the binding. Preferably, an incubation time of 2-8 hours and a temperature of 25° C. may be used. Unbound second antibody is easily removed by washing. The second antibody is either directly labeled or conjugated with a signal-generating system.

The methods of detecting the presence of a directly labeled second antibody or a second antibody conjugated with a signal-generating system are well known to those of skill in the art. Suitable direct labels include moieties such as fluorophores, radioactive labels, and the like. Examples of radioactive labels include but not limited to $^{32}$P, $^{14}$C, $^{125}$I, $^{3}$H, and $^{131}$I. Examples of fluorophores include but not limited to fluorescein, rhodamine, and the like.

The second antibody may conveniently be conjugated to a signal-generating system such as an enzyme. Exemplary enzymes include horseradish peroxidase (HRP), alkaline phosphatase, and the like. The conjugation of an enzyme to the second antibody is a standard manipulative procedure for one of ordinary skill in immunoassay techniques. (See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166). Detection of the presence of second antibody can be achieved simply by adding a substrate to the enzyme. The methodology of such enzyme-substrate interaction is well within one skilled in the art's capability.

Detection of mRNA Expression Level.

In one embodiment, the present invention is directed to the discovery that PME-1 protein biomarker is elevated during the pathogenesis of endometrial cancer. In another embodiment, endometrial cancer biomarkers increase their steady-state mRNA expression levels. Detection of mRNA expression levels for PME-1 gene includes standard mRNA quantitation assays that are well-known in the art. These assays include but not limited to qRT-PCR, Northern blot analysis, RNase protection assay, and the like.

In one preferred embodiment, the present invention provides the use of qRT-PCR to detect the expression level of endometrial cancer biomarkers. qRT-PCR (quantitative reverse transcription-polymerase chain reaction) is a sensitive technique for mRNA detection and quantitation. Compared to Northern blot analysis and RNase protection assay, qRT-PCR can be used to quantify mRNA levels from much smaller samples.

Real-time polymerase chain reaction, also called quantitative real time polymerase chain reaction (Q-PCR/qPCR), is used to amplify and simultaneously quantify a targeted DNA molecule. It enables both detection and quantification (as absolute number of copies or relative amount when normalized to DNA input or additional normalizing genes)

of one or more specific sequences in a DNA sample. Currently at least four (4) different chemistries, TaqMan® (Applied Biosystems, Foster City, Calif.), Molecular Beacons, Scorpions® and SYBR® Green (Molecular Probes), are available for real-time PCR.

All of these chemistries allow detection of PCR products via the generation of a fluorescent signal. TaqMan probes, Molecular Beacons and Scorpions depend on Förster Resonance Energy Transfer (FRET) to generate the fluorescence signal via the coupling of a fluorogenic dye molecule and a quencher moiety to the same or different oligonucleotide substrates. SYBR Green is a fluorogenic dye that exhibits little fluorescence when in solution, but emits a strong fluorescent signal upon binding to double-stranded DNA.

Two common methods for detection of products in real-time PCR are: (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary DNA target.

Real-time PCR, when combined with reverse transcription, can be used to quantify messenger RNA (mRNA) in cells or tissues. An initial step in the reverse transcription PCR amplification is the synthesis of a DNA copy (i.e., cDNA) of the region to be amplified. Reverse transcription can be carried out as a separate step, or in a homogeneous reverse transcription-polymerase chain reaction (RT-PCR), a modification of the polymerase chain reaction for amplifying RNA. Reverse transcriptases suitable for synthesizing a cDNA from the RNA template are well known.

Following the cDNA synthesis, methods suitable for PCR amplification of ribonucleic acids are known in the art (See, Romero and Rotbart in Diagnostic Molecular Biology: Principles and Applications pp. 401-406). PCR reagents and protocols are also available from commercial vendors, such as Roche Molecular Systems. PCR can be performed using an automated process with a PCR machine.

Primer sets used in the present qRT-PCR reactions for various biomarkers may be prepared or obtained through commercial sources. For purposes of this application, the primer sets used in this invention include primers ordered from Life Technologies (Assay ID, HS00211693_m1) (Grand Island, N.Y.).

The primers used in the PCR amplification preferably contain at least 15 nucleotides to 50 nucleotides in length. More preferably, the primers may contain 20 nucleotides to 30 nucleotides in length. One skilled in the art recognizes the optimization of the temperatures of the reaction mixture, number of cycles and number of extensions in the reaction. The amplified product (i.e., amplicons) can be identified by gel electrophoresis.

Aided with the help of DNA probe, the real-time PCR provides a quantum leap as a result of real-time detection. In real-time PCR assay, a fluorometer and a thermal cycler for the detection of fluorescence during the cycling process is used. A computer that communicates with the real-time machine collects fluorescence data. This data is displayed in a graphical format through software developed for real-time analysis.

In addition to the forward primer and reverse primer (obtained via commercial sources), a single-stranded hybridization probe is also used. The hybridization probe may be a short oligonucleotide, usually 20-35 base pairs in length, and is labeled with a fluorescent reporting dye attached to its 5'-end as well as a quencher molecule attached to its 3'-end. When a first fluorescent moiety is excited with light of a suitable wavelength, the absorbed energy is transferred to a second fluorescent moiety (i.e., quencher molecule) according to the principles of FRET. Because the probe is only 20-35 base pairs long, the reporter dye and quencher are in close proximity to each other and little fluorescence is detected. During the annealing step of the PCR reaction, the labeled hybridization probe binds to the target DNA (i.e., the amplification product). At the same time, Taq DNA polymerase extends from each primer. Because of its 5' to 3' exonuclease activity, the DNA polymerase cleaves the downstream hybridization probe during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, a Rotor-Gene System is used and is suitable for performing the methods described herein. Further information on PCR amplification and detection using a Rotor-Gene can conveniently be found on Corbett's website.

In another embodiment, suitable hybridization probes such as intercalating dye (e.g., Sybr-Green I) or molecular beacon probes can be used. Intercalating dyes can bind to the minor grove of DNA and yield fluorescence upon binding to double-strand DNA. Molecular beacon probes are based on a hairpin structure design with a reporter fluorescent dye on one end and a quencher molecule on the other. The hairpin structure causes the molecular beacon probe to fold when not hybridized. This brings the reporter and quencher molecules in close proximity with no fluorescence emitted. When the molecular beacon probe hybridizes to the template DNA, the hairpin structure is broken and the reporter dye is no long quenched and the real-time instrument detects fluorescence.

The range of the primer concentration can optimally be determined. The optimization involves performing a dilution series of the primer with a fixed amount of DNA template. The primer concentration may be between about 50 nM to 300 nM. An optimal primer concentration for a given reaction with a DNA template should result in a low Ct- (threshold concentration) value with a high increase in fluorescence (5 to 50 times) while the reaction without DNA template should give a high Ct-value.

The probes and primers of the invention can be synthesized and labeled using well-known techniques. Oligonucleotides for use as probes and primers may be chemically synthesized according to the solid phase phosphoramidite triester method first described by Beaucage, S. L. and Caruthers, M. H., 1981, Tetrahedron Letts., 22 (20): 1859-1862 using an automated synthesizer, as described in Needham-VanDevanter, D. R., et al. 1984, Nucleic Acids Res., 12: 6159-6168. Purification of oligonucleotides can be performed, e.g., by either native acrylamide gel electrophoresis or by anion-exchange HPLC as described in Pearson, J. D. and Regnier, F. E., 1983, J. Chrom., 255: 137-149.

Comparison of Expression Levels of PME-1 Endometrial Cancer Biomarker

Expression levels of PME-1 in a biological sample obtained from a patient (suspected with endometrial cancer) may be compared to the expression levels of PME-1 endometrial cancer biomarker obtained from normal endometrial tissues. Normal endometrial tissues include endometrial tissues obtained from healthy individuals or endometrial tissues obtained from an adjacent area to the cancer regions within the endometrium of the endometrial cancer patients under examination. Comparison may be performed by employing protein concentrations of the endometrial cancer biomarkers, or $\Delta\Delta C_t$ values from qRT-PCR of the endometrial cancer biomarker genes.

Specifically, more aggressive endometrial cancer is associated with an increase in PME-1 expression levels, as compared to normal adjacent endometrial tissue (e.g., FIG. 7 where expression of PME-1 is increased by twenty-fold in endometrial cancer tissue). The correlation between PME-1 and endometrial cancer is used to predict or diagnose endometrial cancer in a patient.

In certain embodiments, the step of comparing the expression levels of endometrial cancer biomarkers (e.g., PME-1) present in a patient sample to an expression level of the same biomarker known to be present in a normal healthy body sample is embodied as employing a cut-off value or threshold value for the concentration of that particular biomarker.

Kits

The present invention provides a kit of manufacture, which may be used to perform detecting either a protein or mRNA for a specific endometrial cancer biomarker. In one embodiment, an article of manufacture (i.e., kit) according to the present invention includes a set of antibodies (i.e., a first antibody and a second antibody) specific for a PME-1 protein biomarker. In another embodiment, the present kit contains a set of primers (i.e., a forward primer and a reverse primer) (directed to a region of the gene specific to a PME-1 biomarker and optionally a hybridization probe (directed to the same gene, albeit a different region)).

Kits provided herein may also include instructions, such as a package insert having instructions thereon, for using the reagents (e.g., antibodies or primers) to quantify the protein expression level of mRNA expression level of a particular endometrial cancer biomarker in a biological sample. Such instructions may be for using the primer pairs and/or the hybridization probes to specifically detect mRNA of a specific gene (e.g., PME-1) in a biological sample. In another, the instructions are directed to the use of antibodies (either monoclonal or polyclonal) that recognize and bind to specific endometrial cancer biomarker.

In another embodiment, the kit further comprises reagents used in the preparation of the sample to be tested (e.g., lysis buffer). The kits of the invention also may further comprise one or more antibodies which specifically bind to PME-1 biomarker.

In one embodiment, the present invention provides a method of using the expression levels of protein phosphatase methylesterase I (PPME1) and its gene product, protein methylesterase 1 (PME-1) as a biomarker for an increased risk in endometrial cancer in humans. The present inventors have established that PME-1 can serve as a biomarker for endometrial cancer, a novel finding that has not been previously recognized. The present invention cures the long-felt needs in that it provides a method for determining whether a woman has an increased risk of endometrial cancer. The method involves detection of an increased level of PME-1, as well as providing method of treatment through inhibition of PME-1, and kits containing the reagents and instruction necessary to employ the method.

Epithelial to Mesenchymal Transition (EMT)

The present inventors discovered that over-expression of PME-1 in endometrial cells leads to increased endometrial cell migration and invasive growth. The phenotype change is associated with activation of ERK and Akt cancer signaling pathways and increased Wnt signaling and phosphorylation of β-catenin, via inhibition of PP2A activity by PME-1. Over-expression of PME-1 in endometrial cells decreases epithelial marker, E-cadherin, and increased expression of mesenchymal markers (e.g., vimentin and Noggin).

The present inventors also discovered that depletion of PME-1 (by siRNA or shRNA) leads to a decrease in endometrial cell proliferation and induces cell senescence. The same outcome was observed in TNBC.

Phenotypic change of endometrial cells induced by PME-1 is found to be associated with EMT characteristics. EMT is involved in metastasis of cancer. EMT is classified into three (3) types. Type 1 EMT involves the transition of primordial epithelial cells into motile mesenchymal cells. This type is involved during embryonic development and organogenesis and is associated with the generation of diverse cell types. Type 2 EMT involves transition of secondary epithelial cells to resident tissue fibroblasts and is associated with wound healing, tissue regeneration, and organ fibrosis. Type 3 EMT occurs in carcinoma cells that have formed solid tumors (such as endometrial cancer or TNBC) and is associated with their transition to metastatic tumor cells that have the potential to migrate through the bloodstream to distant sites. These three (3) types of EMT represent distinct biological outcomes; however, the signals that delineate these subtypes are unclear.

EMT has multiple key hallmarks as evidenced by (1) loss of epithelial polarity due to the loss of organized intercellular junctions, (2) cytoskeletal reorganization, and (3) acquisition of mesenchymal features.

One key hallmark for EMT is the decrease in E-cadherin for epithelial cells (Engelsen, 2009). E-cadherin's normal function is to mediate cell-cell adhesion and thus maintain epithelial tissue integrity. A loss in E-cadherin alters the sequestration of associated cytoplasmic proteins, such as β-catenin. These features are thought to contribute to EMT and metastasis of endometrial cancer as the disease advances.

Another key hallmark for EMT is the increase of P-cadherin for epithelial cells. P-cadherin is a member of the classical cadherin family and is a transmembrane glycoprotein, normally found in the adherens junctions near the apical surface of a cell. Cadherins can interact with β-catenin and are important for regulation of the cytoskeleton. An increase in P-cadherin, with concurrent decrease in E-cadherin levels, can suggest cells capable of migration or indicate more aggressive cancers.

Another key hallmark for EMT is cytoskeletal reorganization. Specifically, several cytoplasmic proteins are used as markers for EMT. Vimentin, an intermediate filament protein present in most mesenchymal cells, is responsible for the strength and integrity of cells and its movements. β-catenin is an adhesion plaque protein that plays a dual role during EMT. In epithelium, β-catenin is located in the cytoplasm and may be bound to E-cadherin. During EMT, β-catenin may translocate into the nucleus and functions as a transcriptional activator together with T cell factor (TCF/LEF) complex to regulate the expression of genes associated with EMT. Nuclear accumulation of β-catenin has been detected in cells undergoing EMT in embryonic development, fibrosis, and cancer and has been used as a biomarker for all three types of EMT.

Another key hallmark for EMT is the activation of Wnt signaling, which is mediated by the binding of ligands, such as Wnt3 or Wnt3a to Frizzled receptors. The activation of this pathway leads to increased nuclear β-catenin and increased transcriptional activity of the TCF/LEF transcription factors, promoting EMT onset.

In another aspect, the present invention provides RNAi knock-down of PME-1 decrease epithelial to mesenchymal transition. There is a direct correlation between the levels of PME-1 and the PP2A activity. The present findings indicate that PME-1 is essential in regulation the process of epithelial to mesenchymal transition, as evidenced by siRNA targeted against PME-1 that inhibits the transition process. Thus, the present invention provides a means to attenuate the endometrial cancer development. The present invention also provides a means to attenuate the triple negative breast cancer development.

The present invention therefore provides a therapeutic strategy of using RNAi targeted against PME-1 as a treatment for endometrial cancer in women. For purposes of this application, RNAi is intended to encompass both siRNA and shRNA. siRNA and shRNA targeted against PME-1 mRNA function equivalents to reduce mRNA of PME-1 mRNA. The present inventors provided the first elucidation for the regulation of the epithelial to mesenchymal transition process by PME-1 in female endometrial cancer. The disclosed data find support in human PME-1 gene may affect PP2A and thus regulate the development of endometrial carcinoma cells, probably via the epithelial to mesenchymal transition.

In one aspect, the present invention provides an isolated double stranded short interfering ribonucleic acid (siRNA) molecule that silences expression of PME-1 mRNA. In another aspect, the present invention provides an isolated single stranded short-hairpin RNAs (shRNA) molecule that is complementary to the initial target sequence which silences expression of PME-1 mRNA.

The mechanism of action of siRNA is understood by one skilled in the art. Interfering RNA (RNAi) generally refers to a single-stranded RNA or double-stranded RNA (dsRNA). The dsRNA is capable of targeting specific messenger RNA (mRNA) and silencing (inhibiting) the expression of a target gene. During the process, dsRNA is enzymatically processed into short-interfering RNA (siRNA) duplexes of 21 nucleotides in length. The anti-sense strand of the siRNA duplex is then incorporated into a cytoplasmic complex of proteins (RNA-induced silencing complex or RISC). The RISC complex containing the anti-sense siRNA strand also binds mRNA which has a sequence complementary to the anti-sense strand—allowing complementary base-pairing between the anti-sense siRNA strand and the sense mRNA molecule. The mRNA molecule is then specifically cleaved by an enzyme (RNase) associated with RISC resulting in specific gene silencing. For gene silencing or knock down (i.e., mRNA cleavage) to occur, anti-sense RNA (i.e., siRNA) has to become incorporated into the RISC. This represents an efficient process that occurs in nucleated cells during regulation of gene expression. When an anti-sense DNA molecule is introduced into a cell, it targets specific mRNA through base-pairing of the anti-sense DNA molecule to its RNA target.

For purposes of this application, the anti-sense strand of the siRNA may comprise a contiguous nucleotide sequence, where the base sequence of the anti-sense strand has sequence complementarity to the base sequence of contiguous nucleotide sequence of corresponding length contained in the mRNA sequence of the targeted mRNA (PME-1 mRNA). Complementary includes complete base-pairing match or a few base-pairing mismatches.

In one embodiment, the anti-sense strand of the siRNA molecule comprises or consists of a sequence that is 100% complementary to the target sequence or a portion thereof. In another embodiment, the anti-sense strand of the siRNA molecule comprises or consists of a sequence that is at least about 90%, 95%, or 99% complementary to the target sequence or a portion thereof. For purposes of this application, the anti-sense strand of the siRNA molecule comprises a sequence that specifically hybridizes to the target sequence or a portion thereof so as to inhibit the target mRNA expression. The present invention also encompasses anti-sense strand siRNAs that target the 3'UTR of the PME-1 RNA insofar as they possess similar activities to inhibit PME-1 mRNA expression.

Without wishing to be bound by a theory, siRNA-mediated RNA interference may involve two-steps: (i) an initiation step, and (ii) an effector step. In the first step, input siRNA is processed into small fragments, such as 21-23-nucleotide 'guide sequences'. The guide RNAs can be incorporated into a protein-RNA complex which is capable of degrading mRNA, the nuclease complex, which has been called the RNA-induced silencing complex (RISC). The RISC complex acts in the second effector step to destroy mRNAs that are recognized by the guide RNAs through base-pairing interactions. siRNA involves the introduction by any means of double stranded RNA into the cell which triggers events that cause the degradation of a target RNA. siRNA is a form of post-transcriptional gene silencing. One of skilled in the art would understand the preparation and utilization of siRNA molecules. (See, e.g., Hammond et al., Nature Rev Gen 2: 110-119 (2001); Sharp, Genes Dev 15: 485-490 (2001), the disclosure of which are incorporated herein by reference in their entireties).

Methods for preparing and isolating siRNA are known in the art (See, e.g., Smabrook et al., Molecular Cloning, A Laboratory Manual ($2^{nd}$ Ed., 1989)), the disclosure of this is herein incorporated by reference in its entirety). In one embodiment, siRNA are chemically synthesized, using any of a variety of techniques known in the art, such as those described in Wincott et al., Nucl. Acids Res., 23:2677-2684 (1995); and Wincott et al., Methods Mol. Bio., 74:59 (1997). The synthesis of the siRNA makes use of common nucleic acid protecting and coupling groups, such as dimethoxytrityl at the 5'-end and phosphoramidites at the 3'-end. Suitable reagents for siRNA synthesis, methods for RNA deprotection, and methods for RNA purification are known to those of skill in the art. Small scale syntheses or large scale syntheses can be conducted using suitable synthesizer and protocols that are recognized in the industry. Preferably, siRNA molecules are chemically synthesized.

siRNA molecules can also be synthesized via a tandem synthesis technique, wherein both strands are synthesized as a single continuous strand separated by a cleavable linker that is subsequently cleaved to provide separate strands that hybridize to form the siRNA duplex. The tandem synthesis of siRNA can be readily adapted to both multi-well or multi-plate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the anti-sense strand of the siRNA. For example, each strand can be synthesized separately and joined together by hybridization or ligation following synthesis and/or de-protection. In certain other instances, siRNA molecules can be synthesized as a single continuous oligonucleotide fragment, where the self-complementary sense and anti-sense regions hybridize to form a siRNA duplex having hairpin secondary structure.

In one embodiment, siRNA comprises a double stranded region of about 15 to about 30 nucleotides in length. Preferably, siRNA has about 20 to about 25 nucleotides in length. More preferably, siRNA has 19 nucleotides. The siRNA molecules of the present invention are capable of silencing the expression of a target sequence in vitro and in vivo.

In another embodiment, the siRNA has an overhang on its 3' or 5' ends relative to the target RNA that is to be cleaved. The overhang may be 2-10 nucleotides long. In one embodiment, the siRNA does not have an overhang (i.e., blunted).

In another embodiment, the siRNA molecule may contain one modified nucleotide. In yet another embodiment, the siRNA may comprise one, two, three four or more modified nucleotides in the double-stranded region. Exemplary modified siRNA molecule includes, but not limited to, modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and the like. The preparation of modified siRNA is known by one skilled in the art.

Short-hairpin RNAs (shRNAs) are still another way of silencing PME-1. shRNAs consist of: i) a short nucleotide sequence, typically ranging from 19 to 29 nucleotides, derived from the target gene; ii) a hairpin loop, typically ranging between 4 to 23 nucleotides; and iii) a short nucleotide sequence reversely complementary to the initial target sequence, typically ranging from 19 to 29 nucleotides. Preferably, the targeting sequence for PME-1 contains 21 nucleotides. Preferably, the hairpin loop sequence contains 6 nucleotides. PME-1 silencing shRNAs may be designed and synthesized by means and methods known a person skilled in the art. Non-limiting examples of PME-1 specific shRNAs include those listed in Table 2. These shRNA are shown effective in reducing PME-1 mRNA in cells.

In general, shRNAs may be transcribed in cells from a plasmid construct. Expression of shRNA from a plasmid is known to be relatively stable, thereby providing strong advantages over other RNAi forms. shRNA expression units may be incorporated into a variety of plasmids, liposomes, viral vectors, and other vehicles for delivery and integration into a target cell. shRNAs are synthesized in the nucleus of cells, further processed and transported to the cytoplasm, and then incorporated into the RNA-induced silencing complex (RISC) where the shRNAs are converted into active molecules, which are capable of binding to, sequestering, and/or preventing the translation of mRNA transcripts encoded by target genes.

Particularly, adenovirus is used. Adenoviruses are linear, double stranded DNA viruses capable of infecting a majority of human and many nonhuman cell types including mouse, rat, dog, chicken, rabbit, sheep, pig, and nonhuman primates, and infection is not dependent on active host cell division. Adenoviral vectors have high efficiency gene delivery and high-level gene expression. These attributes allow adenoviral vectors to be used for the over expression of shRNAs in a broad range of mammalian cells.

In one embodiment shRNA may be transcribed inside the cell nucleus from a vector containing a promoter. The shRNA containing the sense and antisense sequences from a target gene connected by a loop is transported from the nucleus into the cytoplasm where Dicer processes it into siRNAs to knock-down protein expression.

In another embodiment, shRNA maybe transcribed into an adenovirus. Preferably, the adenovirus is adenoviral-Type 5 (dE1/E3).

The present inventors discovered PME-1 over-expression is correlated with the endometrial cancer development. An elevated PME-1 expression (both in protein and mRNA levels) is seen in tissues from endometrial cancer patients. Specifically, PME-1 is over-expressed in high stages and grades in endometrial cancer.

The present observation that there is a correlation in the PME-1 protein expression in matched pair of human endometrial tumor samples further substantiates the important role of PME-1. The present invention provides a therapeutic approach of employing siRNAs to block the PME-1 expressions and thus attenuate the endometrial tumor development. In another aspect, the present invention also provides a therapeutic approach of employing siRNAs to block the PME-1 expressions and thus attenuate the breast cancer tumor development. Preferably, the breast cancer is triple negative breast cancer.

In one aspect, the present invention provides exemplary anti-sense strand siRNAs that hybridize to the PME-1 mRNA so as to increase degradation of PME-1 mRNA (and consequently PME-1 protein expression). In one embodiment, the present invention provides non-limiting exemplary anti-sense strand siRNA targeted against PME-1 (e.g., SEQ ID NOs: 5 and 6) that hybridizes to PME-1 mRNA. In another embodiment, the present invention provides non-limiting exemplary anti-sense strand shRNA targeted against PME-1 (e.g., SEQ ID NOs: 2 and 3).

The present RNAi molecule targeting PME-1 can be used to down-regulate or inhibit the expression of PME-1. The PME-1 expression is inhibited at least about 40%-100%.

RNAi may conveniently be delivered to a target cell through a number of direct delivery systems. For example, RNAi may be delivered via electroporation, lipofection, calcium phosphate precipitation, plasmids, viral vectors, viral nucleic acids, phage nucleic acids, phages, cosmids, or via transfer of genetic material in cells or carriers such as cationic liposomes. In one embodiment, transfection of RNAi may employ viral vectors, chemical transfectants, or physico-mechanical methods such as electroporation and direct diffusion of DNA. The RNAi delivery methods are known in the art and readily adaptable for use. (See, e.g., Wolff, J. A., et al., Science, 247, 1465-1468, (1990); and Wolff, J. A. Nature, 352, 815-818, (1991)).

In one aspect, the present invention provides a pharmaceutical composition containing RNAi targeted against PME-1 for the treatment of endometrial cancer. The pharmaceutical composition comprises the RNAi as therapeutic agents for inhibiting PME-1 gene activity and a pharmaceutical acceptable carrier. Pharmaceutically acceptable carriers include, but are not limited to, excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to aid absorption in the gastrointestinal tract.

Pharmaceutical compositions containing RNAi may be administered to a mammal in vivo to treat cancer. In one embodiment, the pharmaceutical formulation includes a dosage suitable for oral administration. In another embodiment, the pharmaceutical formulation is designed to suit various means for RNAi administration. Exemplary means include uptake of naked RNAi, liposome fusion, intramuscular injection via a gene gun, endocytosis and the like. These administration means are well known in the art.

The present invention provides a means for attenuating (i.e., inhibiting) the PME-1 gene using RNAi targeting against PME-1. The present invention provides a method of reducing epithelial to mesenchymal transition in endometrial cancer cells by reducing PME-1 expression levels. Specifically, the present invention provides a method of using RNAi targeted against PME-1 in attenuating the PME-1 expression in endometrial cancer. The use of RNAi to attenuate PME-1 represents a prognostic tool in treating human endometrial carcinoma.

In one embodiment, the RNAi is administered to a human with a therapeutic effective amount of RNAi targeting PME-1. The specific amount that is therapeutically effective can be readily determined by monitoring the PME-1 mRNA levels. Inhibition of PME-1 mRNAs is conveniently achieved by using qRT-PCR, Northern blot analysis and other techniques known to those of skill in the art such as dot blots, in situ hybridization, and the like. The inhibition level is comparing the target gene expression to the control. A detectable inhibition can be about 40%-100%. Preferably, the % inhibition may be 80%, 90% or 100%. The therapeutic effective amount may be determined by ordinary medical practitioner, and may vary depending on factors known in the art, such as the patient's history and age, the stage of pathological processes mediated by PME-1 expression.

The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXPERIMENTAL STUDIES

Example 1

PME-1 Expression in Endometrial Cell Lines

In these initial studies, we sought to determine the expression levels of PME-1 in various human endometrial cell lines (EC). We examined the expression level of PME-1 protein using Western Blot analysis (See, Materials and Methods).

Figure 1:
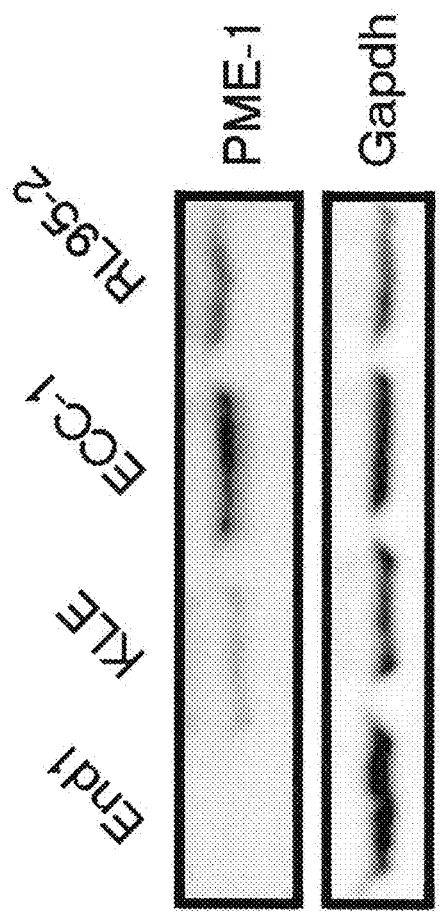
FIG. 1 shows a Western blot depicting the basal expression of PME-1 protein compared to GAPDH (loading control) for (i) the immortalized endocervical cell line (End1), (ii) the non-aggressive endometrial cancer cell line (KLE), and (iii) the highly aggressive endometrial cancer cell lines, (ECC-1 and RL95-2).
Figure 2:
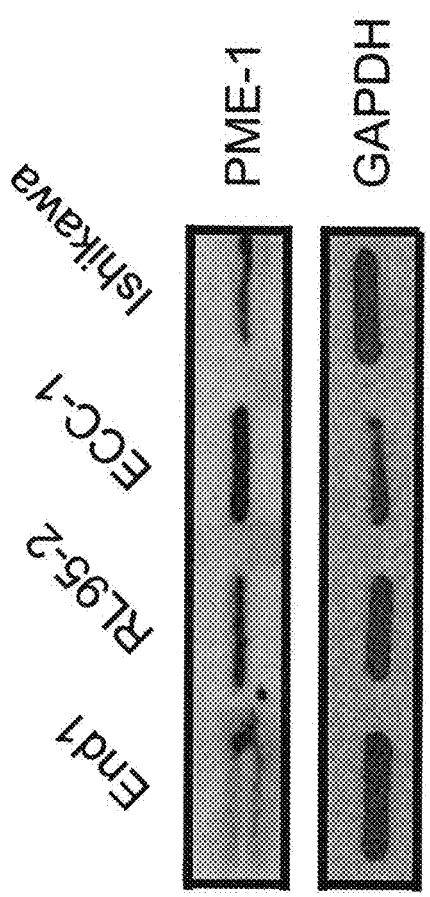
FIG. 2 shows another Western blot depicting the basal expression of PME-1 protein compared to GAPDH (loading control) for (i) the immortalized endocervical cell line (End1) and (ii) the endometrial cancer cell lines (RL95-2, ECC-1, Ishikawa). ECC-1 and Ishikawa cell lines are closely related but ECC-1 is more aggressive than Ishikawa.

As shown in FIGS. 1 and 2, the more aggressive/metastatic EC cell lines (RL95-2, Ishikawa, and ECC-1) were found to express more abundant PME-1 protein as compared to the less aggressive/metastatic EC line (KLE) and the immortalized endocervical cell line, End1. GAPDH was used as a loading control in these studies. These data suggest that PME-1 is expressed in endometrial cancer cells. The expression of PME-1 protein levels correlates with the degree of aggressiveness of EC; namely, the more aggressive/metastatic activity of EC, the higher the expression of PME-1 protein levels.

Example 2

Western Blot Analysis of PME-1 Protein Expression in Tissue Samples from Patients with Endometrial Adenocarcinoma After establishing that the degree of aggressiveness/metastasis in EC cell lines indeed correlates with an increased level of PME-1 protein, we next determined whether the same trend might occur in endometrial tissue samples obtained from patients.

Figure 3:
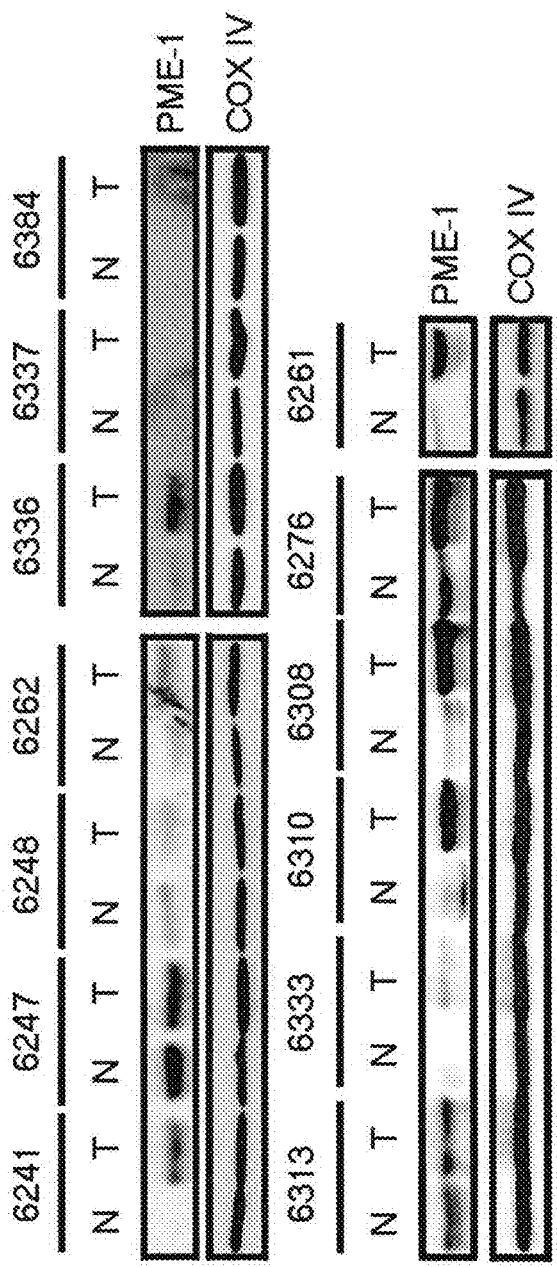
FIG. 3 shows a Western blot depicting a representative panel of endometrial cancer patient samples examining the levels of PME-1 protein in tumor (T) and normal adjacent tissue (NAT, N) by Stage. The tumor and normal adjacent tissue samples were harvested from the same patient. Patient information is available in Table 1.

We obtained 30 matched pairs of tissue samples harvested from patients with endometrial adenocarcinoma. The details of the relevant patient data are provided in Table 1. We used Western Blot analysis to monitor the expression of PME-1 protein levels in these tissue samples from patients (FIG. 3).

Representative Western blots are displayed for several stage I EC patient samples. All stage II and stage III tissue samples purchased are also shown in FIG. 3. The top left panel shows stage IB patient samples (patient #6241, 6247, 6248, 6262) except for #6262, which is a grade 1 tumor. The top right panel shows three (3) stage IC in which only one sample (patient #6336) displays an increase in expression of PME-1 protein in the tumor sample (T) versus the NAT sample (N). Three (3) out of seven (7) stage I patient EC samples show only a detectible PME-1 protein level in the tumor sample (patient #6241, 6247, 6336); however, one patient sample (#6247) expressed PME-1 protein in the NAT sample. The bottom left panel displays both Stage II samples (patient #6313, 6333) and there is a slight increase in PME-1 protein for both patients.

Importantly, PME-1 protein was found to increase in all stage III patient tumor samples as compared to their corresponding NAT samples (patient #6310, 6308, 6276, 6261).

Figure 4:
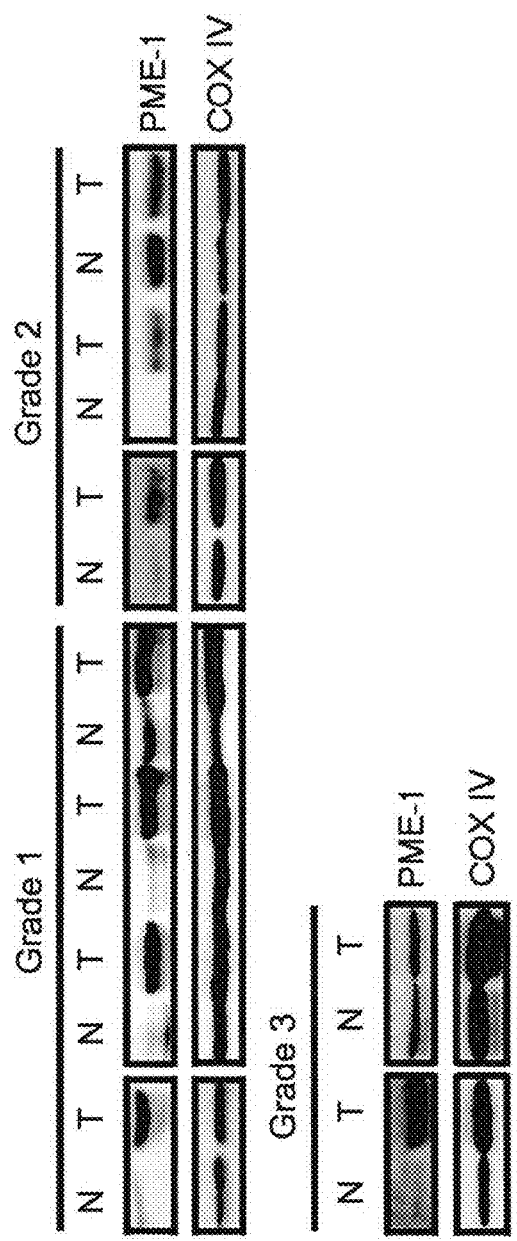
FIG. 4 shows a Western blot depicting a representative panel of endometrial cancer patient samples examining the levels of PME-1 protein in tumor (T) and normal adjacent tissue (NAT, N) by grade. The tumor and normal adjacent tissue samples were harvested from the same patient.

As shown in FIG. 4, PME-1 levels were assessed in patient samples according to FIGO grade. In general, PME-1 expression increased in tumor tissue (T) as compared to NAT samples. For purposes of this application, the comparison in our clinical study involves comparing tumor tissue samples in patients suffering from endometrial cancer relative to the normal adjacent tissue samples from the same individual. For practical purposes, our clinical assay can be performed using normal tissues obtained from normal women (free of endometrial cancer) instead of the normal adjacent tissues.

Altogether, the present data demonstrate that PME-1 protein levels increase as grade and/or stage increases, suggesting that PME-1 levels correlate with the aggressiveness of the endometrial cancer. Because PME-1 protein levels were found to increase in all four (4) stage III EC patients and the increase was dramatic as compared to the NAT samples, we conclude that there is a correlation in PME-1 levels and high grade/stage of EC tumors.

Example 3

Immunohistochemistry Analysis

We confirmed the PME-1 protein expression data by evaluating the immunohistochemistry of the tissue samples from EC patients. This immunohistochemistry study provides the basis for our observation of an increased PME-1 expression level in the context of tissue morphology.

Figure 5:
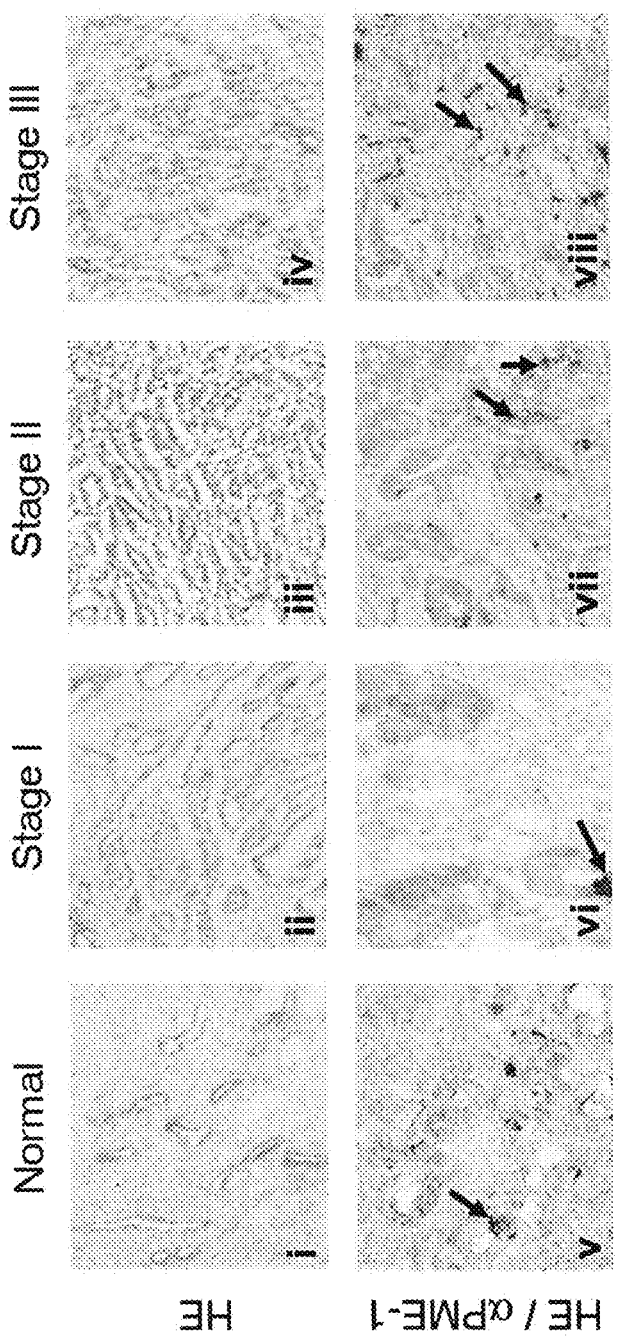
FIG. 5 depicts immune-histochemistry of patient tissue samples representing the morphology of normal endometrial tissues (i, v) and endometrial cancers at different stages (i.e., Stages I-III, (ii-iv)) and the different expression patterns of PME-1 as the endometrial cancer's stage progresses (i.e., vi-viii).

We performed H&E staining on the tissue samples (FIG. 5*i-iv*) and co-stained tissue samples with anti-PME-1 antibodies (FIG. 5*v-viii*). Normal tissue showed regular gland formation in the endometrium with light PME-1 expression around glands within epithelial cells, as illustrated by the black arrows (FIG. 5*i, v*). In stage I EC, glands became irregular and PME-1 localization becomes more punctated and localized, as illustrated by the black arrows (FIG. 5*ii, vi*). Stage II EC was even less organized with increased PME-1 staining and more foci, as illustrated by the black arrows (FIG. 5*iii, vii*).

In stage III EC, PME-1 staining was darker and appeared to be limited to individual cells, marked by black arrows (FIG. 5*iv, viii*), which was consistent with the hypothesis that the cells were migrating through the tumor stroma due to their elongated morphology. The data support our Western blot analysis that PME-1 expression levels increased with increased stages. The visualization of migrating cells darkly stained for PME-1 in Stage III tumors suggest that PME-1 expression is increased in cells that have undergone epithelial-to-mesenchymal transition (EMT).

Figure 6:
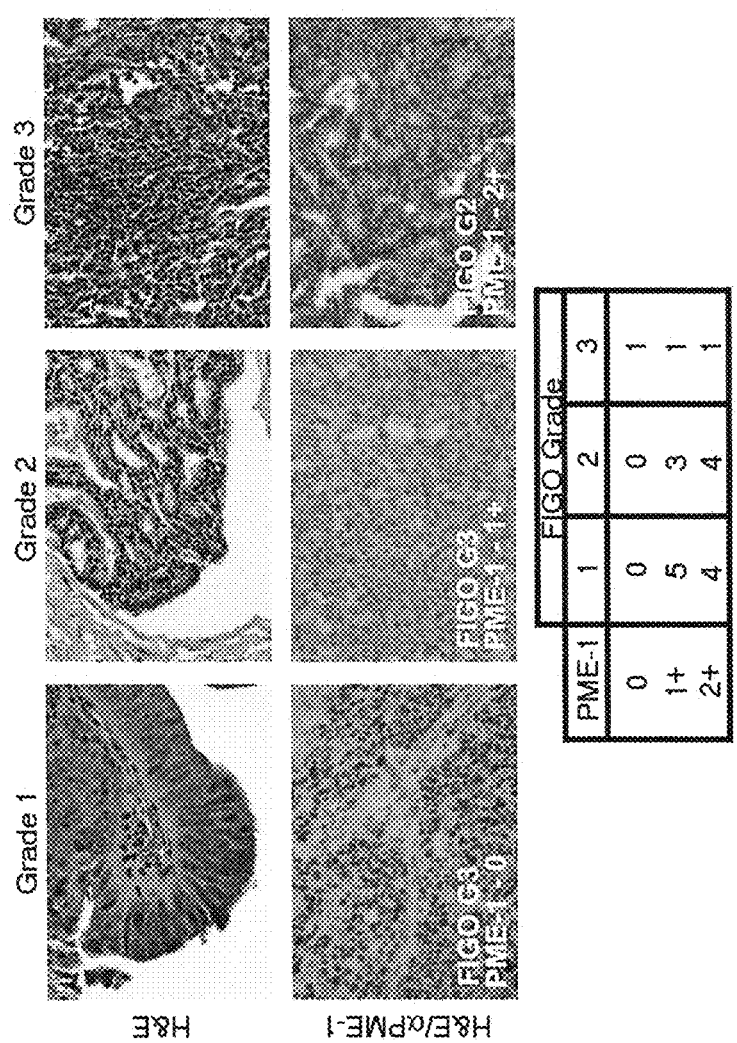
FIG. 6 depicts immune-histochemistry of patient tissue samples representing the morphological changes in endometrial tissues as endometrial cancer grade increases (top panels). The hematoxylin and eosin staining (H&E staining) in combination with anti-PME-1 immunohistochemistry (IHC, bottom panels) depict the grading of samples based on PME-1 levels. The PME-1 grading system is as follows: 0 indicates negative cytoplasmic PME-1 staining or faint staining observed in <50% of the cells; 1+ indicates weakly positive cytoplasmic PME-1 staining in >50% of tumor cells or moderate/strong staining in <50% of tumor cells; 2+ indicates strongly positive staining with moderate/strong cytoplasmic staining observed in >50% of the tumor cells. Representative images for PME-1 grading are shown. The table summarizes the data obtained from the tissue samples examined by IHC.

Samples were analyzed by grade as well (FIG. 6). Patient samples were sectioned, H&E stained, and graded according to the International Federation of Gynecology and Obstetrics (FIGO) grading system for endometrial cancer. In the top panels, H&E staining was conducted to exemplify the differences in endometrial cancer grade. Grade 1 tumors are well-differentiated cancers with clear cellular boundaries and normal cell morphology. Grade 2 tumors are moderately differentiated with abnormal cell morphology. Grade 3 tumors are poorly differentiated exhibiting loss of clearly defined boundaries and highly abnormal cell morphology.

The bottom panels (FIG. 6) depict representative immunohistochemistry slides in which sections were H&E stained and were immunostained with antibodies specific for PME-1. PME-1 staining intensity was then graded according to the following scale: 0 indicates negative cytoplasmic PME-1 staining or faint staining observed in <50% of the cells; 1+ indicates weakly positive cytoplasmic PME-1 staining in >50% of tumor cells or moderate/strong staining in <50% of tumor cells; 2+ indicates strongly positive staining with moderate/strong cytoplasmic staining observed in >50% of the tumor cells.

The table in FIG. 6 summarizes the results for PME-1 staining intensity. Of the 9 FIGO grade 1 samples examined, 55% were 1+ and 45% were 2+, whereas of the 7 FIGO grade 2 samples examined, 43% were 1+ and 57% were 2+. All FIGO grade 1 and grade 2 samples exhibited weak to strong staining for PME-1. Only three FIGO grade 3 samples were examined by IHC for PME-1 and no trend was determined. PME-1 immunopositivity was detected in 18 of 19 samples (~95%) tested by IHC (as shown in FIG. 6 in the table), suggesting that PME-1 strongly correlates with disease. An increase level in PME-1 2+ staining was observed in grade 2 compared to grade 1 patient samples (57% versus 44%), suggesting that PME-1 levels increased as the tumor grade increases from 1 to 2.

Example 4

PME-1 mRNA Expression

So far, our data indicate a correlation between increased stages of EC patient samples with increased expression level of PME-1 protein. In this series of studies, we examined if PPME1 mRNA expression levels were increased in patient samples.

We used quantitative real-time PCR to determine the mRNA levels of PPME-1 in the EC patient tissue samples. Total RNA was extracted from tissue samples of matched pair, tumor (T) and normal adjacent tissue (NAT, N). Patient data is presented in Table 1. The level of PPME1, the gene that codes for PME-1, was determined by qPCR using 18S to normalize PME-1 expression. All samples were then normalized to PME-1 expression in RL95-2 cells, which was set to a value of 1.

Figure 7A:
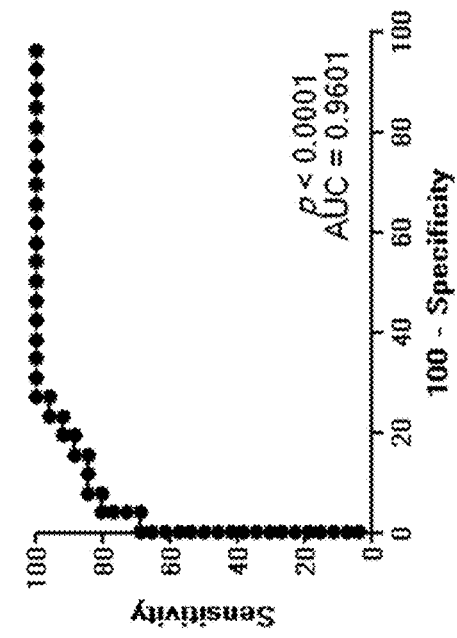
FIG. 7A depicts a quantitative PCR of the levels of PPME1 expression in tissue samples. PME-1 gene (i.e., PPME1) is the gene that codes for PME-1 protein. Each sample was normalized to the expression of 18S. All samples were then normalized to RL95-2 for comparison.
Figure 7B:
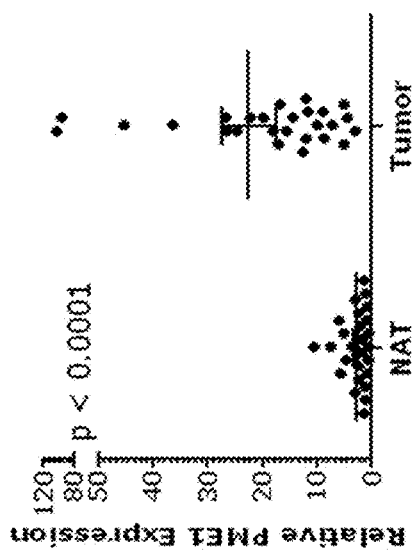
FIG. 7B depicts a ROC analysis of the data set in FIG. 4A, demonstrating PPME1 levels may be predictive of endometrial cancer. Note that the area under the curve is >0.9, with a likelihood ratio of 21. The sensitivity was calculated to be 80.77% and the specificity 96.15%.

The mean expression of PPME1 was >20-fold higher in tumor samples as compared to that of normal samples (FIG. 7A). Statistical significance was determined via the Mann-Whitney non-parametric statistics test. Importantly, ROC analysis (FIG. 7B) demonstrates that detection of PPME1 levels may be a beneficial diagnostic marker, as the area under the curve (AUC) score is >0.9, the sensitivity of the assay is 80.77% and the specificity is 96.15%, when the likelihood ratio is 21, suggesting that PME-1 levels may be predictive of EC. When we compared the ratio of PPME1 expression within matched pairs of the patient samples (i.e. the level of PPME1 in tumor versus the level of PPME1 in the normal adjacent tissue from the same patient), we found that eleven (11) out of thirteen (13) FIGO grade 1, ten (10) out of twelve (12) FIGO grade 2, and three (3) out of five (5) FIGO grade 3 tumors had very high levels of PPME1 in the tumor samples (Table 1). In sum, these data suggest that PME-1 may serve as a useful biomarker for determining more aggressive EC risk for metastasis as higher levels correlate with more aggressive cancers.

Example 5

Effects of siRNA/shRNA Targeted Against PME-1

To confirm our findings that PME-1 levels may be predictive of aggressiveness and metastasis ability in EC, we used the RL95-2 EC cell line, which we transfected with siRNA or shRNA against PME-1. The RL95-2 EC cells were chosen because they represent a highly metastatic endometrial adenocarcinoma cell line.

Figure 8:
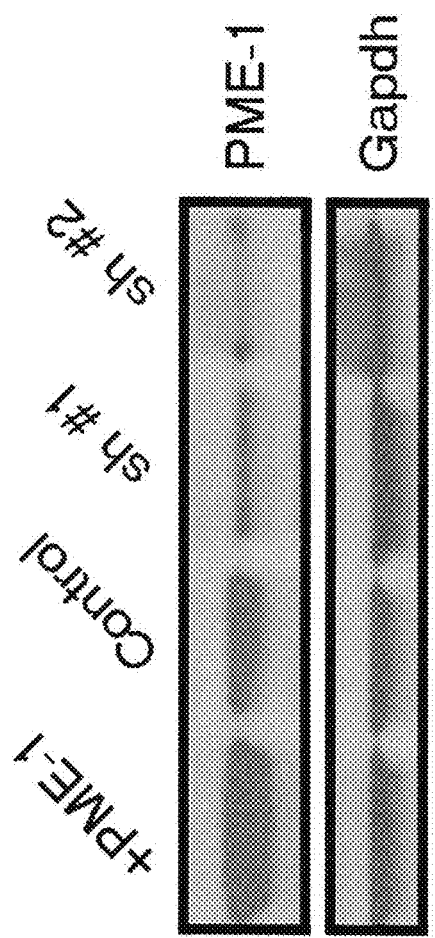
FIG. 8 shows a Western blot of RL95-2 cells depicting the expressing empty vector (Empty), the over-expressing PME-1 (+PME-1) and the expressing shRNA against PME-1 (shRNA #1, #2 SEQ ID NO: 1 and 2, respectively) demonstrating the proper levels of PME-1 protein. Note that shRNA #2 (SEQ ID NO: 2) was used for all subsequent experiments. shRNA sequences are presented in Table 2.

We prepared RL95-2 cell lines expressing empty vector (control), over-expressing PME-1 (+PME-1), or expressing shRNA against PPME1, the gene that codes for PME-1 protein (-PME-1). Using these cells, we confirmed the appropriate level of PME-1 via real-time RT-PCR (data not shown) and Western blot analysis (FIG. 8). GAPDH was used as a loading control.

We also prepared two different shRNAs targeted against PME-1. Both shRNA#1 (SEQ ID NO: 2) and shRNA#2 (SEQ ID NO: 3) significantly decreased PME-1 levels as determined by Western blot analysis. For all subsequent in vitro studies, we used shRNA #2 (SEQ ID NO: 2) because it significantly depleted the PME-1 protein in RL95-2 cells.

Example 6 siRNA Targeted Against PME-1 Increases PP2A Activity

Because PME-1 is a known inhibitor of PP2A, we confirmed in this study that depletion of PME-1 by siRNA led to an increase in PP2A activity in cells. To do so, we treated RL95-2 cells with either non-targeting siRNA (Control) or siRNA targeted against PPME1 (e.g., SEQ ID NO: 5 and SEQ ID NO: 6). PP2A activity was monitored using a phosphatase assay (R&D Systems Duo IC Set phosphatase assay kit). In the phosphatase assay, we used 500 gig of whole cell extract and followed the manufacturer's recommendations.

Figure 9B:
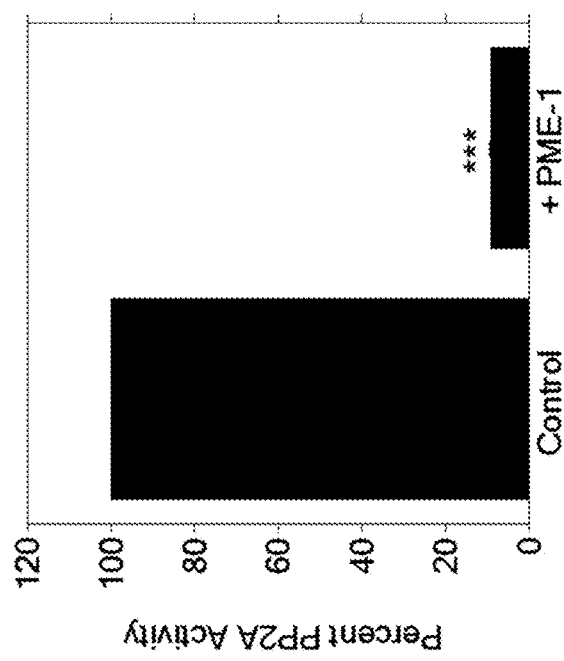
FIG. 9B depicts RL95-2 cells that were treated with empty vector (control) or over-expressed with PME-1 protein (+PME-1). The RL95-2 cells were collected to analyze changes of PP2A phosphatase activity. Increased PPME1 leads to a 90% decrease in PP2A activity, demonstrating that PME-1 is an inhibitor of PP2A activity.
Figure 9A:
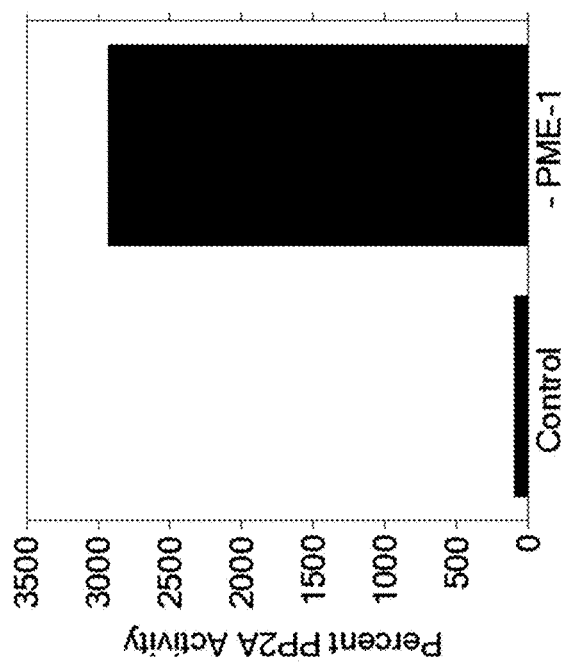
FIG. 9A depicts RL95-2 cells (a human endometrial cell line) stably transfected with a control shRNA (non-targeting) and a shRNA targeted against PPME1 (the gene that codes for PME-1) (SEQ ID NO: 2). The RL95-2 cells (post-transfection) were collected to analyze changes of PP2A phosphatase activity. Depletion of PPME1 induced by shRNA targeted against PPME1 leads to a ~30-fold increase in PP2A phosphatase activity, demonstrating that PME-1 protein is an inhibitor of PP2A activity.

We found that shRNA targeted against the PPME1 gene led to a 30-fold increase in PP2A activity, confirming that siRNA against PPME1 regulates PP2A activity (FIG. 9A). These data indicate that inhibition of PME-1 significantly increases PP2A activity. Conversely, we found that over-expression of PPME1 led to a significant 90% decrease in PP2A activity (FIG. 9B). These data indicate that increased PME-1 activity decreases PP2A activity. We speculate that increase (reactivation) of PP2A activity in cancer may serve as a beneficial therapeutic means to slow tumor growth and metastasis.

Example 7

Foci Forming Assay

In these series of study, we examined if PME-1 might affect tumor cell growth. Specifically, we tested that inhibition of PME-1 would lead to a decrease in tumor cell growth or proliferation.

A foci forming assay was used to monitor cell growth. Equal amounts of tumor cells were plated and they were allowed to grow for a determined period of time (see Materials and Methods section for details). The foci that were formed were then stained with the crystal violet dye. Cells were washed 3 times with PBS prior to visualization. Numbers of foci were counted and results were averaged among different experiments.

Figure 10B:
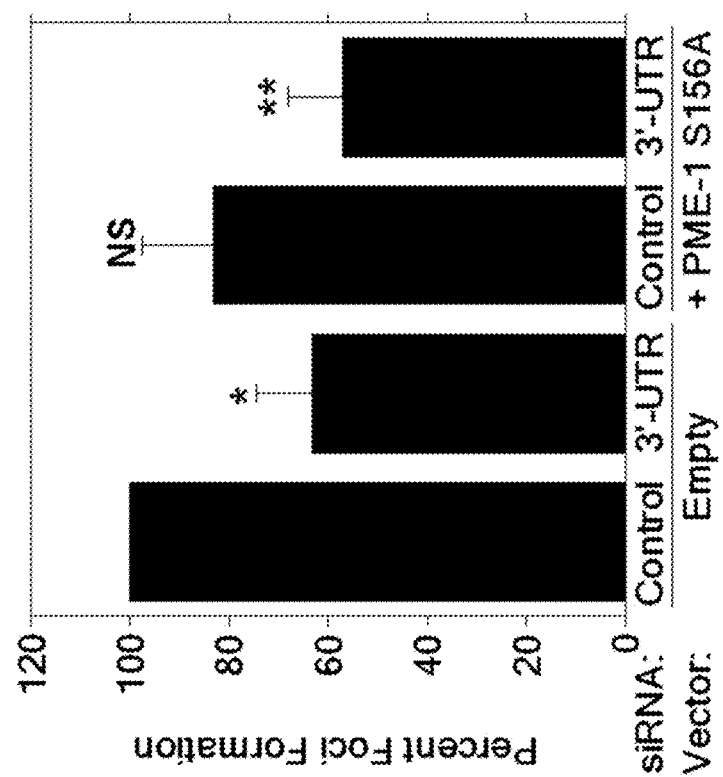
FIG. 10B depicts RL95-2 cells treated with control siRNA (non-targeting) or siRNA against the 3'-UTR of the PME-1 gene (3'-UTR) (SEQ ID NO: 5) to deplete cells of endogenous PME-1 levels. The cells were transfected with empty vector (Empty) or a vector over-expressing the inactive form of PME-1 (PME-1 S156A). Cell proliferation of RL95-2 was then assayed via foci growth. siRNA-targeted DNA sequences are presented in Table 2. *p<0.05, **p<0.01
Figure 10A:
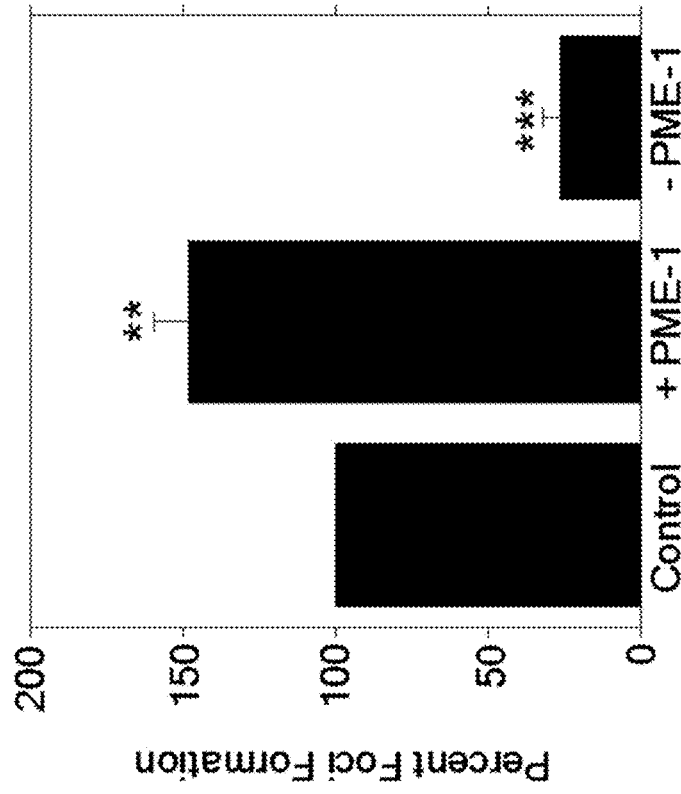
FIG. 10A depicts the foci growth of RL95-2 cells expressing empty vector (Empty), over-expressing PME-1 (+PME-1) and expressing shRNA against PME-1 (−PME-1) (SEQ ID NO: 2) p<0.01, *p<0.001.

As shown in FIG. 10, there was a 50% increase in foci when PME-1 was over-expressed. In contrast, a 75% decrease in foci was observed when PME-1 was depleted as compared to control cells (FIG. 10A).

Example 8

Foci Forming Assay—Confirmation

To determine if the loss of active PME-1 accounted for the observed decrease in foci formation, we first treated RL95-2 cells with siRNA against the 3'-UTR of PPME1 (SEQ ID NO: 5 and SEQ ID NO: 6) to decrease endogenous levels of PME-1. Then we overexpressed either an empty vector or a catalytically inactive form of PME-1 (S156A—in which the nucleophilic serine residue is mutated to an alanine) in the RL95-2 cells (FIG. 10B). The S156A PME-1 mutant is not capable of de methylaing its target, PP2A.

When PME-1 was depleted from the treatment with siRNA (SEQ ID NO: 5 and SEQ ID NO: 6) against the 3'-UTR of the PPME1 gene followed by expression with an empty vector, there was a significant 40% decrease in foci formed when compared to the control siRNA treatment with empty vector expression. When we depleted the endogenous PME-1 with the 3'-UTR siRNA (SEQ ID NO: 5 and SEQ ID NO: 6) and over-expressed the 5156A mutant form of PME-1, there was still a 40% reduction in foci formation.

When cells were treated with 3'-UTR siRNA (SEQ ID NO: 5 and SEQ ID NO: 6) and wild type PME-1 was added back in a vector, foci formation was rescued and returned to a higher level than in the control siRNA+Empty vector sample (data not shown). These data suggest that active PME-1 is required for the maintenance of foci formation and increased tumor cell proliferation.

Example 9

BrDU Incorporation Assay

To confirm our foci formation data that altering PME-1 levels in endometrial cancer cells affect their rate of cell proliferation, we conducted a BrDU incorporation assay. BrDU is incorporated into newly synthesized DNA and can be detected with antibodies; thus, increased BrDU incorporation correlates with an increased level of proliferation.

Figure 11:
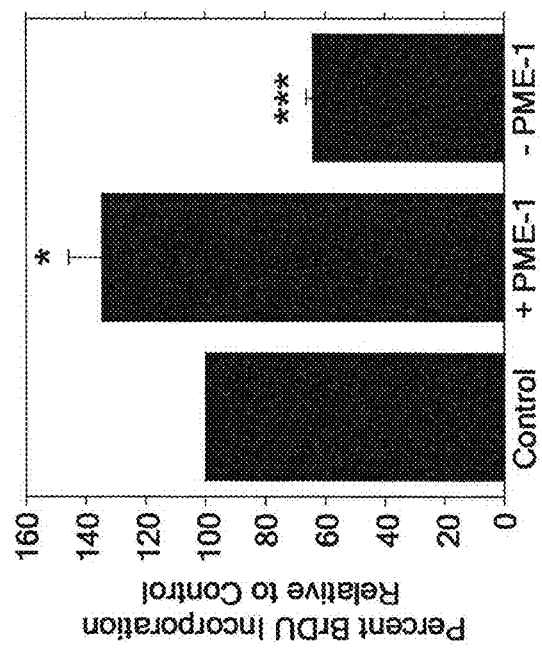
FIG. 11 depicts RL95-2 cells stably expressing control vector (Control), over-expressing PME-1 (+PME-1), or expressing shRNA against PME-1 (−PME-1, SEQ ID NO: 2) that were subjected to a Bromodeoxyuridine (BrdU) incorporation assay, which monitors the rate of cell proliferation. BrdU is incorporated into newly synthesized DNA and can be passed into daughter cells and is a direct measure of cell proliferation. Error bars representing SEM and the significance were calculated by the standard student's t test; where *p<0.05, p<0.01, *p<0.001.

We found that RL95-2 cells over-expressing PME-1 (+PME-1) exhibited a significant 40% increase in BrDU incorporation compared to empty vector control (FIG. 11), whereas depleting cells of PME-1 (−PME-1) with shRNA (SEQ ID NO: 2) led to a significant 40% decrease in BrDU incorporation compared to a scrambled shRNA control (FIG. 11). Each control was set to a value of 100% incorporation. These data further suggest that PME-1 promotes cell proliferation.

Example 10

Immunofluorescence Assay of Mitotic Cells

Figure 12:
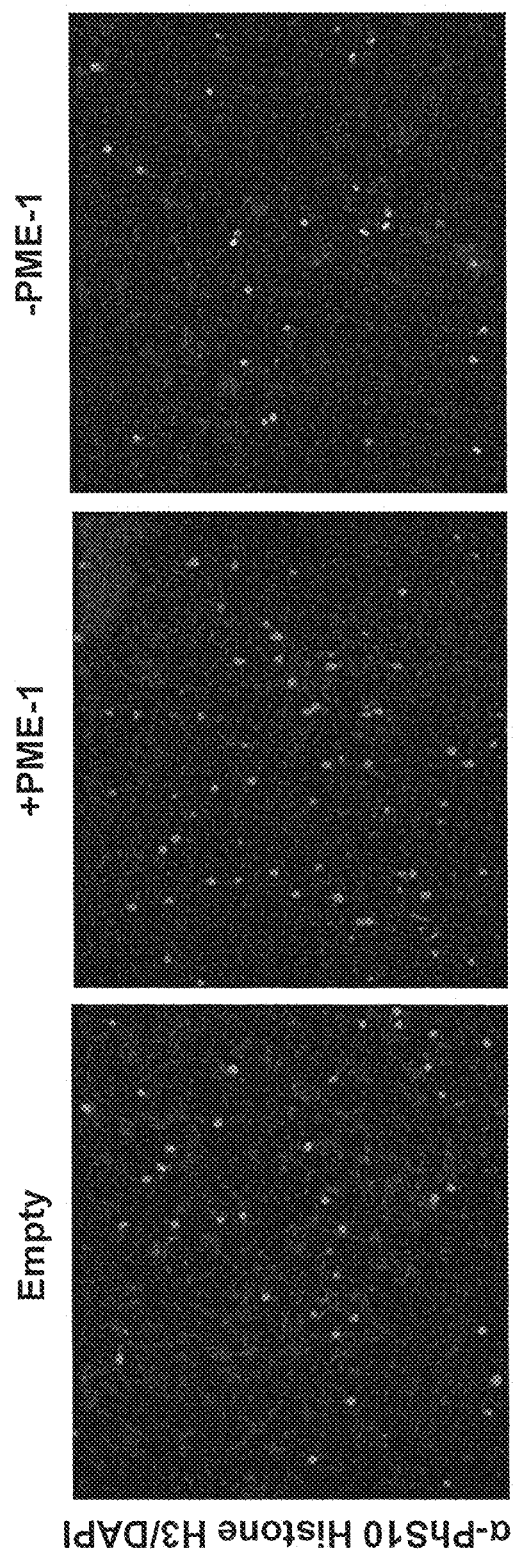
FIG. 12 depicts stained DAPI (blue) RL95-2 cells expressing empty vector (Empty), over-expressing PME-1 (+PME-1) and expressing shRNA against PME-1 (−PME-1, SEQ ID NO: 2). The cells were also analyzed by immunofluorescence, in which an antibody against phosphorylated histone H3 (red) was used to identify mitotic or proliferating cells.

To confirm our foci formation and BrDU incorporation data that suggest that altering PME-1 levels in endometrial cancer cells affect their rate of cell proliferation, we conducted an immunofluorescence assay. Endometrial cancer cells were stained for phosphorylated histone H3 on serine 10, a marker of mitotic cells, followed by counterstaining with DAPI (FIG. 12) to identify all cells.

We found that 2.3-fold more +PME-1 cells were actively proliferating and that there was ~30% decreased proliferation in −PME-1 cells compared to control cells. Taken together, these data suggest that PME-1 promotes endometrial tumor cell proliferation.

Example 11

TUNEL Assay

Our data show that a decrease in levels of PME-1 in RL95-2 cells, whether through siRNA or shRNA targeting of PPME1 message, led to a decrease in cell growth. A decrease in cell growth might be due to cells entering programmed cell death, or apoptosis, or cell senescence, a state in which a cell exits the cell cycle.

To test for the involvement of apoptosis, we used siRNA (SEQ ID NO: 5 and SEQ ID NO: 6) against the PPME1 gene or control siRNA and conducted an immunofluorescence assay called a TUNEL assay. In this assay, all cells were stained blue with the nuclear stain, DAPI, and cells that were undergoing apoptosis would stain green with the addition of fluorescein, which bound to fragmented DNA. Fragmented DNA is a hallmark of apoptotic cells. We found that the decrease in cell proliferation of cells depleted for PME-1 was not due to apoptosis, since PPME1 siRNA treatment did not lead to detection of apoptotic cells (FIG. 13A). A positive control was included in the assay to determine that the assay conditions were optimal. In the positive control, RL95-2 cells were treated with DNase. In sum, the TUNEL assay demonstrated that loss of PME-1 does not cause apoptosis in EC cells.

Example 12

Senescence Assay

We next analyzed cell lysates taken from RL95-2 cells that expressed either empty vector (Control), overexpressed PME-1 (+PME-1) or expressed shRNA against PME-1 (−PME-1) for DcR2 protein. DcR2 protein is a marker of senescent cells and the expression level of DcR2 protein was shown to increase when cells are senescing.

Western analysis demonstrates that loss of PME-1 correlates with an increase in the senescent marker protein, DcR2, suggesting that inhibition of PME-1 activity pushes the cells towards senescence (FIG. 13B). In sum, these data support the hypothesis that inhibition of PME-1 increases PP2A activity and thus decreases cell proliferation in the EC cell line. We also show that loss of PME-1 activity leads to a decrease in cell growth that is not caused by apoptosis, but by cell senescence.

Example 13

PME-1 Expression Correlates with EMT

So far, we showed that PME-1 promotes cell proliferation (FIGS. 10, 11, 12) and that PME-1 expression increases in late stage/high grade EC (FIGS. 3, 4, 5, 6, Table 1). In the immunohistochemistry study, we observed that PME-1 staining in stage III EC occurred in cells that appear to be migrating through the tumor stroma (FIG. 3viii). Based on these results we hypothesized that PME-1 plays a role in epithelial-to-mesenchymal transition (EMT).

In this study, we examined if PME-1 was expressed in cells that also expressed E-cadherin, a marker of epithelial cells, or P-cadherin, a marker of aggressive or mesenchymal endometrial cancer cells. Tissue samples from patients with endometrial adenocarcinoma were purchased from Proteogenex and were analyzed by fluorescent microscopy (FIG. 14). In this Figure, PME-1 was shown in green, and P-cadherin (FIG. 14A) and E-cadherin (FIG. 14B) were displayed in red. Merged figures showed co-expression of the proteins in yellow and are marked with white arrows.

We found that both grade 1 (patient 06313) and grade 3 (patient 06294), PME-1 and P-cadherin expression was increased compared to corresponding NAT samples (FIG. 14A). In grade 1 samples, more cells expressed PME-1 and P-cadherin, but in grade 3 samples, we noted single cells staining brightly for both proteins (arrows in merge). We then examined PME-1 and E-cadherin expression in grade 1 and grade 3 tumors. There is overlap in PME-1 and E-cadherin expression in the grade 1 sample (FIG. 14B, arrows in merge), but in grade 3 EC, PME-1 is not co-expressed with E-cadherin, suggesting that the cells expressing PME-1 in grade 3 tumors are no longer epithelial but mesenchymal in nature.

Example 14

Colony Forming Assay

To determine if PME-1 contributes to the more invasive and metastatic phenotypes, we performed a colony forming assay in matrigel. RL95-2+PME-1 cells formed 50% more colonies than control cells, whereas −PME-1 cells exhibited a 50% decrease in colony formation (FIG. 15).

Importantly, the colonies that were formed by +PME-1 cells were less spherical (FIG. 16, −TGF-β) as compared to the control cells and exhibited rough edges (arrows), suggesting migration of the cells from the cyst. Moreover, −PME-1 cells produced fewer and smaller colonies as compared to the control cells, suggesting that loss of PME-1 decreases invasive growth phenotypes in EC. Upon addition of TGF-β, which induces EMT, we found that there is an overall decrease in colony number; however, cells over-expressing PME-1 (+PME-1) formed large and highly irregular colonies compared to control and −PME-1 cells (FIG. 16, +TGF-β)

Example 15

Raf/MEK/ERK Signaling Pathways

Another signaling event common in many proliferating cells is the activation of the Raf/MEK/ERK and Akt signaling pathways. Continuous activation of these pathways is believed to promote EMT. Activation of the Raf/MEK/ERK pathway can be detected by examining the phosphorylation status of ERK. Furthermore, phosphorylation of Akt on S473 and/or T308 represents activation of the Akt signaling pathway.

In this study, we show via immunofluorescence that we successfully over-expressed PME-1 in RL95-2 cells (compare FIG. 17Aii to FIG. 17Ai). Importantly, we found that the increase in PME-1 levels correlates with an increase in phosphorylated ERK (FIG. 17Bii compared to FIG. 17Bi) while the levels of total ERK remain unchanged (FIG. 13Biii-iv).

Western analysis confirmed these results in RL95-2 cells; when PME-1 was over-expressed, there was a significant increase in phosphorylated ERK, while total ERK levels remain unchanged (FIG. 18A). When PME-1 was depleted with shRNA (SEQ ID NO: 2), there was a decrease in phospho-ERK compared to control cells.

Treatment of cells with UO126 (an upstream inhibitor of ERK phosphorylation) demonstrates the specificity of the phospho-ERK antibody. In sum, the data support our hypothesis that increased levels of PME-1 promote cell proliferation through activation of the Raf/MEK/ERK signaling pathway.

Example 16

Increased Phosphorylation of Akt

We observed a similar trend for the Akt signaling pathway. There was an increase in phosphorylation of Akt on threonine 308 (T308) when PME-1 was over-expressed compared to control. There was a decrease in phosphorylation of Akt when PME-1 was knocked down (FIG. 18B). PME-1 over-expression specifically increases the phosphorylation of Akt on T308, but not serine 473 (S473). Importantly, when cells were incubated with upstream inhibitors of Akt phosphorylation (LY294002), there was a decrease in the phospho-forms (FIG. 18B), as expected. Taken together, these data implicate PME-1 to be a positive regulator of the ERK and Akt cancer signaling pathways in EC cells. Activation of both the ERK and Akt signaling pathways has been demonstrated to increase cell proliferation in cancer cells. Importantly, we found that by inhibiting PME-1 activity through decreasing the level of PME-1 protein (via either siRNA or shRNA) there was a decrease in ERK and Akt phosphorylation, which is indicative of decreased cell growth.

Example 17

β-Catenin Phosphorylation

PP2A has been shown to negatively regulate cell migration through the dephosphorylation of β-catenin, protecting it from ubiquitylation and degradation. Because PME-1 has been shown to decrease the association of the B/55α regulatory subunit to the catalytic subunit of PP2A and increased PME-1 seems to promote cell proliferation and EMT, we asked if over-expression of PME-1 in EC cells promoted β-catenin phosphorylation and stabilization.

We performed Western blot analysis in RL95-2 cells that were expressing empty vector (Control), over-expressing PME-1 (+PME-1) or expressing shRNA against PME-1 (−PME-1) (SEQ ID NO: 2) to examine the protein stability of β-catenin (FIG. 19A). We observed a decrease in total β-catenin protein in cells that were over-expressing PME-1. This observation is correlated with the predicted ubiquitylation of β-catenin and its degradation. Conversely, a depletion of PME-1 led to stabilization of total β-catenin (FIG. 19A).

In another series of study, we performed a similar assay in which cells were treated with 10 μM MG-132 prior to protein extraction. MG-132 is a proteasome inhibitor and therefore allows for the accumulation of phosphorylated β-catenin, which is normally quickly degraded, to be detected by western analysis. We found that over-expression of PME-1 increased β-catenin phosphorylation on S45 as well as the secondary phosphorylation sites, S33, S37, and T41 (FIG. 19B) when cells were treated with MG-132. Conversely, we found that decreasing PME-1 levels with shRNA did not lead to an increase in phosphorylated β-catenin when compared to control cells, as expected. These data support our hypothesis that PME-1 regulates β-catenin stability through inhibition of B/55α-dependent PP2A.

Example 18

Expression of EMT Markers

We determined if manipulating PME-1 levels in RL95-2 cells altered expression of EMT markers, such as the epithelial marker, E-cadherin, and mesenchymal markers, vimentin and noggin.

In this study, we transfected RL95-2 cells to express empty vector (Control), over-expressing PME-1 (+PME-1) or expressing shRNA against PME-1 (−PME-1 SEQ ID NO: 2) followed by serum starvation for 24 hours. Afterwards, either vehicle or TGF-β treatment was performed at the end of the 24 hours. TGF-β was used to induce cells to initiate the EMT program. Gene expression analysis was conducted using quantitative real-time PCR.

We discovered that over-expression of PME-1 led to a decrease in E-cadherin expression (FIG. 20A) and a concomitant ~2.5-fold increase in vimentin expression (FIG. 20B), which is consistent with cells undergoing EMT. With TGF-β treatment, the effects of PME-1 over-expression on vimentin levels were more dramatic.

We also noted an increase in Noggin expression (FIG. 20C) when PME-1 was over-expressed compared to control cells. A ~2-fold increase in PME-1 expression was detected in control cells and +PME-1 cells upon addition of TGF-β (FIG. 20D), suggesting that PME-1 is induced by TGF-β stimulation. These data suggest that an increased level of PME-1 induces endometrial cells to undergo EMT.

The Wnt signaling pathway is a well-characterized pathway that contributes to increased cell proliferation, especially EMT (Koval, Drug Disc. Today 17: 1316 (2012). Wnt proteins bind to Frizzled receptors, which are GPCR protein receptors, which signal through β-catenin to increase the expression of genes involved in cell proliferation and EMT (King et al., Cancer Signaling 24:846-851 (2012). We asked if altering the levels of PME-1 affected the expression levels of Wnt signaling inhibitor, such as secreted frizzled-like protein (SFRP1), or Wnt signaling activators, such as Wnt3 and Wnt3A.

Using RL95-2 endometrial cancer cells, we overexpressed PME-1 (FIG. 21A) or depleted PME-1 with shRNA targeted to PME-1 (SEQ ID NO: 2) (FIG. 21B) and confirmed that PME-1 was appropriately expressed. We then examine the relative expression of the Wnt signaling inhibitor, SFRP1, and found that when PME-1 was over-expressed, SFRP1 expression was significantly decreased (FIG. 21C), and when PME-1 was depleted, SFRP1 expression was significantly increased (FIG. 21D). Conversely, when PME-1 was over-expressed, there was a significant increase in expression of Wnt3 and Wnt3A, which are activators of this pathway (FIG. 21E), and that when PME-1 was depleted, Wnt3 and Wnt3A expression were significantly decreased (FIG. 21F). Taken together, these data suggest that PME-1 promotes metastasis through activation of the Wnt signaling pathway.

Example 19

PME-1 Binds PP4 in Addition to PP2A (a) PME-1 Binds to PP2A Via Ppp2ca

We next evaluated the binding affinity of PME-1 to PP2A in endometrial cancer cells. We chose to examine the PME-1 binding domain on PP2A. The catalytic subunit of PP2A is coded by two genes (namely, PPP2CA and PPP2CB), each produces a protein respectively (namely, Ppp2ca and Ppp2cb, also known as α and β isoforms of PP2A, respectively). Ppp2ca and Ppp2cb proteins are 83% identical. At the C-terminus of Ppp2ca and Ppp2cb, they are 100% identical.

To evaluate the binding domain between PME-1 and PP2A, we transfected ECC-1 cells with either (i) empty FLAG vector, (ii) FLAG-PME-1, or (iii) FLAG PME-1 S156A. When the serine (S) residue at the 156 position on PME-1 is mutated to an alanine (A) residue, the PME-1 S156A mutant is catalytically inactive (i.e., no long be able to demethylate PP2A). Following the transfection, we immunoprecipitated using FLAG resin and performed a Western blot on the eluants using various antibodies (i.e., anti-FLAG and anti-Ppp2ca) to determine the binding between PME-1 and Ppp2ca or Ppp2cb.

As shown in FIG. 22A, PME-1 binds (albeit a less degree) to Ppp2ca. A longer exposure (i.e., 2 min, lighter exposure was 10 sec) shows the PME-1 binding. FIG. 22A also show that PME-1 S156A binds to Ppp2ca more strongly. We noted that PME-1 also binds equally well to Ppp2cb (data not shown). We concluded that PME-1 binds to the catalytic subunit of PP2A (i.e., Ppp2ca or Ppp2cb) transiently. The binding of PME-1 S156A is stronger due to its inability to demethylate its substrate.

(b) PME-1 Binds to Another Protein Phosphatase (PP4) Besides PP2A

There are other protein phosphatases in the same family as PP2A in cells that share some similarity to PP2A. In this experiment, we examined if PME-1 binding to Ppp2ca is specific over other phosphatases. We chose to examine phosphatase 4 (PP4) and phosphatase 6 (PP6) since the C-terminal tail of the catalytic subunit of PP2A (i.e., Ppp2ca) is TPDYFL (amino acids 304-309 of SEQ ID NO: 12) (the substrate for PME-1 demethylation) is similar to that of protein phosphatase 4 (i.e., Ppp4c) (VA<u>DYFL</u>) (amino acids 302-307 of SEQ ID NO: 13) and phosphatase 6 (i.e., Ppp6c), (<u>TTPYFL</u>) (amino acids 300-305 of SEQ ID NO: 14), respectively. Specifically, we examined if PME-1 may bind and demethylate PP4 or PP6. PP6 does not seem to be bound by or regulated by PME-1 in EC cells since we could not detect binding between PME-1 or PME-1 S156A with Ppp6c.

In this experiment, we transfected ECC-1 cells with either (i) empty FLAG vector, (ii) FLAG-PME-1, or (iii) FLAG PME-1 S156A. Following the transfection, we immunoprecipitated using FLAG resin and performed a Western blot on the elutants using (i) anti-FLAG, (ii) anti-Ppp4c, and (iii) anti-Ppp6c. As shown in FIG. 22B, PME-1 binds to Ppp4c, but not Ppp6c. We concluded that PME-1 also binds to other phosphatase such as Ppp4c, and predicted that PME-1 may demethylate PP4. Note that Ppp4c shares 68% identity with Ppp2ca/b and Ppp6c shares 70% identity with Ppp2ca/b.

Together, this data provide that PME-1 binds to Ppp2ca or Ppp4c transiently and causes Ppp2ca/Ppp4c to undergo demethylation. We found that the binding of PME-1 to Ppp2ca/Ppp4c is independent of its catalytic activity (i.e., S156A) and that PP6 is not regulated by PME-1 in EC cells.

(c) PME-1 Binds to PP2A with a Stronger Affinity than that of PP4

In this series of study, we co-transfected HEK293T cells with (i) empty V5 vector, (ii) V5-PME-1, or (iii) V5-PME-1 S156A in combination with (i) empty FLAG vector, (ii) FLAG-Ppp2ca, or (iii) FLAG-Ppp4c (FIG. 23). We determined if PME-1 has a higher affinity for PP2A than that of PP4.

We performed a Western blot analysis of the input samples, which are protein lysate samples that are removed and saved for western analysis to determine the starting amount of protein material prior to completing immunoprecipitation. We observed that Ppp2ca and Ppp4c (FLAG antibody) were expressed at equal levels and V5-PME-1 and V5-PME-1 S156A were expressed at equal levels (V5 antibody, FIG. 23A). We then performed a FLAG elution Western blot analysis. We observed that both FLAG-Ppp2ca and FLAG-Ppp4c were immunoprecipitated and expressed at equal levels. We also observed that V5-PME-1 binds at a lower affinity (likely due to a transient interaction) than V5-PME-1 S156A (FIG. 23B). These data suggest that PME-1 has a stronger affinity for binding to PP2A than PP4, because the α-V5 band is stronger for V5-PME-1 S156A when FLAG-Ppp2ca is immunoprecipitated, as compared to that when FLAG-Ppp4c is immunoprecipitated.

(d) Gene Silencing of PME-1 with shPME-1 Treatment Causes Foci Formation

In this series of study, we examined the effects of PME-1 inhibition on cell growth when PP2A, PP4, or PP6 were over-expressed. While PP2A is a tumor suppressor, PP4 promotes tumorigenic phenotypes. Because we identified that PME-1 is able to bind both PP2A and PP4, we tested here if decreased PME-1 levels was beneficial, when PP4 tumor promoting activity was increased. We performed foci formation studies when cells were over-expressing PP2A, PP4, or PP6 and compared the effect of PME-1 in counteracting the tumor promoting effects mediated by PP2A or PP4.

We performed a foci formation analysis by transfecting: (i) empty FLAG vector, (ii) FLAG-PPP2CA, (iii) FLAG-PPP4C, or (iv) FLAG-PPP6C into ECC-1 cells that stably expressed either (i) shSCR (non-targeting shRNA, black bars) or (ii) shPPME1 (depletes PME-1 levels, white bars) (FIG. 24).

As shown in FIG. 24, inhibition of PME-1 leads to a significant decrease in foci formation (i.e., decrease in cell proliferation) as compared to the control (Empty, black bar). In cells transfected with PP2A, PP4 or PP6, inhibition of PME-1 similarly leads to a significant decrease in foci formation (i.e., decrease in cell proliferation). Altogether, these data suggest that gene silencing PME-1 is a valid target for cancer therapy.

Example 20

Chemical Inhibition of PME-1 Leads to Decreased Cancerous Phenotypes (a) PME-1 Inhibitors Directly Bind PME-1

There are several commercially available covalent PME-1 inhibitors that we have analyzed as potential endometrial cancer therapeutics. To confirm that the inhibitors directly bind PME-1, we completed a thermal melt assay. One micromole (1 μmole) of recombinant PME-1_des3, of which the last 3 amino acids are deleted, were pre-incubated with SYBR orange in the presence of 50 μM ABL-127 (a potent covalent PME-1 inhibitor, squares) or 0.05% DMSO (vehicle, circles) for 10 minutes (FIG. 25) at 37° C. We then performed a thermal gradient, increasing the temperature by 2° C. each minute from 37° C. to 95° C. and fluorescent signal was detected at 492-601 nm on a thermal cycler. The increase in Tm from ~55° C. (PME-1+DMSO, circles) to ~65° C. (PME-1+ABL-127, squares) indicated thermal stabilization of the PME-1 protein via direct binding of the ABL-127 inhibitor (FIG. 25).

(b) PME-1 Inhibition Leads to Decreased Cell Proliferation

In order to determine if compound-based inhibition of PME-1 decreased cell proliferation as we showed with RNAi-based depletion of PME-1, we completed a foci formation assay, as before (FIG. 10), using the covalent inhibitors of PME-1, ABL-127 and AMZ-30. This study was completed in Ishikawa endometrial cancer cells. As shown in FIG. 26, DMSO served as the vehicle control (set to 100%) and Ishikawa cells were treated with 50 nM ABL-127 or 25 μM AMZ-30 every 2-3 days for a total of 10 days. shSCR- and shPPME1-treated cells were used for comparison and were normalized to untreated treated cells (not shown) set to 100%.

We found that treating Ishikawa cells with the covalent PME-1 inhibitors, ABL-127 and AMZ-30 led to ~50% decrease in the amount of foci that were formed, indicating significant decreases in cell proliferation (FIG. 26). A similar reduction in foci was seen when PME-1 was depleted with shRNA, suggesting that chemical inhibition of PME-1 is also beneficial in endometrial cancer cell lines.

(c) PME-1 Inhibition Leads to Decreased Cell Migration

We next asked if PME-1 inhibition led to decreased cell migration by completing a trans-well migration assay. Cells were synchronized for 24 hours in media containing 0% FBS. For this experiment, DMSO was again used as the vehicle control and Ishikawa cells were treated with DMSO (control) or 50 nM ABL-127 or 20 μM AMZ-30 for 24 hr and were allowed to migrate through a collagen-coated well towards the bottom chamber, containing media with 30% FBS. As shown in FIG. 27, there is a dramatic decrease in the percentage of cells that are capable of migrating when PME-1 is inhibited with either covalent inhibitor. Taken together, these data suggest that PME-1 inhibition leads to decreased cancer phenotypes.

Example 21

Mice Study—Gene Silencing PME-1 Suppresses Tumor Formation

Because our data suggest that PME-1 promotes more aggressive EC, we asked if the over-expression of PME-1 in EC cells promoted the formation of tumors in a xenograft model. In this study, instead of RL95-2 cells, which require a larger number of cells to induce tumor formation, we used ECC-1 cells, which are aggressive endometrial adenocarcinoma cells with high levels of endogenous PME-1 (See FIG. 1) that have been used previously for similar studies.

ECC-1 cells expressing either the empty vector (control) or over-expressing PME-1 (+PME-1) were subcutaneously injected into the flank of seven female immune-compromised mice per group and tumor size was measured weekly. Prior to injection, we performed Western blot analysis to confirm the proper expression of PME-1 (FIG. 28A).

Mice injected with +PME-1 cells formed tumors with a significantly larger tumor volume compared to control mice by 7 weeks post injection (FIG. 28B). Tumor bulks were visually larger when PME-1 was over expressed (white bars represent 0.5 cm, FIG. 28C) and mean tumor weight was increased in +PME-1 cells compared to control mice (FIG. 28D). These in vivo data correlate well with our in vitro data and further substantiate our hypothesis that PME-1 promotes more aggressive cancer growth and cell proliferation.

We next asked if depletion of PME-1 with shRNA led to decreased tumor growth. For this study, we subcutaneously injected $5\times10^6$ Ishikawa cells into the flank of female SCID mice and allowed the tumors to grow until they reached a tumor volume of approximately 400 mm$^3$. Once tumors reached the appropriate size; we randomly divided the mice into two groups and injected them with adenovirus expressing either scrambled shRNA (Control-Ad, closed circles) or PPME1-shRNA (SEQ ID NO: 3) (open circles). Tumors were treated every three to four days with $5\times10^7$ pfu (on days 0, 3, 7, 10, and 13). As shown in FIG. 29, by day 13 there was a significant reduction in tumor volume when PME-1 was depleted with shRNA (open circles) compared to control shRNA (closed circles). Taken together, these data suggest that the levels of PME-1 expression affect tumor growth and that depletion of PME-1 leads to decreased tumor growth.

Example 22

Mice Study—Gene Silencing PME-1 Decreases PME-1 Protein Expression Levels (a) Western Blot Analysis We asked whether PME-1 protein was effectively knocked-down in the mice from the xenograft study (Example 21 and FIG. 29). In this study, the mice were euthanized and tumors were resected. Each tumor was cut into two halves. One half of each tumor was flash frozen in liquid nitrogen for protein analysis, and the other half was stored in formalin for immunohistochemistry (IHC) and immunofluorescence (IF) microscopy.

Total protein was then extracted from the flash-frozen tumors, which we used in the Western Blot analysis. We completed densitometry to quantify the relative amount of PME-1 protein normalized to the house-keeping protein, GAPDH. FIG. 30 shows that the tumors we treated with shPPME1 adenovirus (white bar) expressed 40% less PME-1 protein when compared to tumors that we treated with shSCR (black bar). These results suggest that the adenovirus-treatment with shPPME1 led to a decrease in total PME-1 protein. Taken together with the decrease in tumor volume from Example 21, these data suggest that treatment with shPPME1 causes a decrease in PME-1 protein, which in turn decreases tumor growth.

(b) Immunohistochemistry Analysis—PME-1 Depletion

In this study, we sought to verify that PME-1 was depleted in tumors treated with shPPME1 adenovirus. We embedded the formalin-fixed tumors bulks and sectioned the tumor tissues and affixed the tumor tissues to slides for analysis.

FIGS. 31A and 31B are exemplary slides of tumor tissues for the immunohistochemistry (IHC) analysis. In the analysis, we first stained the tumors with hematoxylin and eosin stain (H&E stain) followed by the α-PME-1 antibody. Brown-colored staining indicated PME-1 positivity. We observed that PME-1 was present in the cytoplasm of the cells. In particular, FIG. 31B depicted a decrease in PME-1 positive cells when the tumor tissue was treated with shRNA, suggesting that PME-1 protein was depleted when treated with shRNA, when compared to control shRNA in FIG. 31A. The control depicted a greater amount of brown-colored staining, indicating PME-1 positivity.

All slides were further analyzed by a pathologist who assigned each tumor slide a percentage of PME-1 positivity. All PME-1 percentages were then quantified for each treatment group and the results are depicted in FIG. 31C. A ~40% decrease in PME-1 protein was also shown by IHC analysis when tumors were treated with shRNA against PME-1.

(c) Immunohistochemistry Analysis—Effects of PME-1 Depletion

We analyzed the tumor tissue by IHC to determine if PME-1 levels affected the rate of tumor cell death and tumor cell proliferation. To perform the analysis, we first stained the tumors with hematoxylin and eosin stain (H&E stain), which is commonly used to detect tumor necrosis (tumor cell death). FIG. 32A is a representative image of a tumor undergoing tumor necrosis, which is indicated by pink staining.

We analyzed the tumor sections for p53 positivity by staining the tissue with α-p53 antibodies. In endometrial adenocarcinomas, p53 positivity is indicative of cells that are actively proliferating. The representative image, FIG. 32B, depicts cells that are actively dying, which is shown by the brown-color which we obtained by staining with α-p53 antibodies.

The slides of the tumor tissues were also analyzed by a pathologist who assigned each slide a percentage score, representing the amount of tumor necrosis or the amount of p53-positivity, for each tumor. We compiled the data and quantified the amount of tumor necrosis and tumor cell proliferation when PME-1 levels were altered. FIG. 32C provides a graphical representation of the compilation of data. The data shows that there was ~3-fold increase in tumor necrosis when cells were treated with shRNA, suggesting that PME-1 was depleted with shRNA, (black bars). Interestingly, when PME-1 was depleted with shRNA, there was a concomitant 2-fold decrease in p53-positivity (i.e. decreased tumor cell proliferation, white bars). Taken together, these data suggest that: (1) PME-1 protein was efficiently decreased upon intratumoral treatment with shPPME1 and (2) decreased PME-1 protein correlated with increased tumor cell death and decreased tumor cell proliferation, suggesting that depletion of PME-1 leads to tumor death and decreased growth.

Example 23

Mice Study—Depletion of PME-1 Causes Cell Death

Since our results indicated that depletion of PME-1 led to increased tumor cell death, we asked if tumor cells were undergoing apoptosis or programmed cell death. In this study, we performed an immunofluorescence analysis. To do so, we first stained tumor tissue sections with the nuclear stain, DAPI, and then with a TUNEL stain, so as to stain apoptotic cells; after which we observed the staining under a fluorescence microscope. We observed regions of cell apoptosis in tumors tissue that was treated with shSCR (See FIGS. 33A and 33B). We hypothesize that these results are likely due to regions of cells that did not have access to a blood supply. Importantly, we observed that apoptotic regions were more expansive throughout tumors treated with shPPME1 (See FIGS. 33C and 33D). These data suggest that PME-1 depletion leads to increased tumor cell apoptosis.

Since it is known that PME-1 demethylates the tumor suppressor, PP2A, on the C-terminal leucine residue (L309)

of its catalytic subunit, inactivating PP2A. In the next study, we questioned whether we would observe a decrease in the amount of demethylated (inactive) PP2A and an increase in methylated (active) PP2A when PME-1 is inhibited or depleted. To determine if this was the case, we performed immunofluorescence microscopy analysis of the tumor sections using antibodies specific for the demethylated form of PP2A (See FIG. 34) or the methylated form of PP2A (See FIG. 35).

FIGS. 34A-34F depict representative images from tumor sections that we treated with scrambled shRNA or control shRNA (See FIG. 34A-C) or shRNA targeting PME-1 (SEQ ID NO: 3) (See FIG. 34D-F). We stained the tumor sections with DAPI, a nuclear stain (blue), α-PME-1 (green), and α-demethylated PP2A (red). We observed that cells that were positive for PME-1 (FIG. 34B) were also positive for demethylated PP2A (FIG. 34C) and cells that were treated with shPPME1 had fewer PME-1 positive cells (compare FIG. 34B to 34E). We also observed that when there was PME-1 depletion in cells, there were also fewer cells positive for the inactive, demethylated form of PP2A (compare FIG. 34C to 34F).

We next examined the relative levels of active, methylated PP2A when PME-1 was depleted with shRNA using immunofluorescence microscopy analysis (FIG. 35). We stained tumor sections with the nuclear stain, DAPI (blue, FIGS. 35A and 33C) and α-methylated PP2A antibody (green, FIGS. 35B and 35D). Surprisingly, we observed higher levels of methylated PP2A present at the lining of glandular structures in all of our samples (See, FIG. 35B), but an additional increase in methylated PP2A in tumors treated with shPPME1 (SEQ ID NO: 3) throughout the tumor bulk (See, FIG. 35D), which suggests an increase in active PP2A when PME-1 is depleted. Taken together, these data suggest that inhibition or depletion of PP2A will lead to the increase of PP2A methylation and therefore increased PP2A tumor suppressor activity.

Example 24

PME-1 Effects on Triple Negative Breast Cancer

Because our previous Examples have shown depletion of PME-1 in endometrial cancer cell lines and xenograft models leads to decreased cancerous phenotypes, we next questioned if depletion of PME-1 in other types of cancer would have a similar effect. To address our question, we designed a study around triple negative breast cancer.

We performed a xenograft study using a triple negative breast cancer cell line (i.e., MDA-MB-231) expressing luciferase ("Luc2"). We introduced $2\times10^6$ of the MDA-MB-231-Luc2 cells with Matrigel into the flank of female SCID mice, allowing the tumors to grow to ~150 mm$^3$. We then intratumorally injected the tumors with $5\times10^7$ pfu of adenovirus, delivering either scrambled shRNA or shRNA targeted against PME-1 (SEQ ID NO: 3) to the tumor bulk.

In this study, we used the luciferase signal intensity as a direct read-out of tumor cell viability. We treated tumor bulks with shRNA at time 0 hours and then measured the luciferase signal. We measured the signal again at intervals of 6 hours, 28 hours and 52 hours post-treatment. We observed a significant decrease in luciferase signal (or total flux) within 52 hours after one treatment with shPPME1 (See FIG. 36). The significant decrease of luciferase signaling we observed suggests a decrease in breast cancer tumor growth when treated with shPPME1, which was similarly observed in endometrial cancer cells (Example 22). Taken together, the data we obtained in this study suggests that the administration of shPPME1 inhibited or depleted PME-1 in malignant breast cancer tumors. As such, the administration of shPPME1 to breast cancer tumors is a novel method of breast cancer treatment.

EXPERIMENTAL METHODS AND PROTOCOLS

A) Maintenance of Cell Cultures

Cell lines were purchased from ATCC. RL95-2 cells were maintained in Dulbecco Modified Eagle medium and Ham's F-12 supplement (DMEM:F12, Sigma Aldrich) with 10% fetal bovine serum (FBS, Sigma Aldrich), 5 µg/ml insulin (Sigma Aldrich), and 100 µg/m1Primocin (InvivoGen). KLE cells were maintained in Dulbecco Modified Eagle medium and Ham's F-12 supplement (DMEM:F12) with 10% fetal bovine serum (FBS), and 100 µg/ml Primocin. ECC-1 cells were maintained in RPMI-1640 medium (Sigma Aldrich), supplemented with 10% FBS. Ishikawa cells End1 immortalized endocervical cells were maintained in keratinocyte-serum free medium (KSFM, Life Technologies) with bovine pituitary extract, human epithelial growth factor (Life Technologies), and 10% FBS according to ATCC's recommendations.

B) Creation and Maintenance of Stable Cell Lines

N-terminal FLAG-tagged vector (p3XFLAG-CMV-10, cat. no. E7658; Signa-Aldrich, St. Louis, Mo.) were transfected into RL95-2 cells with Lipofectamine 2000 (Life Technologies). The PME-1 gene was cloned into the vector within the multi-cloning site with EcoR1 and BamH1 restriction enzyme sites and inserted. Proper orientation of the gene was confirmed with sequencing, and empty vector was used as a control.

Lentivirus was produced in HEK293T cell lines with pLKO shRNA vectors (Thermo Scientific, cat. no. RHS4533; Waltham, Mass.) and pCDH-CuO-GFP-Puro vectors (System Biosciences, Inc., cat. no. QM513B-1; Mountain View, Calif.) with pPACKH1 packaging plasmid (System Biosciences, Inc., cat, no. LV050A-1). shRNA sequences are in the Table 2. Lentivirus was collected and concentrated with Peg-IT concentrating solution (System Biosciences, Inc.). $5\times10^6$ pfu/ml lentivirus was added to cell cultures with growth media and 8 µg/ml PolyBrene (Sigma Aldrich). Media was changed to full growth media after 24 hrs and to selection media containing antibiotic after 48 hrs (5 µg/ml puromycin) (Invivogen) for 10 days.

C) RNA Extraction from Endometrial Cancer (EC) Patient Tissues

Matched pairs harvested from 30 patients with endometrial adenocarcinoma (see Table 1 for patient information) were used to determine the mRNA and protein levels of PME-1 in tumor versus normal adjacent tissue. Tissue samples were homogenized in 4 mL TRIzol Reagent (Invitrogen) on ice and RNA and protein were extracted according to standard procedures. Briefly, samples were centrifuged at 10,000×g for 15 minutes at 4° C. and the supernatant was subjected to chloroform extraction. The aqueous layer was subsequently used to isolate RNA by precipitation with isopropanol while the interphase/organic phase was saved at 4° C. for protein extraction.

D) Protein Extraction from EC Patient Tissues

The protein was extracted by precipitation with acetone followed by centrifugation at 12,000×g for 10 minutes at 4°

C. The pellets were washed with of 0.3M guanidine hydrochloride/95% ethanol/2.5% glycerol (v/v) solution and 2.5% glycerol/95% ethanol, air-dried, re-suspended in 300 µl of 1% SDS and heated at 100° C. to solubilize protein. Protein concentrations were determined using Bio-Rad Protein Assay Dye Reagent Concentrate (Bio-Rad) on a SPECTRA Max plus spectrophotometer (Molecular Devices) at 595 nm wavelength.

E) qRT-PCR Analysis of Gene Expression in EC Patient Tissues

Gene expression analysis was conducted using the one-step SYBR green kit (Qiagen) as described in the manual. The following primers were used for amplification at 5 µM per reaction: PME1-Forward 5'-AGGAAGGAAGTGAGTCTATAAG-3' and PME-1-Reverse 5'-CAGGTGTATGGATGGTCTT-3'. All data was normalized to 18S house-keeping gene. 18S primers were Forward 5'-AACCCGTTGAACCCCATT-3' and Reverse 5'-CCATCCAATCGGTAGTAGCG-3'. All data was normalized to RL95-2 cells to minimize plate-to-plate variance and fold-change is represented.

F) Taqman RT-PCR Analysis

Total RNA was extracted with Qiagen RNAEasy kit from RL95-2 cells. cDNA was synthesized using 500 ng-1 µg of RNA and SuperScript VILO c-DNA mix (Life Technologies). Taqman probes and PCR-mix were purchased from Life Technologies. All samples were run in triplicates. Results are representative of three independent experiments in which genes of interest were normalized to the house-keeping gene, 18S or GAPDH, where fold-change was calculated using the ddCt method.

G) Western Analysis of EC Patient Tissues and Xenograft Tumors

15 µg of protein was used for western analysis. PME-1 antibody (Santa Cruz) and COXIV (Cell Signaling Technologies) were used for detection of proteins and the blots were developed using chemiluminescence (Pierce ECL Western Blotting Substrate—Thermo Scientific) on the GE ImageQuant LAS 4000. For analysis of Akt, ERK, and β-catenin signaling in tissue culture, western analyses were completed as follows. RL95-2 cells stably infected with lentivirus expressing constructs were selected with puromycin (Invivogen). The cells were incubated with either 50 µM Akt inhibitor (LY 294002, Cell Signaling Technologies) or 40 µM ERK inhibitor (V0126, Cell Signaling Technologies) for 1-2 hours at 37° C. 1.5× Laemelli buffer (0.5 M Tris pH6.8, 100% glycerol, 10% sodium dodecyl sulfate, 100 mM EDTA) was used to prepare cell lysates. 20 µg of protein was used for western analysis. Primary antibodies used were: P-Akt (Ser473), P-Akt (Thr308), pan-Akt, P-ERK (Thr202/204), total ERK (Cell Signaling Technologies), PME-1 (Santa Cruz), phospho-β-catenin (Ser45, Cell Signaling Technologies), phospho-β-catenin (Ser33/37/Thr41, Cell Signaling Technologies), β-catenin (Abcam), DcR2 (Abcam), and GAPDH (Abcam). All experiments were repeated several times with similar results.

Flash-frozen tumors harvested from xenograft models were processed as follows: Tissues were ground into a powder in liquid nitrogen then transferred to a 50 ml tube containing lysis buffer (20 mM Tris pH7.5, 150 mM NaCl, 1 mM EDTA, 1 mM EGTA, 1% Triton X-100, 100 µl Protease Inhibitor II (Sigma Aldrich), 100 µl Protease Inhibitor III (Sigma Aldrich), and 1 Protease Inhibitor tablet (Roche)). The tissue solution was homogenized, incubated on ice for 30 minutes, and the centrifuged at 4° C. for 10 minutes. The supernatant was aliquotted and protein was quantified using Bradford solution (Bio-Rad). Western protein analysis was run with 50 µg of protein loaded into a 10% SDS-PAGE reducing gel. Antibodies were probed overnight at 4° C. Antibodies used include anti-GAPDH (Abcam ab9485) and anti-PME-1 (Santa Cruz sc-20086, sc-55472).

H) Immunohistochemistry Analysis of EC Patient Tissues and Xenograft Tumors

Patient tissues representative of stages I, II and III endometrial adenocarcinoma and normal adjacent tissue were fixed for 3 hours on ice in 4% PFA, followed by 30% sucrose in PBS and were then embedded in OCT (SAKURA), frozen on dry ice and sectioned to 10 µm slices using the cryostat (Microm HM 550). To stain, sections were incubated in methanol (Sigma Aldrich) with 0.3% hydrogen peroxide (Sigma Aldrich) to block endogenous peroxidase, washed and blocked again in 10% FBS in TBST (Tris Buffered Saline with 0.1% Triton X-100). The sections were subsequently incubated with primary antibody over night, followed by detection using VECTASTAIN Elite ABC biotyn-avidin-HRP kit (Vector Labs) and DAB. H&E staining was performed according to standard protocol. Primary antibodies include anti-PME-1 antibody (Antibodies-online).

Formalin-fixed tumors harvested from xenograft models were processed as follows: Tissues were fixed for three hours on ice in 4% PFA, followed by 30% sucrose in PBS and were then frozen. Samples were then fixed in 10% NBF for 72 hr and processed overnight on the ES Shandon Tissue Processor (Thermo Scientific) as follows: 2 hr in 10% neutral buffered formalin, 1 hr in 70% ethanol, 1 hr in 80% ethanol, 1 hr in 95% ethanol, 3 hr in 100% ethanol, 2 hr in wax at 62° C., and were then embedded in paraffin and cut to 4 µm sections. Sections were incubated with α-PPME1 (Antibodies-online) at 1:200 in TBS, surfactant and protein stabilizer with 0.35% ProClin™ 950 (Leica Biosystems). Samples were then processed using the Bond Polymer Refine Detection kit (Leica Biosystems) according to manufacturer's protocol. Images were obtained using the Nikon ECLIPSE 50i microscope with a 40× objective.

I) Immunofluorescence Assays

For analysis of patient samples, tissues were blocked for 2 hours with 10% FBS in TBST for at RT, incubated with each primary antibody (together) overnight at 4° C., washed three times for 15 min in TBST, incubated with each secondary fluorescent antibody (together) for 1 hr at RT, washed again as above, stained with DAPI and mounted with cover-slips using vectashield mounting media (Vector Labs). Primary antibodies used were for PME-1 (Santa Cruz), E-cadherin (Millipore), and vimentin (Genscript). $1\times10^3$RL95-2 cells were plated on a chamber slide and were incubated overnight at 37° C. Slides were fixed with 4% paraformaldehyde (PFA) on ice for two hours. The cells were incubated with the primary antibody to Histone 3 (pH3) phosphorylated at Ser10 (1:200, Cell Signaling Technologies) overnight and developed with the secondary anti-rabbit Alexa-Fluor 555 antibody (Cell Signaling Technologies). DAPI was used as a nuclear counter-stain (Sigma Aldrich). Images were taken with the Nikon Eclipse TE2000 at 20×.

For analysis of tumors produced in xenograft studies, samples were fixed and paraffin embedded onto slides then rehydrated through a series of xylene and ethanol solutions: 100% xylene (twice), 50% xylene 50% ethanol, 100% ethanol, 95% ethanol, 70% ethanol, 50% ethanol, and finally cold running tap water. 10 mM sodium citrate pH 6.0 was used for antigen retrieval. Slides were microwaved for 20 minutes in the sodium citrate solution and allowed to cool in the microwave for another 20 minutes and rinsed with 1×TBST with 2% BSA three times. Slides were blocked at room temperature with TBST with 10% FBS and 1% BSA. Primary antibodies were diluted in blocking buffer and include anti-PME-1 (Antibodies Online ABIN489617) and anti-PP2CA L309 deMe (Santa Cruz sc-14020) or anti-PP2A-alpha methyl L309 (Abcam ab66597) with anti-Mouse IgG-Alexa Fluor-488 (Cell Signaling Technologies). Secondary antibodies were also diluted in blocking buffer and include anti-Rabbit IgG-Alexa Fluor-555 and anti-Mouse IgG-Alexa Fluor-488 (Cell Signaling Technologies). DAPI nuclear stain (Cell Signaling Technologies) was added followed by mounting with VectaMount (Vector Laboratories).

J) Foci Formation Assays 1,000 cells were plated in a six well tissue culture dish in selection media (to include 5 µg/ml puromycin) (Invivo-Gen). Cells were allowed to adhere and grow in a 5% $CO_2$, 37° C. incubator for 10 to 14 days. Media was replaced every fourth day. Cells were stained with 1% crystal violet (Sigma Aldrich) for five minutes and rinsed with PBS. Colonies were counted and data is presented as the percentage of change compared to the control. All Experiments were repeated at least three times.

K) TUNEL Assay

RL95-2 cells were plated in a chamber-slide and allowed to grow over night at 37° C. Cells were transfected the next day with 100 nM of siRNA (Thermo Scientific) using Dharmafect 1 transfection reagent (siRNA sequences are summarized in Table S2). Transfections were repeated on day four and the cultures were terminated the day after. The assay was performed according to the manufacturer's instructions (Roche Applied Science, counterstained with DAPI and photographed using Leica DM16000 B microscope. Cells incubated with 1 U/µl of DNase I (Life Technologies) served as a positive control. The experiment was repeated three times.

For TUNEL assays on tumors resected from the xenograft model, samples were fixed and paraffin embedded onto slides then rehydrated through a series of xylene and ethanol solutions: 100% xylene (twice), 50% xylene 50% ethanol, 100% ethanol, 95% ethanol, 70% ethanol, 50% ethanol, and finally cold running tap water. 10 mM sodium citrate pH 6.0 was used for antigen retrieval. Slides were microwaved for 20 minutes in the sodium citrate solution and allowed to cool in the microwave for another 20 minutes and rinsed with 1×TBST with 2% BSA three times. Positive control sections were treated with DNase I (Life Technologies) for 10 minutes at room temperature. TUNEL assay was carried out following protocol from Roche In Situ Death Detection Kit, Fluorescein. DAPI nuclear stain was added following the TUNEL protocol (Cell Signaling Technologies). Slides were mounted with VectaMount (Vector Laboratories). Images were taken on a Leica DMI 6000 B microscopes at 20× objective.

L) Invasive Growth Assay in Matrigel

The 3D On Top Matrigel Assay was completed in 24 well dishes. Briefly, the bottoms of 24 well dishes were coated with 50 µl BD Matrigel Basement Matrix Phenol Red Free (BD Biosciences cat. #356237) and allowed to solidify at 37° C. $10^5$ cells were suspended in 250 µl chilled medium containing either 10 ng/ml of TGF-b or vehicle and allowed to settle at 37° C. for 30 minutes. Chilled medium containing 10% of Matrigel was added by pipetting gently down the sidewall of the well and incubated at 37° C. for ten days changing top medium every second day. Colony counts were performed on the tenth day; averages were taken from three fields of view using a 10× objective. Experiment was repeated three times.

M) Phosphatase Assay

Whole cell lysates were used with the DuoSet IC PP2A Phosphatase Assay Kit (R&D Systems). Procedure was carried out as per kit instructions with 500 µg protein and the absorbance was measured at 620 nm. The assay was repeated twice with similar results.

N) In Vivo Tumor Formation

For the PME-1 over-expression in vivo study, $1 \times 10^6$ endometrial carcinoma cells (ECC-1) diluted in 100 µl 1×PBS expressing empty vector (Control) or over-expressing PME-1 (+PME-1) were injected subcutaneously into the flank of immune-compromised female mice (n=7 per group). Tumor formation was measured weekly for seven weeks with a caliper and tumor volume was calculated according to the formula $V=\frac{1}{2}yx^2$, where y=tumor length and x=tumor width. At 8 weeks post-injection, mice were euthanized and tumors were resected for analysis. Tumor masses were weighed and were homogenized in TriZol reagent, as above, for protein extraction.

For the PME-1 depletion in vivo assay, $5 \times 10^6$ Ishikawa cells and Matrigel were subcutaneously injected into the flank of female SCID mice (n=14) and allowed the tumors to grow until they reached a tumor volume of about 400 $mm^3$. Once tumors reached the appropriate size, mice were randomly divided into two groups and were injected with adenovirus expressing either scrambled shRNA (Control-Ad, closed circles) or PPME1-shRNA (open circles). Tumors were treated on days 0, 3, 7, 10, and 13 with $5 \times 10^7$ pfu. Tumors were measured as above and were resected for further analysis. Tumors were cut in half to complete western analysis and IHC.

For the PME-1 depletion in vivo assay, using a triple negative breast cancer cell line, $2 \times 10^6$ MDA-MB-231-Luc D3H2LN cells were injected with Matrigel subcutaneously into flanks of C.B.17 SCID mice. Tumors were allowed to form and were measured with calipers twice a week until they reached 150 $mm^3$. $5 \times 10^7$ pfu of adenovirus were injected into tumors at time-point 0 and tumor volume is monitored by IVIS Series Pre-clinical in vivo Imaging System (PerkinElmer) and measured in total flux (photons/sec).

All animal work was approved by and conducted according to the guidelines of the Genesis Biotechnology Group IACUC.

O) BrDU Incorporation Assay

The BrDU Incorporation assay was completed with RL95-2 cell lines in media supplemented with 2.5 µg/ml puromycin. Cells were plated at $0.5 \times 10^4$ cells per well into a 96 well dish with 0% FBS and allowed to settle for 24 hours. The assay was completed as per kit instructions (Roche, Cell Proliferation ELISA, BrdU colorimetric cat. #11647229001). Briefly, 10 uM BrdU was added to the cells, 24 hours later cells were fixed and denatured with FixDenat from the kit and allowed to incubate with anti-BrdU antibody for up to two hours. Following the incubation and addition of the kit substrate, absorbances were read using FluoStar Galaxy.

P) Thermal Melt Assay

The assay was completed by first conducting a 10 min pre-incubation of one µmole of recombinant PME-1des3 with 50 µM ABL127 (Sigma) or vehicle (0.05% DMSO) in the presence of SYBR Orange (1:1,000, v/v, Sigma) at 37° C. in 1×NEB buffer 2 (50 mM NaCl, 10 mM Tris-HCl, 10 mM $MgCl_2$, 1 mM DTT, pH 7.9 at 25° C.), a thermal gradient was performed increasing temperature by 2° C. per minute increments from 37° to 95° C. and fluorescence (492 nm-610 nm) was acquired on a thermal cycler Mx3005P (Stratagene).

Q) Trans-Well Migration Assay

The assay was completed with ECC-1 endometrial carcinoma cell lines following kit instructions Cultrex 96 Well Collagen IV Cell Invasion Assay (cat #3458-096-K). Briefly, cells were serum starved for 24 hours prior to experimentation, then counted and put into the top chamber of a collagen type IV coated Transwell membrane at a concentration of $1 \times 10^6$ cells/well in 0% FBS. The bottom chamber contained 30% FBS. Cells were allowed to invade at 37° C. humid chamber incubator for 24 hours. Cells that invaded were analyzed using the kit provided Calcein-AM and fluorescence was read using FluoStar Galaxy.

R) shRNA Constructs shRNAs were designed to reduce the mRNA expression and protein activity of PME-1 by selecting specific targeting sequences against PME-1. The human PME-1 gene is provided in NM_016147.1, the disclosure of which in incorporated by reference. Target sequences for PME-1 were designed to reduce the gene expression of PME-1. The shRNAs were constructed based on an adenoviral backbone (e.g., adenoviral-Type 5 (dE1/E3)). The shRNAs were obtained from Vector BioLabs (Philadelphia, Pa.). The construct name is Ad-GFP-U6-hPPME1-shRNA. The full length of exemplary shRNA include SEQ ID NOs: 7, 8 and 9, which contain the following target sequences for PME-1: SEQ ID NO: 1 (GTACAGCTATGGATGCACTTA), SEQ ID NO: 2 (GCAGCGATTATTAGTAGAGT T) and SEQ ID NO: 3 (GGTGTTGATAGATTGGATAAA), respectively.

S) Control siRNA and shRNA

Control siRNA or shRNA all have scrambled sequences and they do not elicit any effects on PME-1 mRNA in cells. Control siRNA or shRNA are commercially available, for example, control siRNA such as siGENOME ON-TARGETplus SMARTpool#1 from Dharmacon (GE Lifesciences) (cat # D-001206-13-20). Lentiviral shRNA controls include pLKO.1 lentiviral shRNA empty vector control from Open Biosystems (cat # RHS4080). Adenoviral shRNA control includes Adenovirus shRNA Control from Vector Biolabs (cat #1122N). In this application, SEQ ID Nos. 1 and 2 are PPME1-specific lentiviral shRNAs obtained from Thermoscientific. SEQ ID No. 4 is an siRNA obtained from Dharmacon (GE Life Sciences). We custom designed and synthesized the SEQ ID NOs, 5 and 6 as PPME1 siRNA with 3'UTR" attachment using Dharmacon's free online software (cat # PUSMA-000001/3).

T) siRNA Targeted Against PME-1 Gene siRNA is designed to reduce the PME-1 mRNA, thereby inhibit EMT and tumor proliferation of endometrial cancer and breast cancer. siRNA targets the PME-1 gene or 3'-UTR causing the reduction of PME-1 mRNA. Exemplary target sequences include SEQ NO: 4 (TGG CTG GTG TTG ATA GAT T), SEQ ID NO: 5 (GTG GAT AGC ATC ACA AGA A) and SEQ ID NO: 6 (GTA AAT ACG TCG CAC CAG A). The corresponding siRNA sequences are SEQ ID NO:15 (UGG CUG GUG UUG AUA GAU U), SEQ ID NO: 16 (GUG GAU AGC AUC ACA AGA A) and SEQ ID NO: 17 (GUA AAU ACG UCG CAC CAG A).

U) Statistical Analysis

Statistical analysis was completed using GraphPad Prism software. For animal studies, significance was calculated using a two-way ANOVA. For all other data, analysis was completed with the Mann-Whitney U test for significance (patient samples) or the student's standard t test; standard errors of the mean (SEM) were calculated for all sample batches. The p values were represented as follows: *$p<0.05$, p *$p<0.001$. ROC analysis plotting the sensitivity and specificity of PME-1 mRNA levels in endometrial cancer patient samples (as shown in FIG. 3A) was calculated with 95% confidence interval to determine the validity of PME-1 as a biomarker for endometrial cancer using a likelihood ratio of 21. The determined p value ($p<0.0001$) and area under the curve (AUC, 0.9601) suggests that PME-1 could be a valuable predictor of endometrial cancer.

All publications and patents cited in this specification are herein incorporated by reference in their entirety. Various modifications and variations of the described composition, method, and systems of the invention will be apparent to those skilled in the art without departing from the scope and spirit of the invention. Although the invention has been described in connection with specific preferred embodiments and certain working examples, it should be understood that the invention as claimed should not be unduly limited to such specific embodiments.

TABLE 1

Patient Information

| Patient ID | Age | FIGO Grade | TNM Class | Tumor size (cm) | Metastases | PPME1 |
|---|---|---|---|---|---|---|
| 06310 | 71 | 1 | T3aN0M0 | N/A | ovary | +14.42 |
| 06309 | 71 | 1 | T1bN0M0 | 6.5 × 4 × 5 | none | +2.235 |
| 06308 | 57 | 1 | T3aN0M0 | N/A | ovary | +7.111 |
| 06276 | 57 | 1 | T1bN0M0 | N/A | ovary | +7.945 |
| 06261 | 58 | 1 | T3aN0M0 | N/A | none | +24.93 |
| 06273 | 69 | 1 | T1aN0M0 | N/A | none | +17.51 |
| 06272 | 79 | 1 | T1bN0M0 | N/A | none | +8.456 |
| 06287 | 66 | 1 | T1bN0M0 | 1 × 2 × 3.8 | none | −2.809 |
| 06313 | 58 | 1 | T2N0M0 | 3.8 × 3.5 × 1 | none | +2.144 |
| 06314 | 70 | 1 | T1bN0M0 | 5.5 × 6 × 2 | none | +4.724 |
| 06337 | 61 | 1 | T1bN0M0 | 3 × 3.5 | none | +2.329 |
| 06354 | 62 | 1 | T1aN0M0 | 6 × 4.5 × 2 | none | +2.549 |
| 06262 | 66 | 1 | T1aN0M0 | N/A | none | −2.219 |
| 06246 | 56 | 1-2 | T1aN0M0 | 3 × 5 × 0.8 | none | +2.657 |
| 06240 | 59 | 2 | T1bN0M0 | 3.5 × 2 × 1.5 | none | +5.242 |
| 06241 | 58 | 2 | T1aN0M0 | N/A | none | +3.555 |
| 06245 | 82 | 2 | T1bN0M0 | N/A | none | +8.877 |
| 06247 | 64 | 2 | T1aN0M0 | 5.5 × 1.5 × 1 | none | −5.856 |
| 06319 | 52 | 2 | T1aN0M0 | 3.5 × 2.5 × 2 | none | +32.67 |
| 06333 | 66 | 2 | T1aN0M0 | 1.1 × 0.8 × 1 | none | +26.91 |
| 06336 | 56 | 2 | T1bN0M0 | 7 × 6 × 3 | none | +2.402 |
| 06384 | 53 | 2 | T2N0M0 | 6 × 5 × 2 | none | +9.987 |
| 06387 | 70 | 2 | T1aN0M0 | 2.5 × 2.5 × 0.6 | none | +2.639 |
| 06269 | 61 | 2 | T1aN0M0 | 0.4 | none | +30.48 |
| 06248 | 52 | 2 | T1aN0M0 | 4 × 3.5 | none | −2.999 |
| 06268 | 65 | 3 | T1bN0M0 | 4 × 2 | none | +12.47 |
| 06294 | 41 | 3 | T1aN0M0 | N/A | none | +4.993 |
| 06338 | 58 | 3 | T1aN0M0 | 5 × 4 × 1.5 | none | −33.13 |

TABLE 1-continued

Patient Information

| Patient ID | Age | FIGO Grade | TNM Class | Tumor size (cm) | Metastases | PPME1 |
|---|---|---|---|---|---|---|
| 06457 | 63 | 3 | T1aN0M0 | 8.5 × 7.5 × 3.5 | none | ND |
| 06324 | 59 | <u>3</u> | T1bN0M0 | 3 × 1.5 × 1.5 | none | +6.409 |

All patients were female, Caucasian, and were diagnosed with Type I endometrial adenocarcinoma. All samples and patient reports were analyzed by our in-house pathologist to determine stage and grade of the tumors according to the International Federation of Gynecology and Obstetrics (FIGO) guidelines. Tumor grades that are in bold font and underlined could not be reassessed due to lack of remaining tumor material. The amount of PPME1 (the gene that codes for PME-1) normalized to the 18S house-keeping gene is shown as the fold-increase for tumor compared to NAT for each individual patient. ND=not determined

TABLE 2

DNA sequences of the PPME1 gene, which codes for PME-1, targeted by RNAi

| RNAi | Name | Sequence | Target Region |
|---|---|---|---|
| shRNA | Control shRNA | Scrambled Sequence | Non-targeting |
| | shPPME1 no. 1 | SEQ ID NO: 1: GTA CAG CTA TGG ATG CAC TTA | bp 554-574 |
| | shPPME1 no. 2 | SEQ ID NO: 2: GCA GCG ATT ATT AGT AGA GTT | bp 289-309 |
| | shPPME1 no. 3 | SEQ ID NO: 3: GGT GTT GAT AGA TTG GAT AAA | bp 964-984 |
| siRNA | Control siRNA | Scrambled Sequence | Non-targeting |
| | Target sequence no. 1 | TGG CTG GTG TTG ATA GAT T (SEQ ID NO: 4) | bp 959-977 |
| | PPME1 siRNA no. 1 | UGG CUG GUG UUG AUA GAU U (SEQ ID NO: 15) | |
| | Target sequence no. 2 | GTG GAT AGC ATC ACA AGA A (SEQ ID NO: 5) | 3'-UTR |
| | PPME1 siRNA no. 2 | GUG GAU AGC AUC ACA AGA A (SEQ ID NO: 16) | |
| | Target sequence no. 3 | GTA AAT ACG TCG CAC CAG A (SEQ ID NO: 6) | 3'-UTR |
| | PPME1 siRNA no. 3 | GUA AAU ACG UCG CAC CAG A (SEQ ID NO: 17) | |

Sequences are listed that target the PME-1 mRNA, which is 1,161 base pairs in length (targeted base pairs (base pairs) are shown). Two exemplary siRNAs target the 3'UTR region of the mRNA. The full sequence for the short hairpins used to target PPME1 are exemplary shPPME1 no. 1: 5'-CCGG-GTA CAG CTA TGG ATG CAC TTA-CTC GAG-TAA GTG CAT CCA TAG CTG TAC-TTTTT-3' (SEQ ID NO: 7), shPPME1 no. 2: 5'-CCGG-GCA GCG ATT ATT AGT AGA GTT-CTC GAG-AAC TCT ACT AAT AAT CGC TGC-TTTTT-3' (SEQ ID NO: 8), and shPPME1 no. 3: 5'-CCGG-GGT GTT GAT AGA TTG GAT AAA-CTC GAG-TTT ATC CAA TCT ATC AAC ACC-TTT TTG (SEQ ID NO: 9).

What is claimed is:

1. A method of treating a human subject suffering from triple negative breast cancer and is in need of treatment, comprising the steps of:
   a) identifying a human subject having triple negative breast cancer and in need of treatment thereof; and
   b) administering to said human subject an effective amount of RNAi targeted against PME-1 selected from the group consisting of siRNA and shRNA, wherein said RNAi reduces the gene expression of PME-1 in said triple negative breast cancer and thereby inhibits tumor growth of said triple negative breast cancer, and wherein said RNAi having a target sequence selected from the group consisting of SEQ ID NO: 17, SEQ ID NO: 2 and SEQ ID NO: 3.

2. A method of treating a human subject suffering from triple negative breast cancer and is in need of treatment, comprising the steps of:
   a) identifying a human subject having triple negative breast cancer and in need of treatment thereof; and
   b) administering to said human subject an effective amount of RNAi targeted against PME-1 wherein said RNAi reduces the gene expression of PME-1 in said triple negative breast cancer and thereby inhibits tumor growth of said triple negative breast cancer, and wherein said RNAi having a target sequence selected from the group consisting of SEQ ID NO: 8 and SEQ ID NO: 9.

3. A method of inhibiting tumor growth of a triple negative breast cancer cell, comprising the step of exposing a triple negative breast cancer cell with RNAi selected from the group consisting of siRNA and shRNA targeted against PME-1, wherein said RNAi reduces PME-1 gene expression and thereby inhibits tumor growth of said triple negative breast cancer cell, and
   wherein said RNAi having a target sequence selected from the group consisting of SEQ ID NO: 17, SEQ ID NO: 2 and SEQ ID NO: 3.

4. A method of inhibiting tumor growth of a triple negative breast cancer cell, comprising the step of exposing a triple negative breast cancer cell with RNAi targeted against PME-1, wherein said RNAi reduces PME-1 gene expression and thereby inhibits tumor growth of said triple negative breast cancer cell, and wherein said RNAi having a target sequence selected from the group consisting of SEQ ID NO: 8 and SEQ ID NO: 9.

5. A composition comprising shRNA contained in an adenoviral expression vector operably linked to said shRNA and a pharmaceutical acceptable excipient, wherein said shRNA having a target sequence consisting of SEQ ID NO: 2 or SEQ ID NO: 3.

* * * * *

SEQUENCE LISTING

<160> NUMBER OF SEQ ID NOS: 17

<210> SEQ ID NO 1
<211> LENGTH: 21
<212> TYPE: DNA
<213> ORGANISM: Homo sapiens

<400> SEQUENCE: 1
gtacagctat ggatgcactt a              21

<210> SEQ ID NO 2
<211> LENGTH: 21

<212> TYPE: DNA
<213> ORGANISM: Homo sapiens

<400> SEQUENCE: 2
gcagcgatta ttagtagagt t                                        21

<210> SEQ ID NO 3
<211> LENGTH: 21
<212> TYPE: DNA
<213> ORGANISM: Homo sapiens

<400> SEQUENCE: 3
ggtgttgata gattggataa a                                        21

<210> SEQ ID NO 4
<211> LENGTH: 19
<212> TYPE: DNA
<213> ORGANISM: Homo sapiens

<400> SEQUENCE: 4
tggctggtgt tgatagatt                                           19

<210> SEQ ID NO 5
<211> LENGTH: 19
<212> TYPE: DNA
<213> ORGANISM: Homo sapiens

<400> SEQUENCE: 5
gtggatagca tcacaagaa                                           19

<210> SEQ ID NO 6
<211> LENGTH: 19
<212> TYPE: DNA
<213> ORGANISM: Homo sapiens

<400> SEQUENCE: 6
gtaaatacgt cgcaccaga                                           19

<210> SEQ ID NO 7
<211> LENGTH: 57
<212> TYPE: DNA
<213> ORGANISM: Homo sapiens

<400> SEQUENCE: 7
ccgggtacag ctatggatgc acttactcga gtaagtgcat ccatagctgt accttttt    57

<210> SEQ ID NO 8
<211> LENGTH: 57
<212> TYPE: DNA
<213> ORGANISM: Homo sapiens

<400> SEQUENCE: 8
ccgggcagcg attattagta gagttctcga gaactctact aataatcgct gcttttt    57

<210> SEQ ID NO 9
<211> LENGTH: 58
<212> TYPE: DNA
<213> ORGANISM: Homo sapiens

<400> SEQUENCE: 9
ccggggtgtt gatagattgg ataaactcga gtttatccaa tctatcaaca cctttttg    58

<210> SEQ ID NO 10
<211> LENGTH: 1161
<212> TYPE: DNA
<213> ORGANISM: Homo sapiens

<400> SEQUENCE: 10

```
atgtcggccc tcgaaaagag catgcacctc ggccgccttc cctctcgccc acctctaccc      60
ggcagcgggg gcagtcagag cggagccaag atgcgaatgg gccctggaag aaagcgggac     120
ttttcccctg ttccttggag tcagtatttt gagtccatgg aagatgtaga agtagagaat     180
gaaactggca aggatacttt tcgagtctac aagagtggtt cagagggtcc agtcctgctc     240
cttctgcatg gaggaggtca ttctgccctt tcttgggctg tgttcacggc agcgattatt     300
agtagagttc agtgtaggat tgtagctttg gatctgcgaa gtcatggtga aacaaaggtc     360
aagaatcctg aagatctgtc tgcagaaaca atggcaaaag cgttggcaa tgtggttgaa     420
gccatgtatg gggaccttcc tcctccaatt atgctgattg acatagcat gggtggtgct     480
attgcagtcc acacagcatc atccaacctg gtaccaagcc tcttgggtct gtgcatgatt     540
gatgttgtag aaggtacagc tatggatgca cttaatagca tgcagaattt cttacggggt     600
cgtcctaaaa ccttcaagtc tctggagaat gctattgaat ggagtgtgaa gagtggccag     660
attcgaaatc tggagtctgc ccgtgtctca atggttggcc aagtcaaaca gtgtgaagga     720
attacaagtc cagaaggctc aaaatctata gtggaaggaa tcatagagga agaagaagaa     780
gatgaggaag gaagtgagtc tataagcaag aggaaaaagg aagatgacat ggagaccaag     840
aaagaccatc catacacctg gagaattgaa ctggcaaaaa cagaaaaata ctgggacggc     900
tggttccgag gcttatccaa tctctttctt agttgtccca ttcctaaatt gctgctcttg     960
gctggtgttg atagattgga taaagatctg accattggcc agatgcaagg gaagttccag    1020
atgcaggtcc taccccagtg tggccatgca gtccatgagg atgcccctga caaggtagct    1080
gaagctgttg ccactttcct gatccggcac aggtttgcag aacccatcgg tggattccag    1140
tgtgtgtttc ctggctgtta g                                              1161
```

<210> SEQ ID NO 11
<211> LENGTH: 386
<212> TYPE: PRT
<213> ORGANISM: Homo sapiens

<400> SEQUENCE: 11

```
Met Ser Ala Leu Glu Lys Ser Met His Leu Gly Arg Leu Pro Ser Arg
1               5                   10                  15

Pro Pro Leu Pro Gly Ser Gly Gly Ser Gln Ser Gly Ala Lys Met Arg
            20                  25                  30

Met Gly Pro Gly Arg Lys Arg Asp Phe Ser Pro Val Pro Trp Ser Gln
        35                  40                  45

Tyr Phe Glu Ser Met Glu Asp Val Glu Val Asn Glu Thr Gly Lys
    50                  55                  60

Asp Thr Phe Arg Val Tyr Lys Ser Gly Ser Glu Gly Pro Val Leu Leu
65                  70                  75                  80

Leu Leu His Gly Gly Gly His Ser Ala Leu Ser Trp Ala Val Phe Thr
                85                  90                  95

Ala Ala Ile Ile Ser Arg Val Gln Cys Arg Ile Val Ala Leu Asp Leu
            100                 105                 110

Arg Ser His Gly Glu Thr Lys Val Lys Asn Pro Glu Asp Leu Ser Ala
        115                 120                 125
```

```
Glu Thr Met Ala Lys Asp Val Gly Asn Val Val Ala Met Tyr Gly
            130                 135                 140

Asp Leu Pro Pro Pro Ile Met Leu Ile Gly His Ser Met Gly Gly Ala
145                 150                 155                 160

Ile Ala Val His Thr Ala Ser Ser Asn Leu Val Pro Ser Leu Leu Gly
                165                 170                 175

Leu Cys Met Ile Asp Val Val Glu Gly Thr Ala Met Asp Ala Leu Asn
                180                 185                 190

Ser Met Gln Asn Phe Leu Arg Gly Arg Pro Lys Thr Phe Lys Ser Leu
            195                 200                 205

Glu Asn Ala Ile Glu Trp Ser Val Lys Ser Gly Gln Ile Arg Asn Leu
210                 215                 220

Glu Ser Ala Arg Val Ser Met Val Gly Gln Val Lys Gln Cys Glu Gly
225                 230                 235                 240

Ile Thr Ser Pro Glu Gly Ser Lys Ser Ile Val Gly Ile Ile Glu
                245                 250                 255

Glu Glu Glu Glu Asp Glu Gly Ser Glu Ser Ile Ser Lys Arg Lys
                260                 265                 270

Lys Glu Asp Asp Met Glu Thr Lys Lys Asp His Pro Tyr Thr Trp Arg
            275                 280                 285

Ile Glu Leu Ala Lys Thr Glu Lys Tyr Trp Asp Gly Trp Phe Arg Gly
290                 295                 300

Leu Ser Asn Leu Phe Leu Ser Cys Pro Ile Pro Lys Leu Leu Leu
305                 310                 315                 320

Ala Gly Val Asp Arg Leu Asp Lys Asp Leu Thr Ile Gly Gln Met Gln
                325                 330                 335

Gly Lys Phe Gln Met Gln Val Leu Pro Gln Cys Gly His Ala Val His
            340                 345                 350

Glu Asp Ala Pro Asp Lys Val Ala Glu Ala Val Ala Thr Phe Leu Ile
            355                 360                 365

Arg His Arg Phe Ala Glu Pro Ile Gly Gly Phe Gln Cys Val Phe Pro
    370                 375                 380

Gly Cys
385

<210> SEQ ID NO 12
<211> LENGTH: 309
<212> TYPE: PRT
<213> ORGANISM: Homo sapiens

<400> SEQUENCE: 12

Met Asp Glu Lys Val Phe Thr Lys Glu Leu Asp Gln Trp Ile Glu Gln
1               5                   10                  15

Leu Asn Glu Cys Lys Gln Leu Ser Glu Ser Gln Val Lys Ser Leu Cys
            20                  25                  30

Glu Lys Ala Lys Glu Ile Leu Thr Lys Glu Ser Asn Val Gln Glu Val
        35                  40                  45

Arg Cys Pro Val Thr Val Cys Gly Asp Val His Gly Gln Phe His Asp
    50                  55                  60

Leu Met Glu Leu Phe Arg Ile Gly Gly Lys Ser Pro Asp Thr Asn Tyr
65                  70                  75                  80

Leu Phe Met Gly Asp Tyr Val Asp Arg Gly Tyr Tyr Ser Val Glu Thr
                85                  90                  95

Val Thr Leu Leu Val Ala Leu Lys Val Arg Tyr Arg Glu Arg Ile Thr
            100                 105                 110
```

```
Ile Leu Arg Gly Asn His Glu Ser Arg Gln Ile Thr Gln Val Tyr Gly
            115                 120                 125

Phe Tyr Asp Glu Cys Leu Arg Lys Tyr Gly Asn Ala Asn Val Trp Lys
130                 135                 140

Tyr Phe Thr Asp Leu Phe Asp Tyr Leu Pro Leu Thr Ala Leu Val Asp
145                 150                 155                 160

Gly Gln Ile Phe Cys Leu His Gly Gly Leu Ser Pro Ser Ile Asp Thr
                165                 170                 175

Leu Asp His Ile Arg Ala Leu Asp Arg Leu Gln Glu Val Pro His Glu
            180                 185                 190

Gly Pro Met Cys Asp Leu Leu Trp Ser Asp Pro Asp Asp Arg Gly Gly
            195                 200                 205

Trp Gly Ile Ser Pro Arg Gly Ala Gly Tyr Thr Phe Gly Gln Asp Ile
        210                 215                 220

Ser Glu Thr Phe Asn His Ala Asn Gly Leu Thr Leu Val Ser Arg Ala
225                 230                 235                 240

His Gln Leu Val Met Glu Gly Tyr Asn Trp Cys His Asp Arg Asn Val
                245                 250                 255

Val Thr Ile Phe Ser Ala Pro Asn Tyr Cys Tyr Arg Cys Gly Asn Gln
            260                 265                 270

Ala Ala Ile Met Glu Leu Asp Asp Thr Leu Lys Tyr Ser Phe Leu Gln
        275                 280                 285

Phe Asp Pro Ala Pro Arg Arg Gly Glu Pro His Val Thr Arg Arg Thr
    290                 295                 300

Pro Asp Tyr Phe Leu
305

<210> SEQ ID NO 13
<211> LENGTH: 307
<212> TYPE: PRT
<213> ORGANISM: Homo sapiens

<400> SEQUENCE: 13

Met Ala Glu Ile Ser Asp Leu Asp Arg Gln Ile Glu Gln Leu Arg Arg
1               5                   10                  15

Cys Glu Leu Ile Lys Glu Ser Glu Val Lys Ala Leu Cys Ala Lys Ala
                20                  25                  30

Arg Glu Ile Leu Val Glu Ser Asn Val Gln Arg Val Asp Ser Pro
            35                  40                  45

Val Thr Val Cys Gly Asp Ile His Gly Gln Phe Tyr Asp Leu Lys Glu
50                  55                  60

Leu Phe Arg Val Gly Gly Asp Val Pro Glu Thr Asn Tyr Leu Phe Met
65                  70                  75                  80

Gly Asp Phe Val Asp Arg Gly Phe Tyr Ser Val Glu Thr Phe Leu Leu
                85                  90                  95

Leu Leu Ala Leu Lys Val Arg Tyr Pro Asp Arg Ile Thr Leu Ile Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Ser Val Thr Val Trp Arg Tyr Cys Thr
    130                 135                 140

Glu Ile Phe Asp Tyr Leu Ser Leu Ser Ala Ile Ile Asp Gly Lys Ile
145                 150                 155                 160

Phe Cys Val His Gly Gly Leu Ser Pro Ser Ile Gln Thr Leu Asp Gln
                165                 170                 175
```

```
Ile Arg Thr Ile Asp Arg Lys Gln Glu Val Pro His Asp Gly Pro Met
            180                 185                 190

Cys Asp Leu Leu Trp Ser Asp Pro Glu Asp Thr Thr Gly Trp Gly Val
        195                 200                 205

Ser Pro Arg Gly Ala Gly Tyr Leu Phe Gly Ser Asp Val Val Ala Gln
    210                 215                 220

Phe Asn Ala Ala Asn Asp Ile Asp Met Ile Cys Arg Ala His Gln Leu
225                 230                 235                 240

Val Met Glu Gly Tyr Lys Trp His Phe Asn Thr Val Leu Thr Val
                245                 250                 255

Trp Ser Ala Pro Asn Tyr Cys Tyr Arg Cys Gly Asn Val Ala Ala Ile
            260                 265                 270

Leu Glu Leu Asp Glu His Leu Gln Lys Asp Phe Ile Ile Phe Glu Ala
        275                 280                 285

Ala Pro Gln Glu Thr Arg Gly Ile Pro Ser Lys Lys Pro Val Ala Asp
    290                 295                 300

Tyr Phe Leu
305

<210> SEQ ID NO 14
<211> LENGTH: 305
<212> TYPE: PRT
<213> ORGANISM: Homo sapiens

<400> SEQUENCE: 14

Met Ala Pro Leu Asp Leu Asp Lys Tyr Val Glu Ile Ala Arg Leu Cys
1               5                   10                  15

Lys Tyr Leu Pro Glu Asn Asp Leu Lys Arg Leu Cys Asp Tyr Val Cys
            20                  25                  30

Asp Leu Leu Leu Glu Glu Ser Asn Val Gln Pro Val Ser Thr Pro Val
        35                  40                  45

Thr Val Cys Gly Asp Ile His Gly Gln Phe Tyr Asp Leu Cys Glu Leu
    50                  55                  60

Phe Arg Thr Gly Gly Gln Val Pro Asp Thr Asn Tyr Ile Phe Met Gly
65                  70                  75                  80

Asp Phe Val Asp Arg Gly Tyr Tyr Ser Leu Glu Thr Phe Thr Tyr Leu
                85                  90                  95

Leu Ala Leu Lys Ala Lys Trp Pro Asp Arg Ile Thr Leu Leu Arg Gly
            100                 105                 110

Asn His Glu Ser Arg Gln Ile Thr Gln Val Tyr Gly Phe Tyr Asp Glu
        115                 120                 125

Cys Gln Thr Lys Tyr Gly Asn Ala Asn Ala Trp Arg Tyr Cys Thr Lys
    130                 135                 140

Val Phe Asp Met Leu Thr Val Ala Ala Leu Ile Asp Glu Gln Ile Leu
145                 150                 155                 160

Cys Val His Gly Gly Leu Ser Pro Asp Ile Lys Thr Leu Asp Gln Ile
                165                 170                 175

Arg Thr Ile Glu Arg Asn Gln Glu Ile Pro His Lys Gly Ala Phe Cys
            180                 185                 190

Asp Leu Val Trp Ser Asp Pro Glu Asp Val Asp Thr Trp Ala Ile Ser
        195                 200                 205

Pro Arg Gly Ala Gly Trp Leu Phe Gly Ala Lys Val Thr Asn Glu Phe
    210                 215                 220

Val His Ile Asn Asn Leu Lys Leu Ile Cys Arg Ala His Gln Leu Val
225                 230                 235                 240
```

```
His Glu Gly Tyr Lys Phe Met Phe Asp Glu Lys Leu Val Thr Val Trp
                245                 250                 255

Ser Ala Pro Asn Tyr Cys Tyr Arg Cys Gly Asn Ile Ala Ser Ile Met
            260                 265                 270

Val Phe Lys Asp Val Asn Thr Arg Glu Pro Lys Leu Phe Arg Ala Val
        275                 280                 285

Pro Asp Ser Glu Arg Val Ile Pro Pro Arg Thr Thr Thr Pro Tyr Phe
    290                 295                 300

Leu
305

<210> SEQ ID NO 15
<211> LENGTH: 19
<212> TYPE: RNA
<213> ORGANISM: Artificial Sequence
<220> FEATURE:
<223> OTHER INFORMATION: siRNA

<400> SEQUENCE: 15
uggcuggugu ugauagauu                                              19

<210> SEQ ID NO 16
<211> LENGTH: 19
<212> TYPE: RNA
<213> ORGANISM: Artificial Sequence
<220> FEATURE:
<223> OTHER INFORMATION: siRNA

<400> SEQUENCE: 16
guggauagca ucacaagaa                                              19

<210> SEQ ID NO 17
<211> LENGTH: 19
<212> TYPE: RNA
<213> ORGANISM: Artificial Sequence
<220> FEATURE:
<223> OTHER INFORMATION: siRNA

<400> SEQUENCE: 17
guaaauacgu cgcaccaga                                              19
```